US010501800B2

(12) United States Patent
Lange et al.

(10) Patent No.: US 10,501,800 B2
(45) Date of Patent: Dec. 10, 2019

(54) BREAST CANCER PROGNOSIS

(71) Applicant: Regents of the University of Minnesota, Minneapolis, MN (US)

(72) Inventors: Carol Ann Lange, Minneapolis, MN (US); Todd Philip Knutson, Plymouth, MN (US); Jason Basil Nikas, Minnetrista, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 13/843,482

(22) Filed: Mar. 15, 2013

(65) Prior Publication Data

US 2013/0316992 A1    Nov. 28, 2013

Related U.S. Application Data

(60) Provisional application No. 61/639,407, filed on Apr. 27, 2012.

(51) Int. Cl.
*C12Q 1/6886* (2018.01)

(52) U.S. Cl.
CPC ..... *C12Q 1/6886* (2013.01); *C12Q 2600/106* (2013.01); *C12Q 2600/158* (2013.01)

(58) Field of Classification Search
None
See application file for complete search history.

(56) References Cited

U.S. PATENT DOCUMENTS 6,750,015 B2 * 6/2004 Horwitz ............... C12Q 1/6886
435/6.17

FOREIGN PATENT DOCUMENTS

| EP | 2841594 A1 | 3/2015 |
| JP | 2015516155 A | 6/2015 |
| KR | 1020150028232 A | 3/2015 |
| WO | WO-02/00618 A2 | 1/2002 |
| WO | WO-2013/162776 A1 | 10/2013 |

OTHER PUBLICATIONS

Meijer, D. et al. Breast Cancer Res Treat 113:253 (2009).*
Knutson, T.P. et al. Breast Cancer Research 14:R95 (Jun. 2012).*
Klijn, J.G.M. et al. Steroids 65:825 (2000).*
"International Application Serial No. PCT/US2013/032677, International Search Report dated Oct. 9, 2013", 11 pgs.
"International Application Serial No. PCT/US2013/032677, Invitation to Pay Additional Fees and Partial Search Report dated Mar. 12, 2013", 9 pgs.

(Continued)

*Primary Examiner* — Diana B Johannsen
(74) *Attorney, Agent, or Firm* — Schwegman Lundberg & Woessner, P.A.

(57) ABSTRACT

The present invention provides gene expression profiles indicative of whether a patient afflicted with PR driven malignancies is likely to be responsive to treatment with a therapeutic compound that is an anti-progestin. By identifying such responsiveness, a treatment provider may determine in advance those patients who would benefit from such treatment, as well as identify alternative therapies for non-responders. Also, provided are methods of using gene expression profiles and assays for identifying the presence of a gene expression profile in a patient.

2 Claims, 55 Drawing Sheets
Specification includes a Sequence Listing.

(56) References Cited

OTHER PUBLICATIONS

"International Application Serial No. PCT/US2013/032677, Written Opinion dated Oct. 9, 2013", 18 pgs.

Abdel-Hafiz, Hany A, et al., "Control of progesterone receptor transcriptional synergy by SUMOylation and deSUMOylation", *BMC Molecular Biology*, 13(1), (2012), 1-18.

Abdel-Hafiz, Hany, et al., "Mechanisms Underlying the Control of Progesterone Receptor Transcriptional Activity by SUMOylation", *Journal of Biological Chemistry*, 284(14), (2009), 9099-9108.

Daniel, Andrea R, et al., "Protein kinases mediate ligand-independent derepression of sumoylated progesterone receptors in breast cancer cells", *Proc. Natl. Acad. Sci. USA*. 106(34), (2009), 14287-14292.

Knutson, Todd P, "Phosphorylated and sumoylation-deficient progesterone receptors drive proliferative gene signatures during breast cancer progression", *Breast Cancer Research*, 14(3), (2012), 1-23

"European Application Ser. No. 13714144.6, Office Action dated Dec. 5, 2014", 2 pgs.

"European Application Ser. No. 13714144.6, Response filed Jun. 4, 2015 to Office Action dated Dec. 5, 2014", 21 pgs.

"International Application Serial No. PCT/US2013/032677, Response filed Sep. 12, 2013 to Invitation to Pay Additional Fees dated Aug. 12, 2013", 1 pg.

"New Zealand Application Serial No. 701652, First Examiner Report dated Sep. 28, 2015", 4 pgs.

Beerli, Roger R., et al,, "Epidermal Growth Factor-related Peptides Activate Distinct Subsetsof ErbB Receptors and Differ in Their Biological Activities", *Journal of Biological Chemistry*, 271(11), (1996), 6071-6076.

Bonnefoi, Herve, et al., "Validation of gene signatures that predict the response of breast cancer to neoadjuvant chemotherapy: a substudy of the EORTC 10994/BIG 00-01 clinical trial", *Lancet Oncol.*, 8(12), (2007), 1071-1078.

Byron, S. A., et al., "Insulin receptor substrates mediate distinct biological responses to insulin-like growth factor receptor activation in breast cancer cells", *British Journal of Cancer*, 95(9), (2006), 1220-1228.

Chang, A. C-M, et al., "Mammalian stanniocalcins and cancer", *Endocrine-Related Cancer*, 10(3), (2003), 359-373.

Clemm, David L., et al., "Differential Hormone-Dependent Phosphorylation of Progesterone Receptor A and B Forms Revealed by a Phosphoserine Site-Specific Monoclonal Antibody", *Molecular Endocrinology*. 14(1), (2000), 52-65.

Daniel, Andrea R., et al., "Linkage of progestin and epidermal growth factor signaling:Phosphorylation of progesterone receptors mediates transcriptional hypersensitivity and increased ligand-independent breast cancer cell growth", *Steroids*, 72(2), (2007), 188-201.

Daniel, Andrea R., et al., "Phosphorylation-Dependent Antagonism of Sumoylation Derepresses Progesterone Receptor Action in Breast Cancer Cells", *Molecular Endocrinology*, 21(12):, (2007), :2890-2906.

Daniel, Andrea R., et al., "Progesterone receptor action: defining a role in breast cancer", NIH Public Access, published in final edited form as: *Expert Rev. Endocrinol. Metab.*, 6(3), 359-369, (2011), 20 pgs.

Daniel, Andrea R., et al., "Signaling inputs to progesterone receptor gene regulation andpromoter selectivity", *Molecular and Cellular Endocrinology*, 308(1-2), (2009), 47-52.

De Vivo, Immaculata, et al., "A functional polymorphism in the promoter of the progesterone receptor gene associated with endometrial cancer risk", *Proc. Natl. Acad. Sci. USA*, 99(19), (2002), 12263-12268.

Geiss-Friedlander, Ruth, et al., "Concepts in sumoylation: a decade on", *Nature Reviews Molecular Cell Biology*, 8. (Dec. 2007), 947-956.

Geiss-Friedlander, Ruth, et al., "Concepts in sumoylation: a decade on", Supplementary information S1 (table) | *Saccharomyces cerevisiae* proteins of the SUMO pathway, *Nature Reviews Molecular Cell Biology*, 8 (Dec. 2007), 2 pgs.

Geiss-Friedlander, Ruth, et al., "Concepts in sumoylation: a decade on", Supplementary information S2 (table) | Human proteins of the SUMO pathway, *Nature Reviews Molecular Cell Biology*, 8 (Dec. 2007), 4 pgs.

Graham, J. Dinny, et al., "DNA Replication Licensing and Progenitor Numbers Are Increased by Progesterone in Normal Human Breast", *Endocrinology*, 150(7), (2009), 3318-3326.

Iniguez-Lluhi, Jorge A., et al., "A Common Motif within the Negative Regulatory Regions of Multiple Factors Inhibits Their Transcriptional Synergy", *Molecular and Cellular Biology*, 20(16), (Aug. 2000), 6040-6050.

Jacobsen, Britta M., et al., "Progesterone-Independent Effects of Human Progesterone Receptors (PRs) in Estrogen Receptor-Positive Breast Cancer: PR Isoform-Specific Gene Regulation and Tumor Biology", *Molecular Endocrinology*, 19(3), (2005), 574-587.

Lange, Carol A., "Challenges to defining a role for progesterone in breast cancer", *Steroids*, 73(9-10), (2008), 914-921.

Lange, Carol A., et al., "Phosphorylation of human progesterone receptors at serine-294 by mitogen-activated protein kinase signals their degradation by the 26S proteasome". *Proc. Natl. Acad. Sci. USA*, 97(3), (2000), 1032-1037.

Liu, Shuzhen, et al., "Progesterone receptor is a significant factor associated with clinical outcomes and effect of adjuvant tamoxifen therapy in breast cancer patients", *Breast Cancer Res. Treat.*, 119(1), (2010), 53-61

Loi, Sherene, et al., "Definition of Clinically Distinct Molecular Subtypes in Estrogen Receptor-Positive Breast CarcinomasThrough Genomic Grade", *J. Clin. Oncol.*, 25(10), (2007), 1239-1246.

Paik, Soonmyung, et al., "A Multigene Assay to Predict Recurrence of Tamoxifen-Treated, Node-Negative Breast Cancer", *N. Engl. J. Med.*, 351(27), (2004), 2817-2826.

Parker, Joel S., et al., "Supervised Risk Predictor of Breast Cancer Based on Intrinsic Subtypes", *J. Clin. Oncol.*, 27(8), (2009), 1160-1167.

Pooley, Karen A., et al., "Association of the Progesterone Receptor Gene with Breast Cancer Risk: A Single-Nucleotide Polymorphism Tagging Approach", *Cancer Epidemiol. Biomarkers Prev.*, 15(4), (Apr. 2006), 675-682.

Rhodes, Daniel R., et al., "Oncomine 3.0: Genes, Pathways, and Networks in a Collection of 18,000 Cancer Gene Expression Profiles", *Neoplasia*, 9(2), (Feb. 2007,), 166-180.

Richer, Jennifer K.. et al., "Differential Gene Regulation by the Two Progesterone Receptor Isoforms in Human Breast Cancer Cells", *Journal of Biological Chemistry*, 277(7), (2002), 5209-5218.

Terry, Kathryn L., et al., "Genetic Variation in the Progesterone Receptor Gene and Ovarian Came Risk", *American Journal of Epidemiology*, 161(5), (2005), 442-451.

Van 'T Veer, Laura J., et al., "Gene expression profiling predicts clinical outcome of breast cancer", *Nature*, 415(6871), (2002), 530-536.

Vicent, Guillermo P., et al., "Four enzymes cooperate to displace histone H1 during the first minute of hormonal gene activation", *Genes & Development*, 25(8), (2011), 845-862.

Vicent, Guillermo P., et al., "Four enzymes cooperate to displace histone H1 during the first minute of hormonal gene activation", Supplemental Information, *Genes & Development*, 25(8), (2011), 4 pgs.

"International Application Serial No. PCT/US2013/032677, International Preliminary Report on Patentability dated Nov. 6, 2014", 20 pgs.

"Israeli Application Serial No. 235351, Notification Prior to Examination dated Jan. 31, 2016", (English Translation), 3 pgs.

"European Application Ser. No. 13714144.6, Office Action dated Nov. 17, 201515", 4 pgs.

"European Application Ser. No. 13714144.6, Response filed May 24, 2016 to Office Action dated Nov. 17, 2015", 12 pgs.

"New Zealand Application Serial No. 701652, Response filed Apr. 28, 2016 to First Examiner Report dated Sep. 28, 2015", 3 pgs.

(56) References Cited

OTHER PUBLICATIONS

"New Zealand Application Serial No. 701652, Subsequent Examination Report dated May 24, 2016", 3 pgs.
"European Application Ser. No. 13714144.6, Office Action dated Jun. 8, 2016", 3 pgs.
"European Application Ser. No. 13714144.6,Response filed Dec. 15, 2016 to Office Action dated Jun. 8, 2016", 192 pgs.
"Japanese Application Serial No. 2015-508975, Office Action dated Feb. 13, 2017", W/ English Translation, 9 pgs.
"Russian Application Serial No. 2014147625, Office Action dated Mar. 20, 2017", With English Translation, 6 pgs.

\* cited by examiner

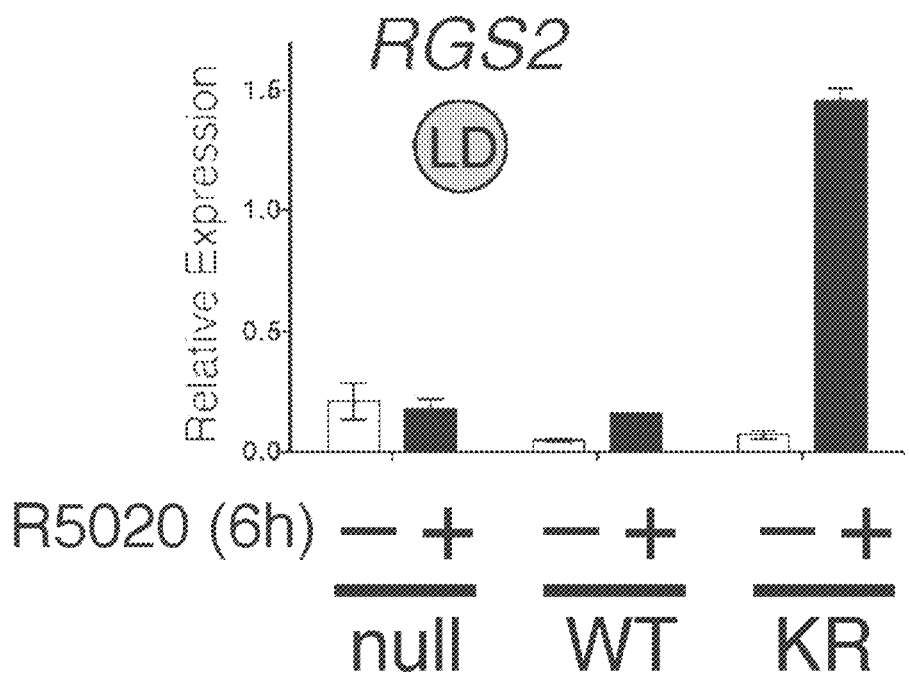
Fig.1F1
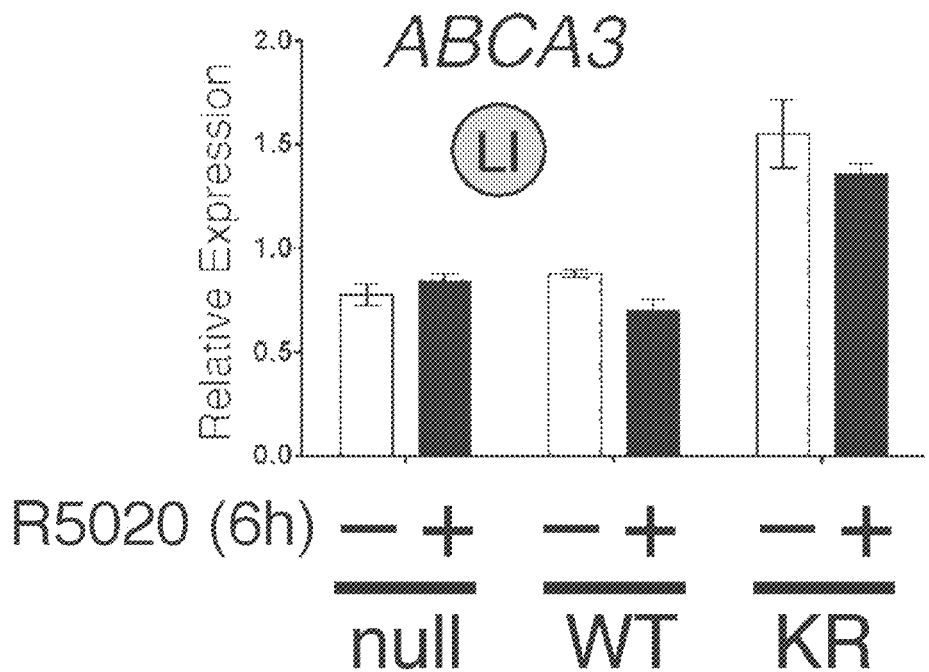
Fig.1F2

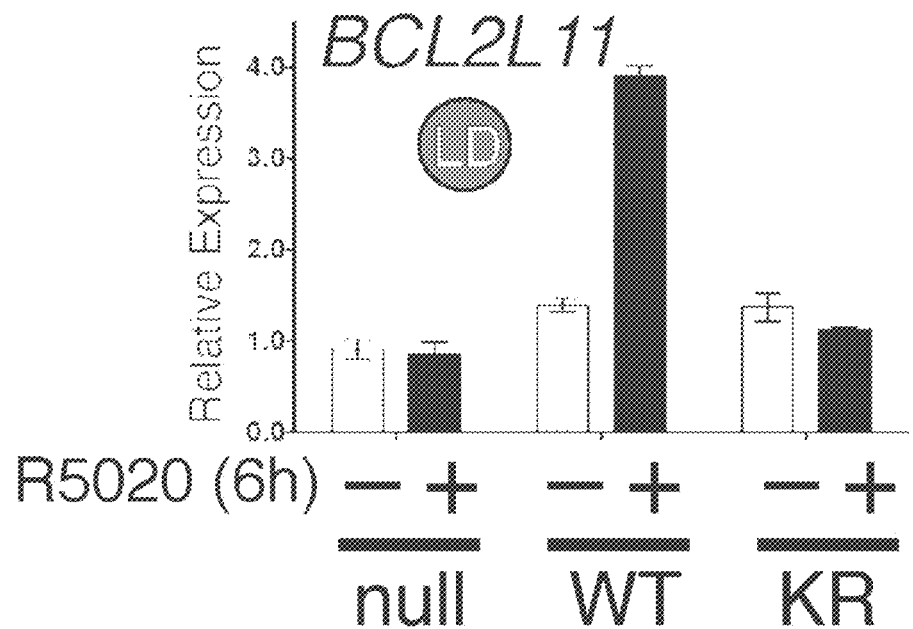
Fig. 1F3
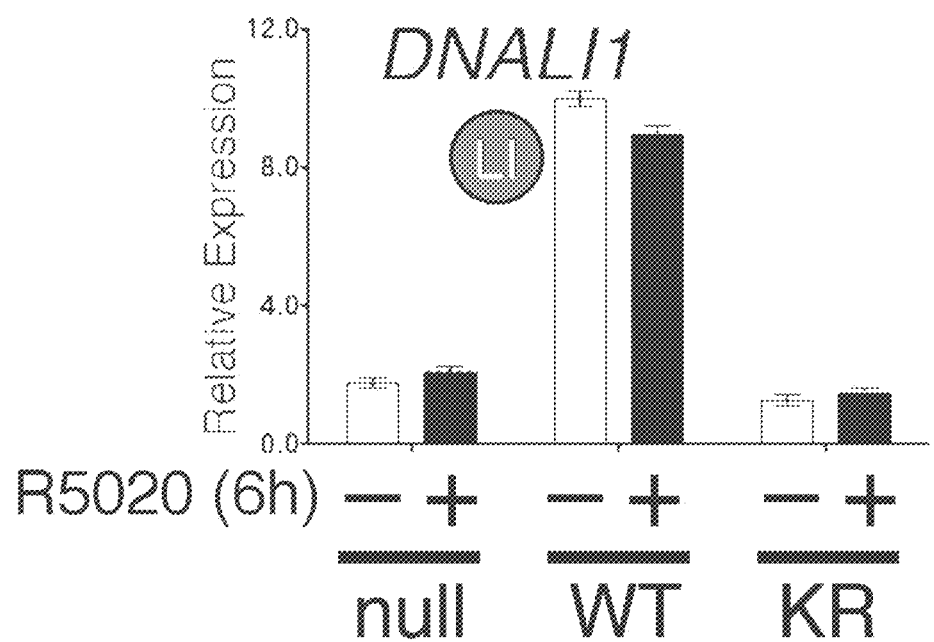
Fig. 1F4

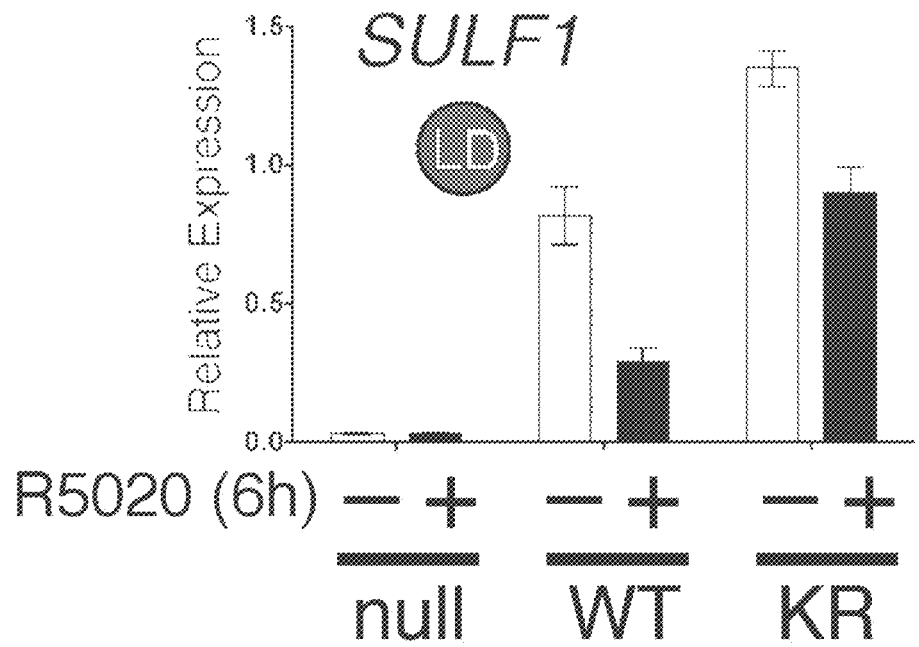
Fig.1F5
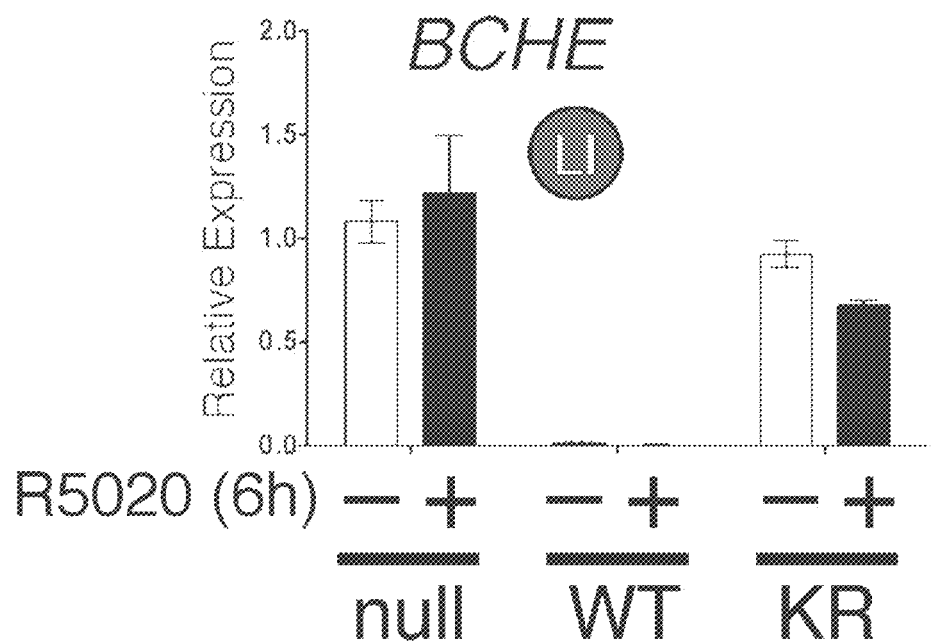
Fig.1F6

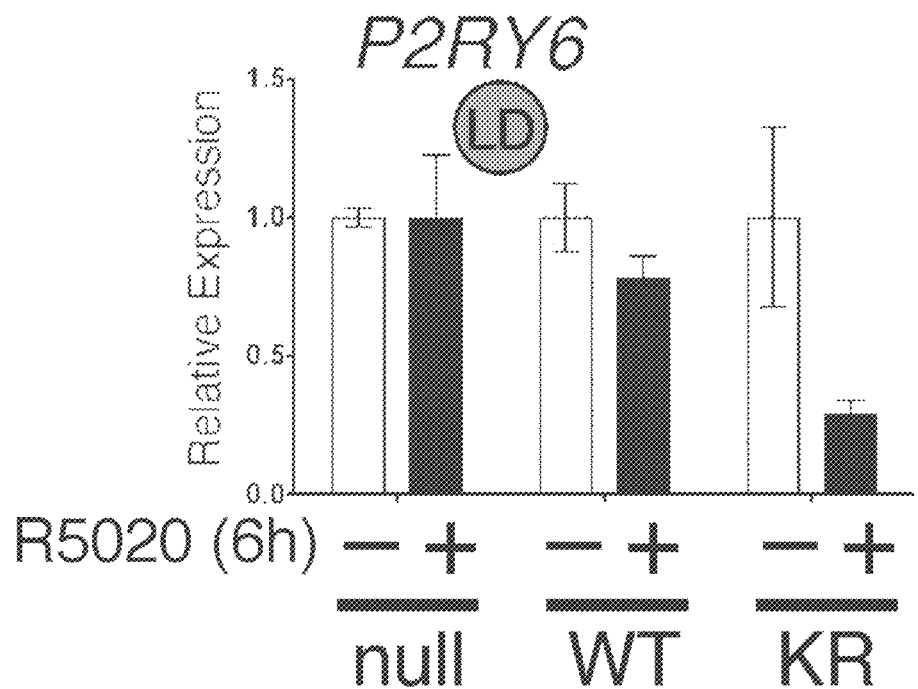
Fig.1F7
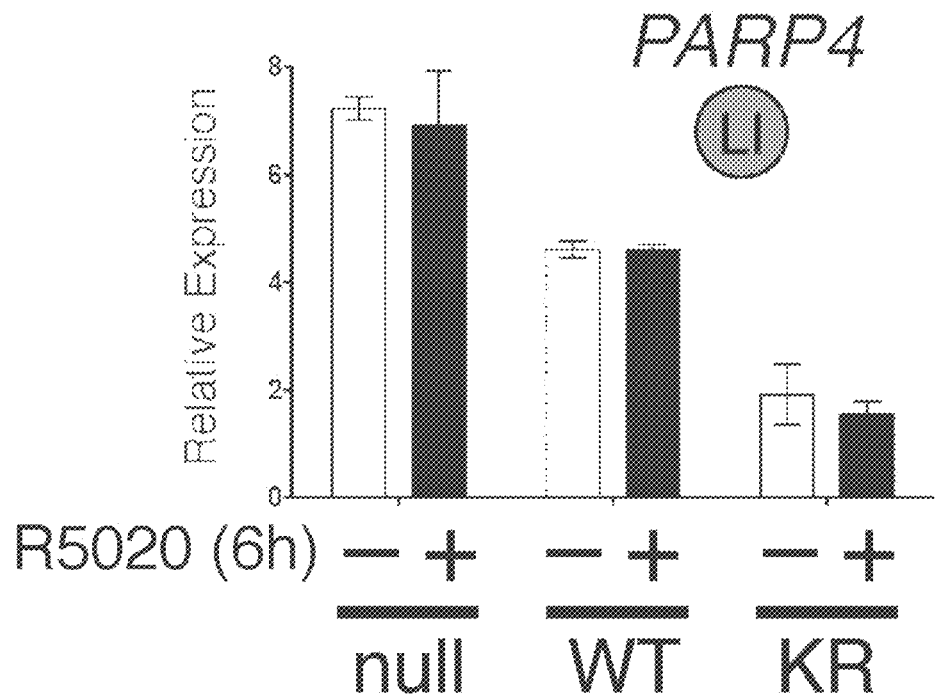
Fig.1F8

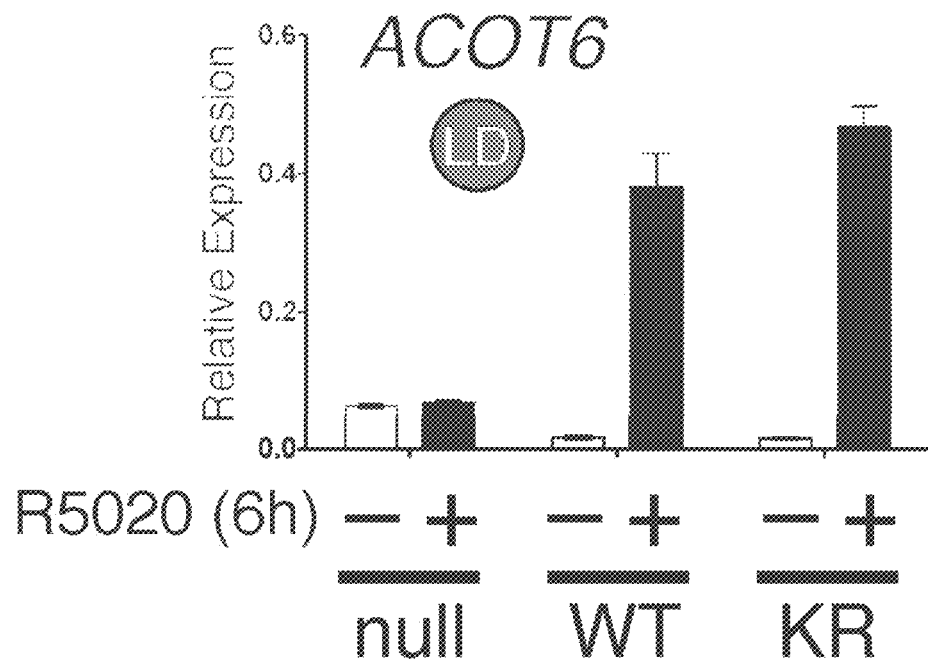
Fig.1F9
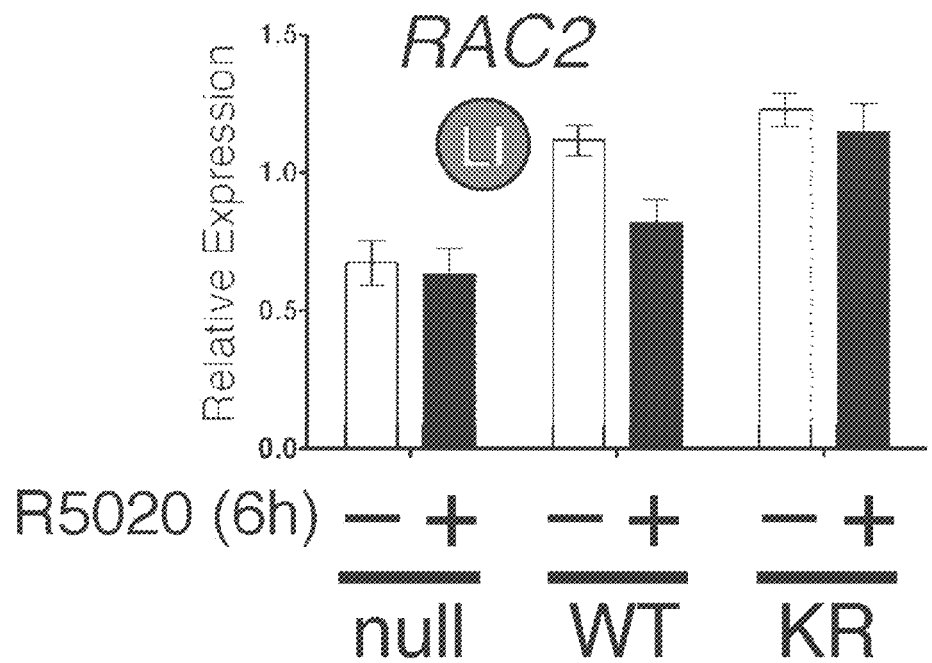
Fig.1F10

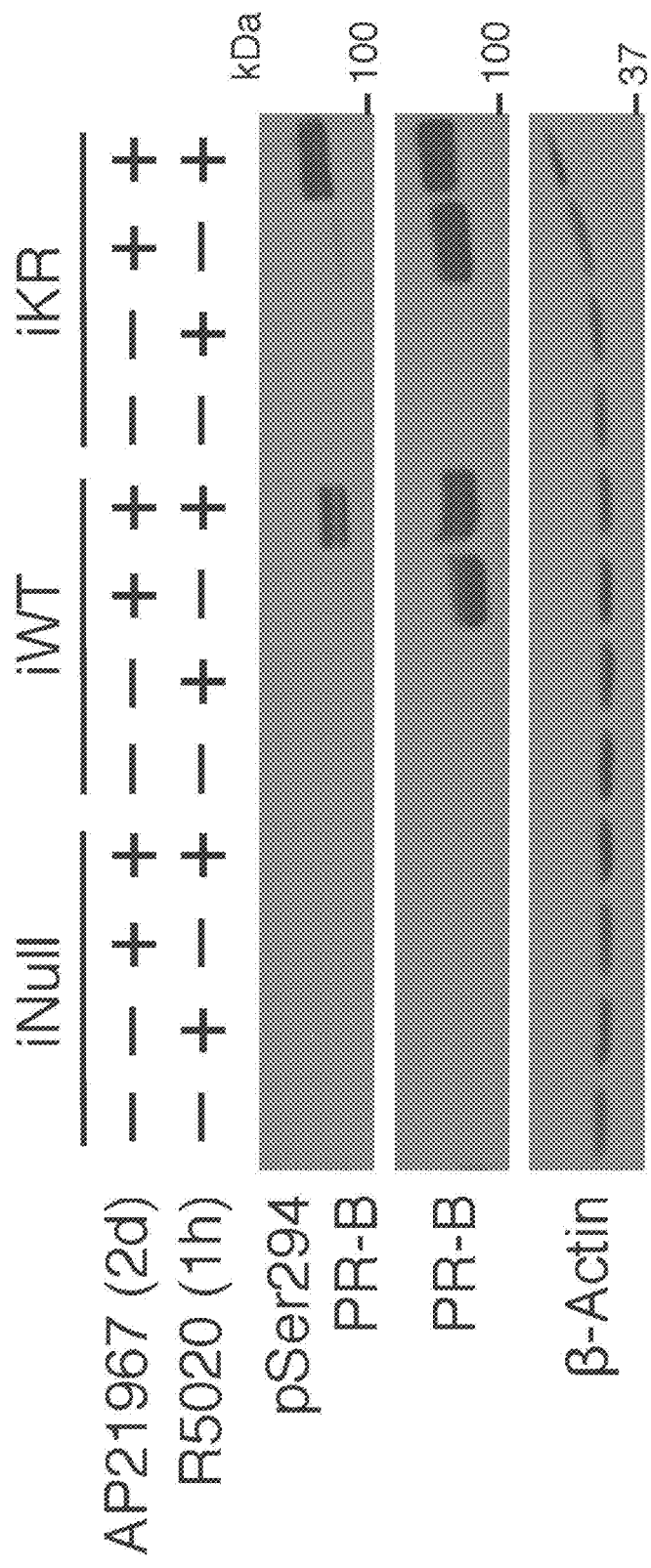
Fig. 1.1A

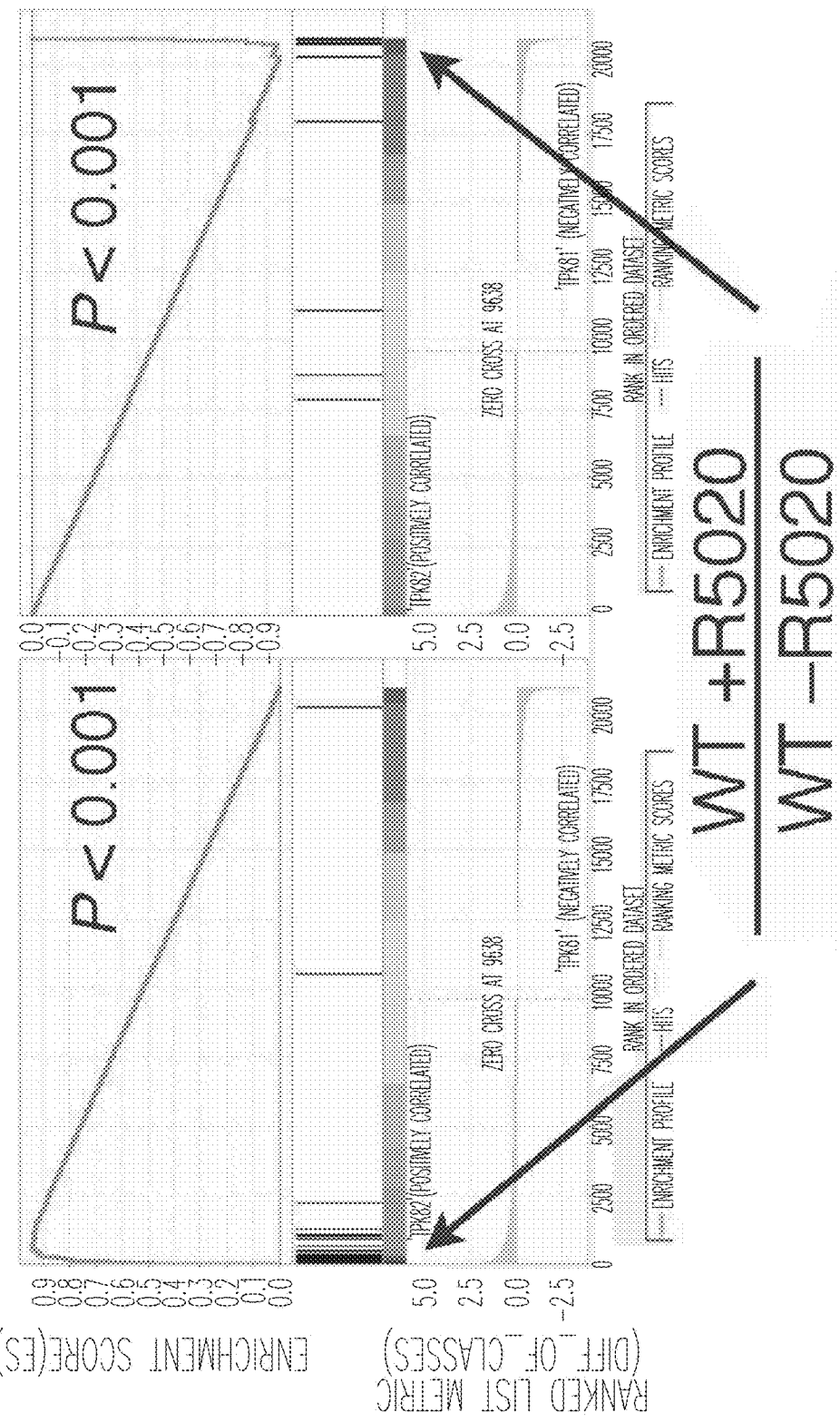
Fig. 1.1B1

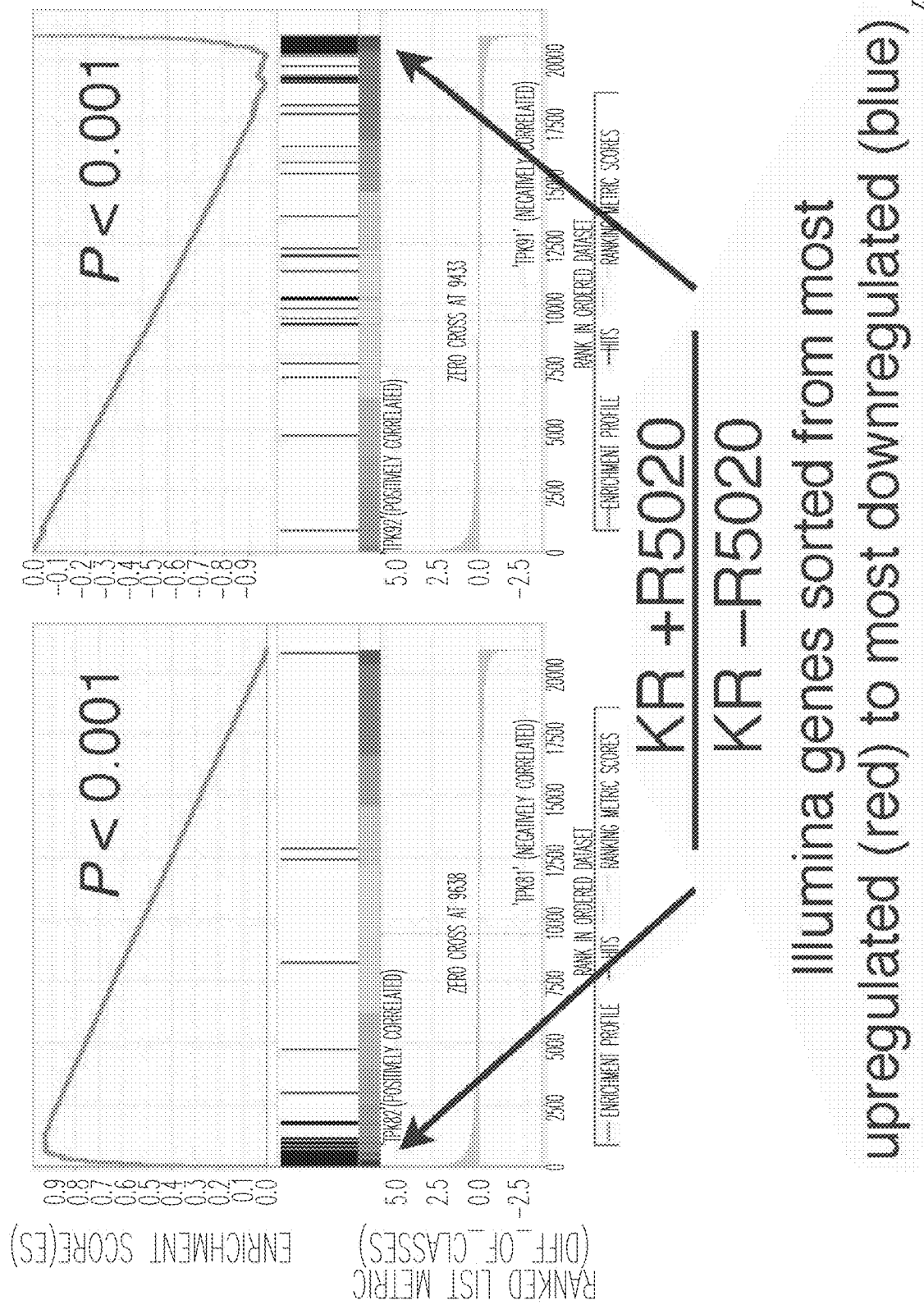
Fig. 1.1B2

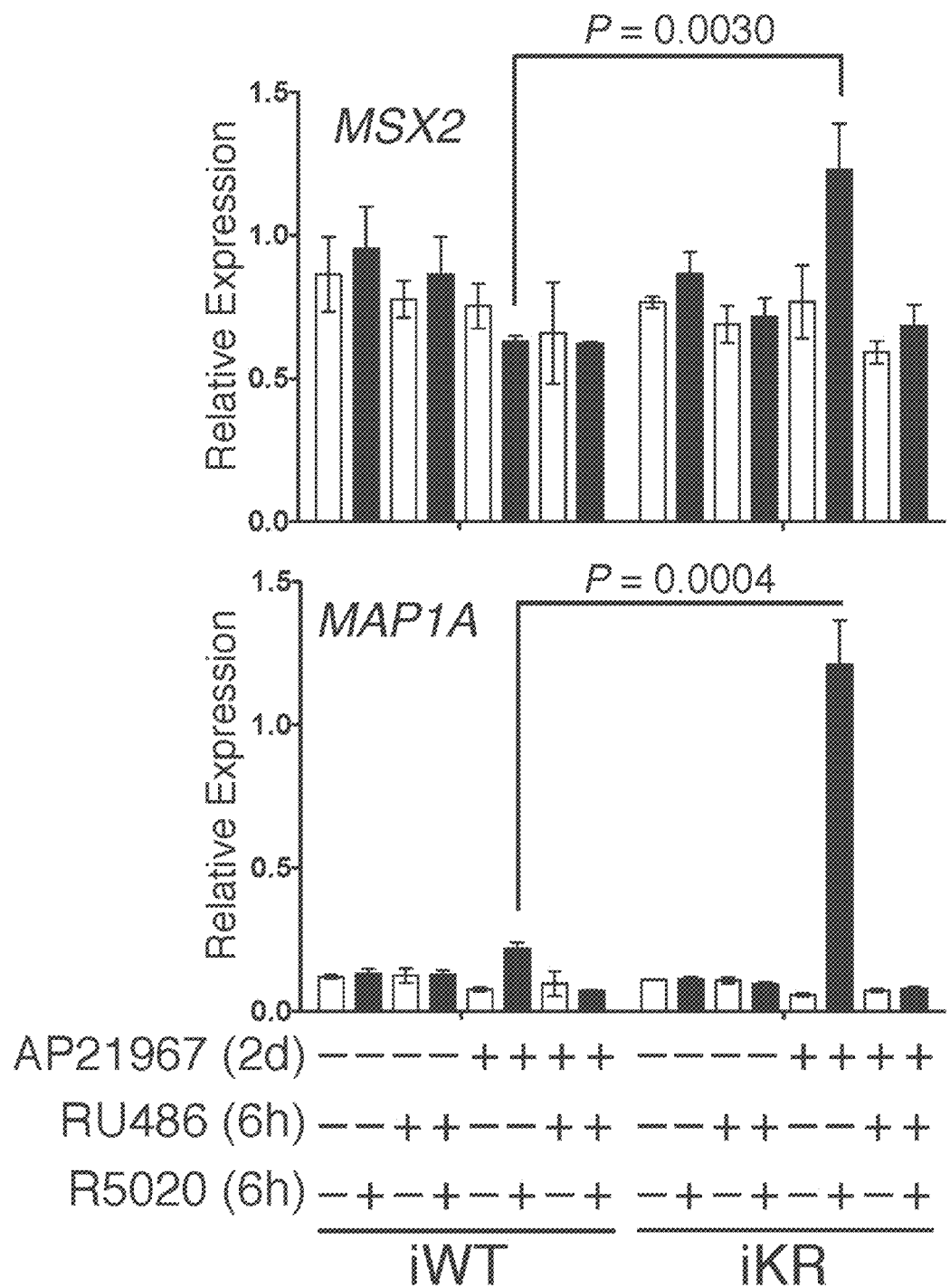
Fig. 1.1C

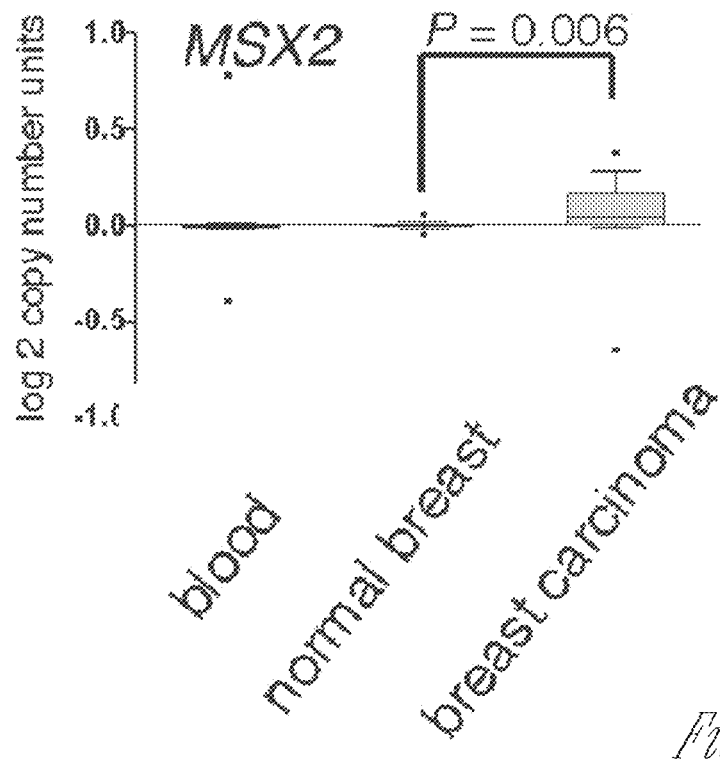
Fig.2A1
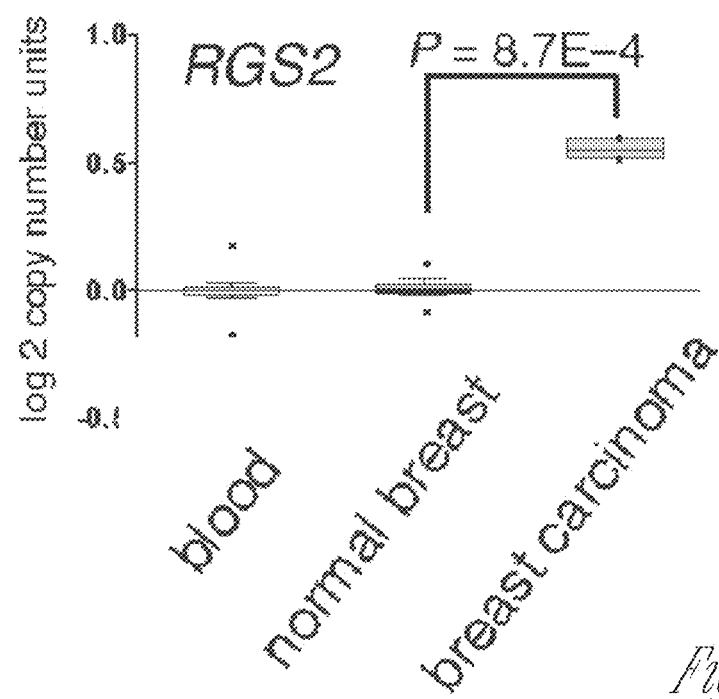
Fig.2A2

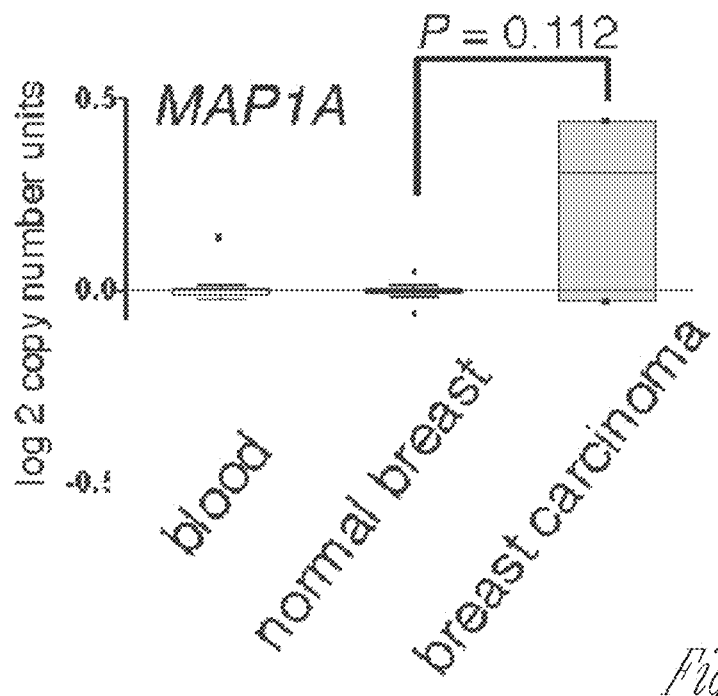
Fig.2A3
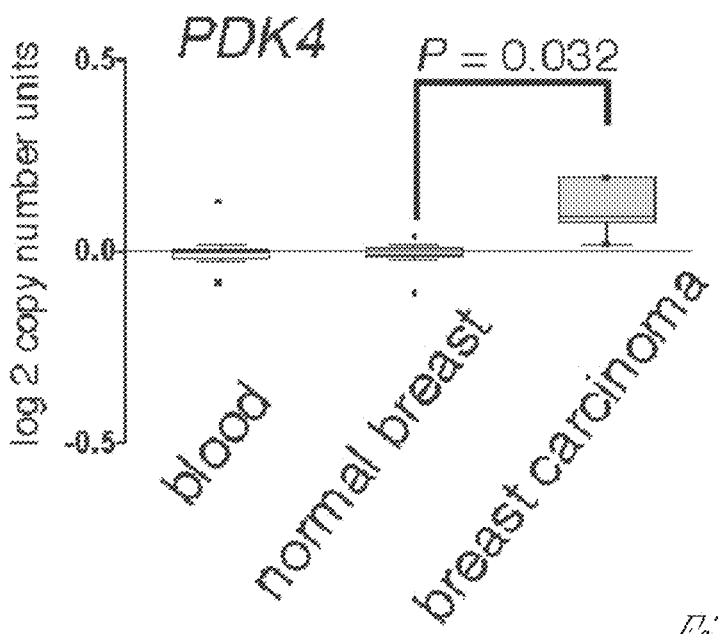
Fig.2A4

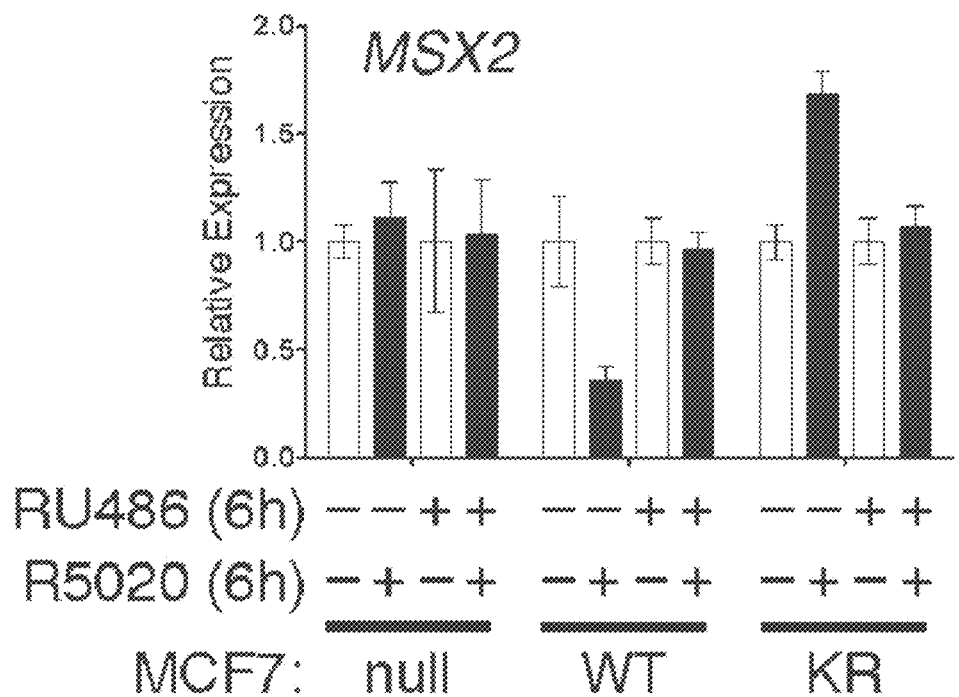
Fig.2B1
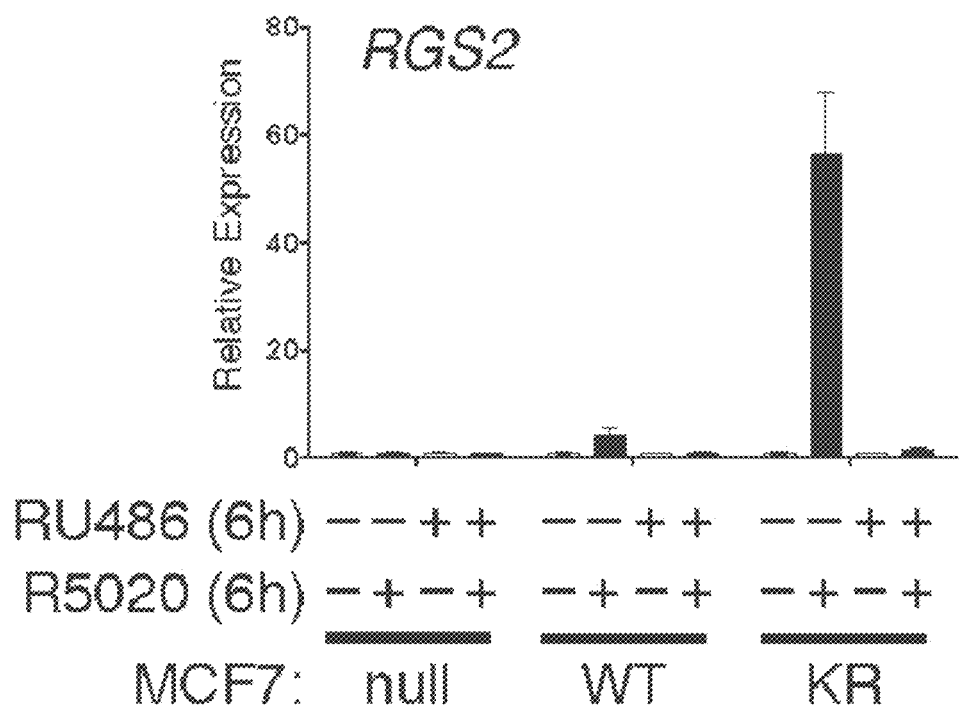
Fig.2B2

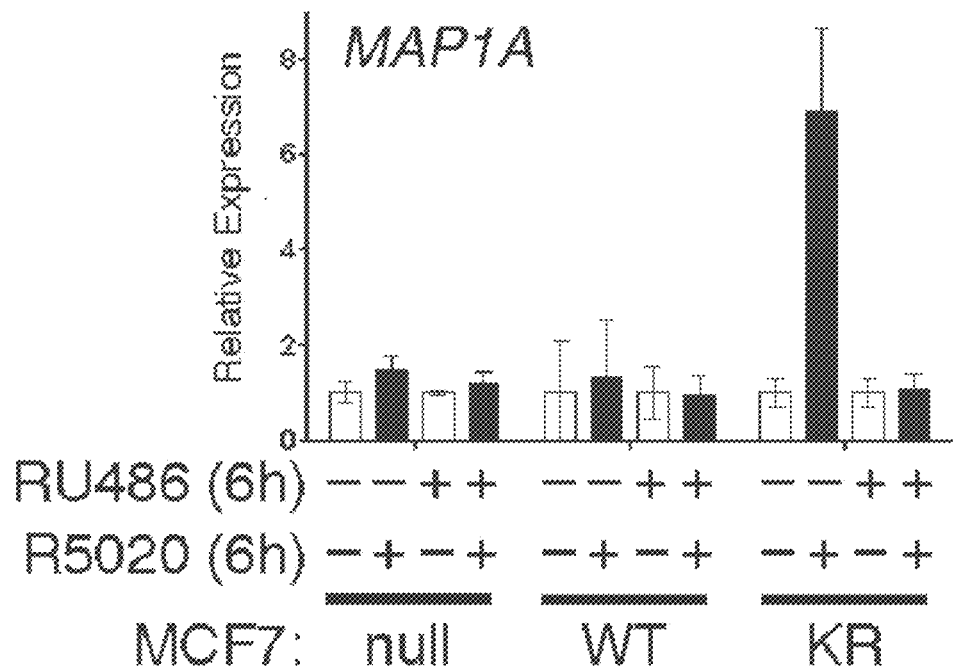
Fig. 2B3
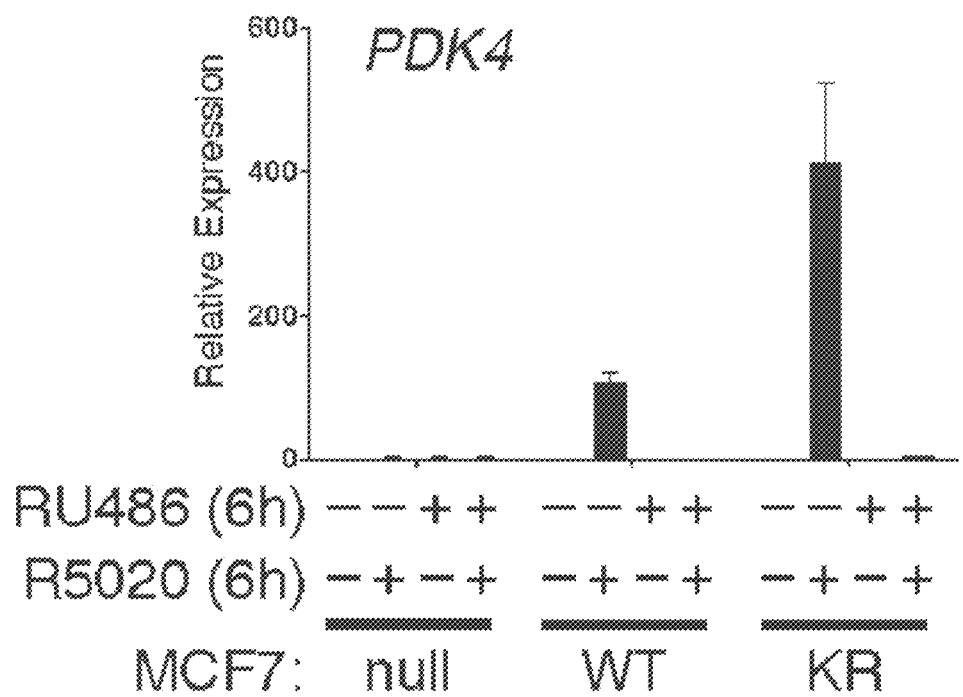
Fig. 2B4

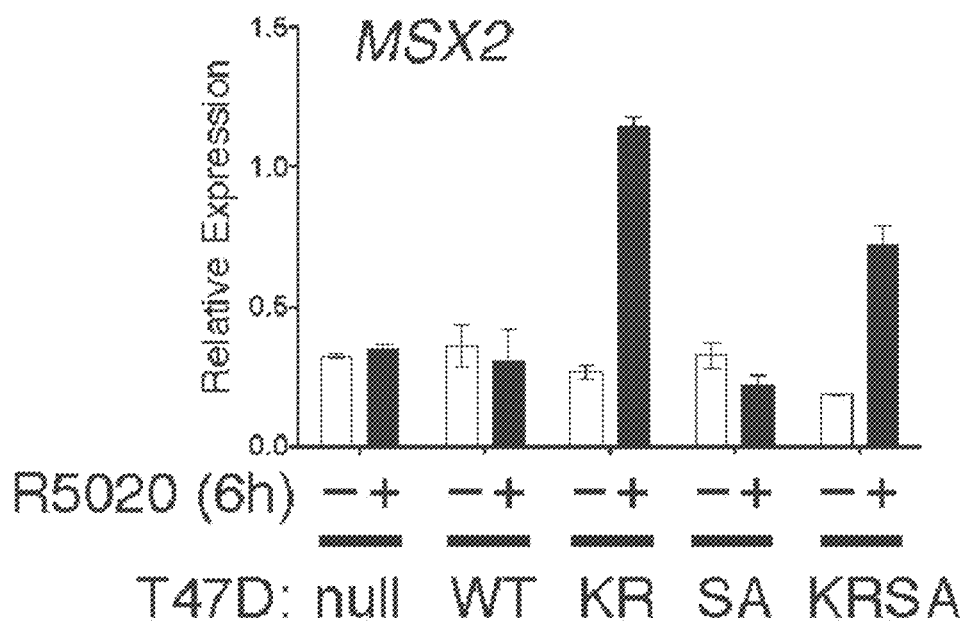
Fig.2C1
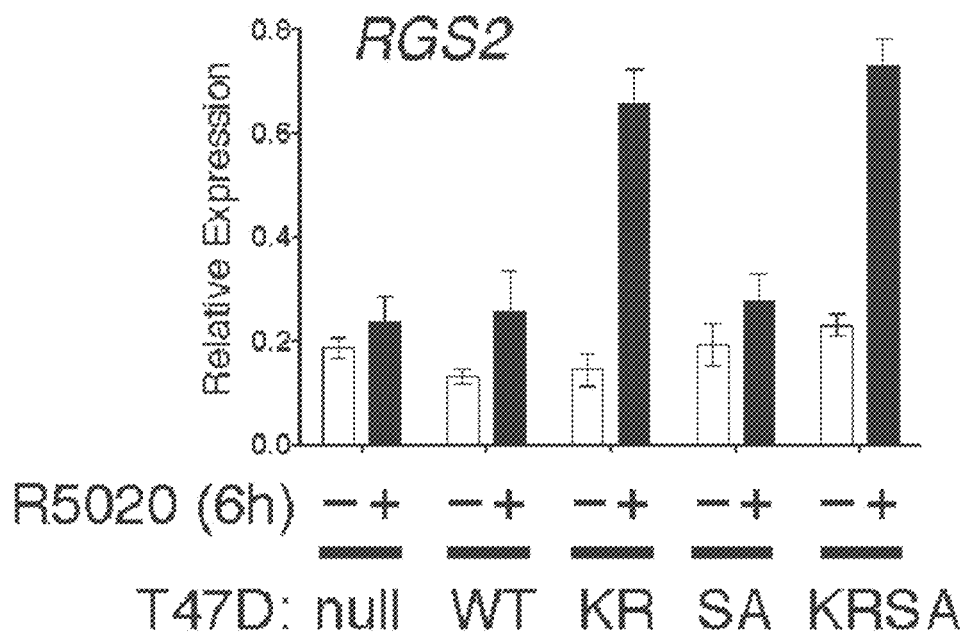
Fig.2C2

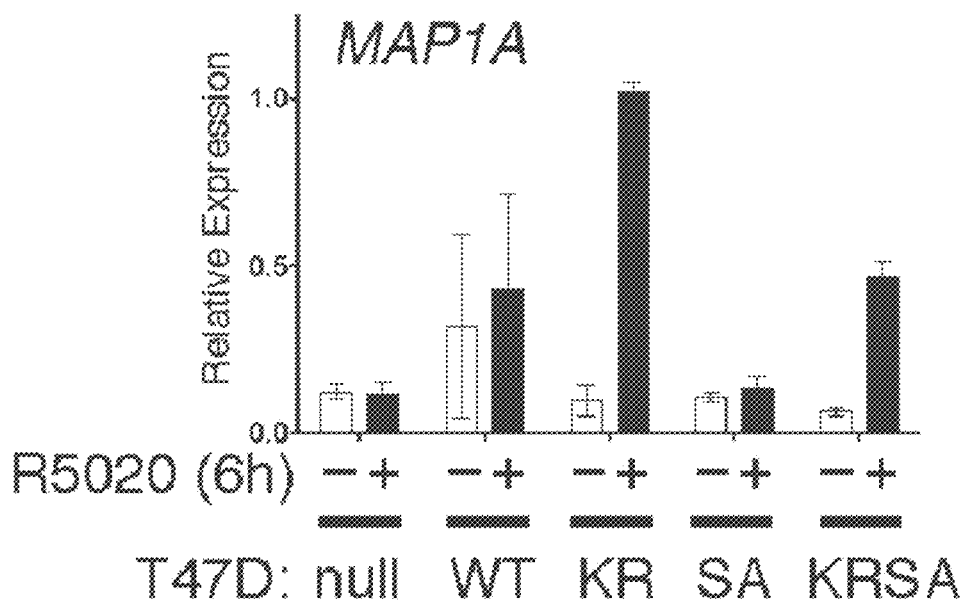
Fig. 2C3
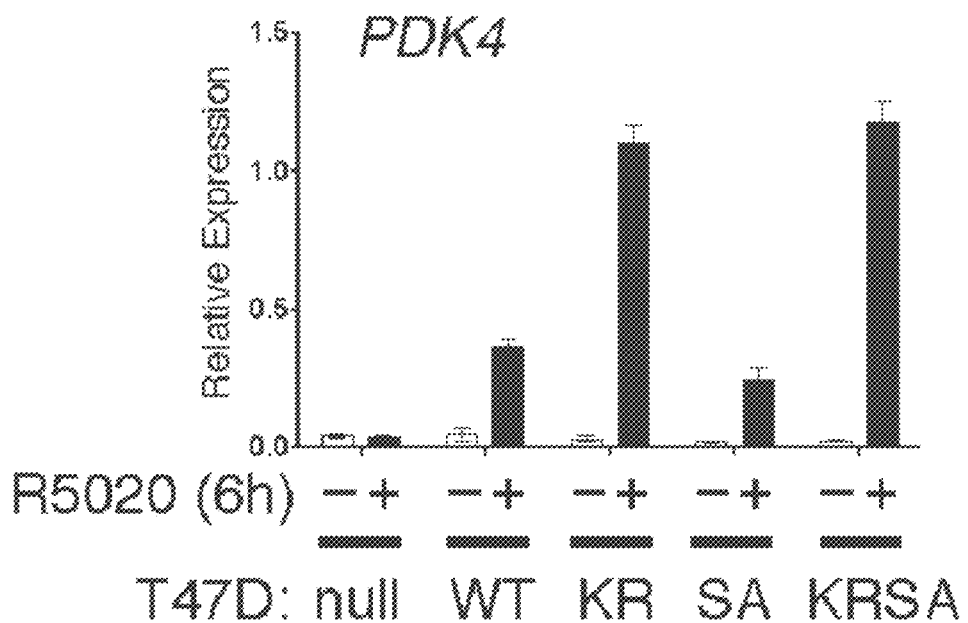
Fig. 2C4

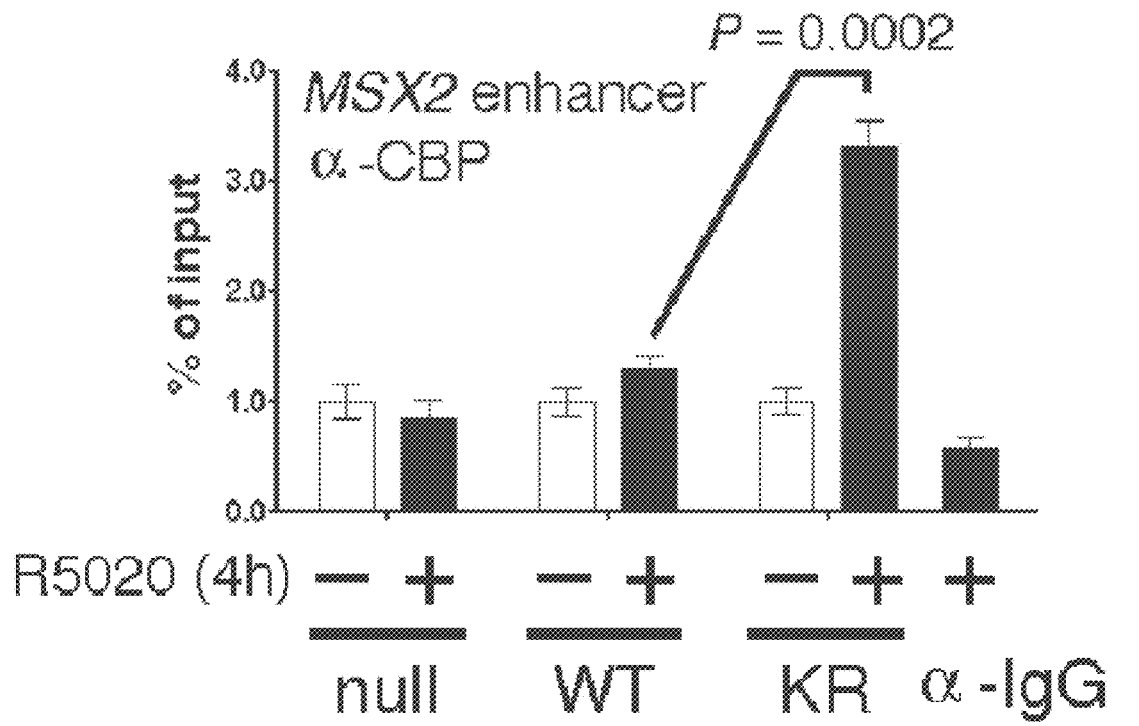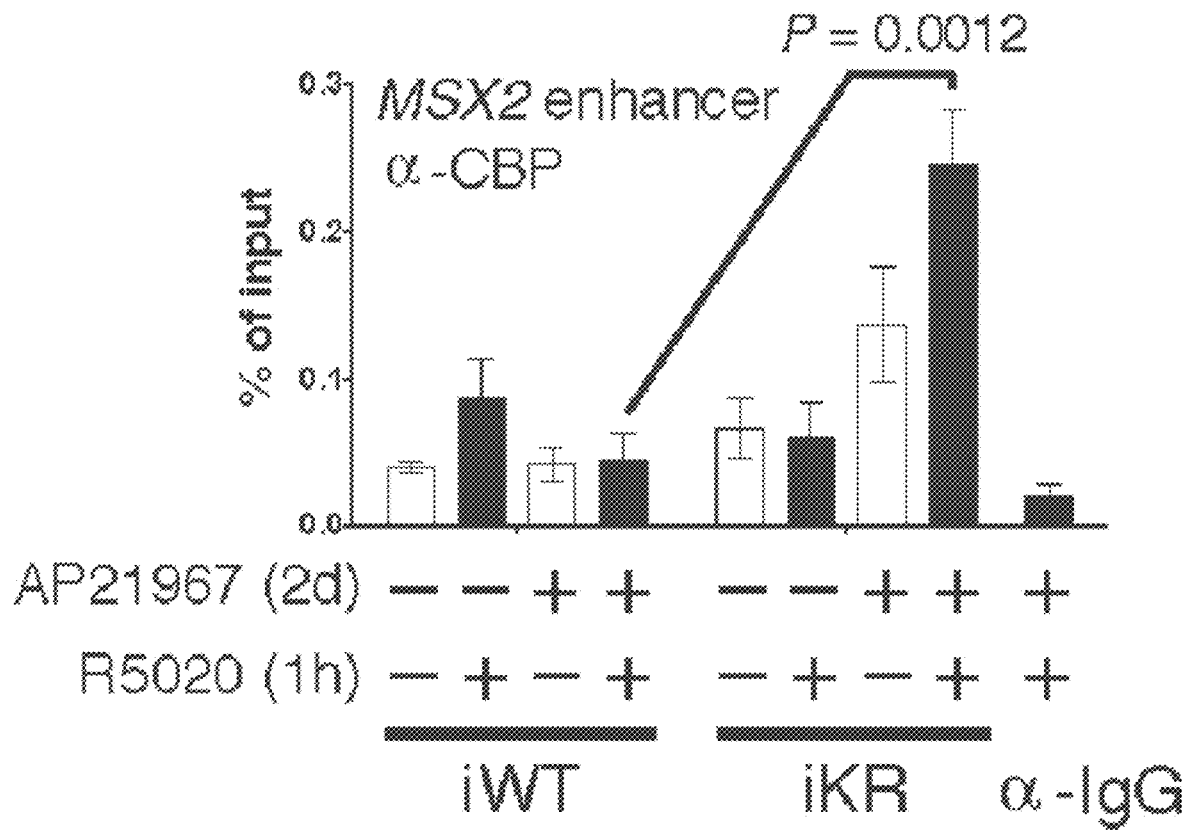
Fig. 3C

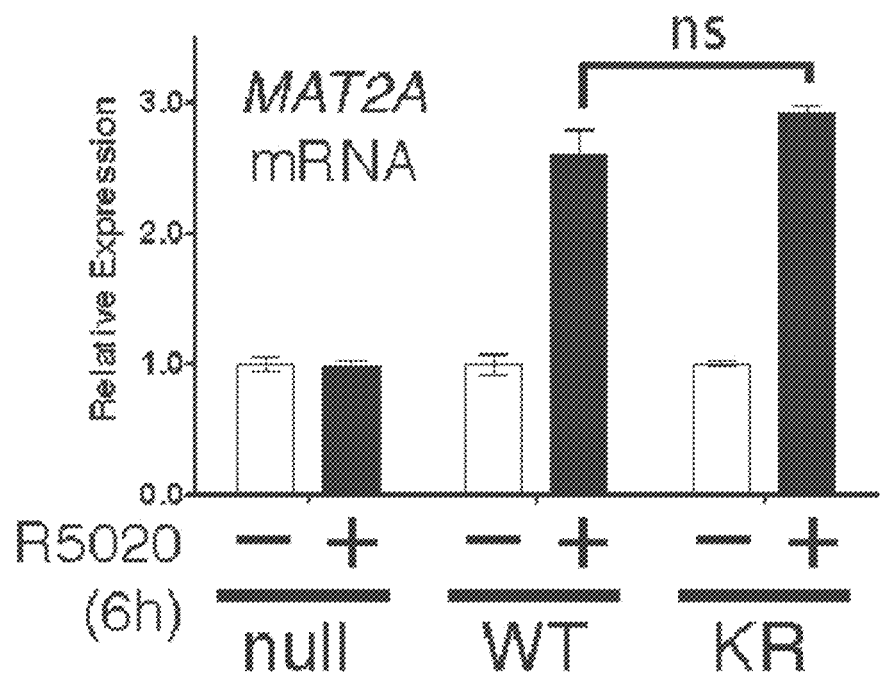
Fig. 3F1
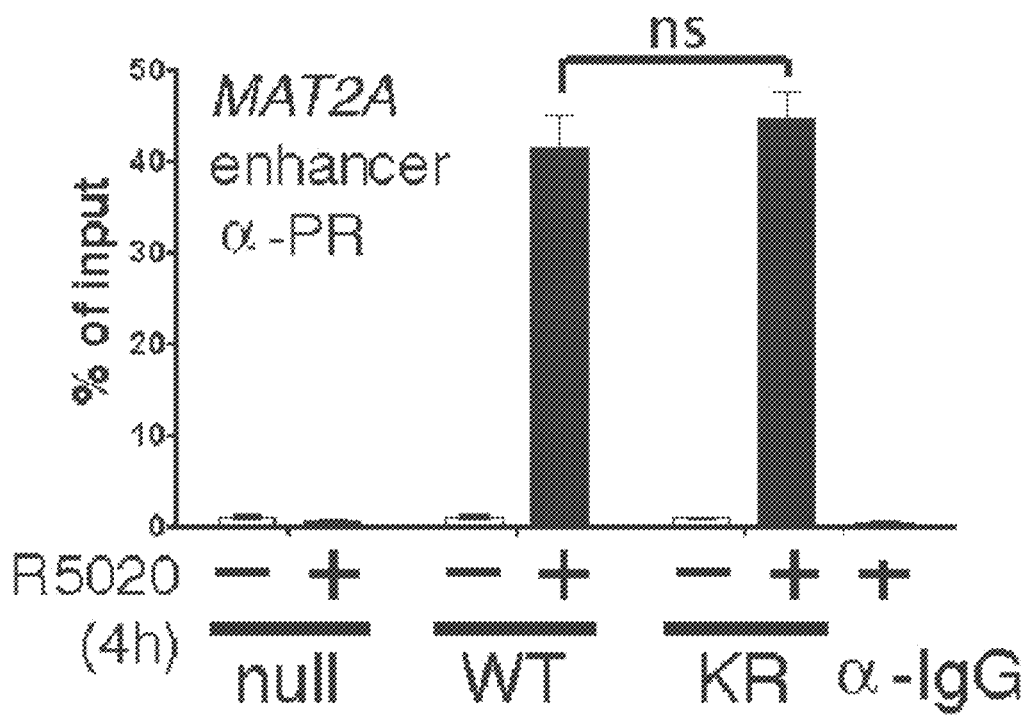
Fig. 3F2

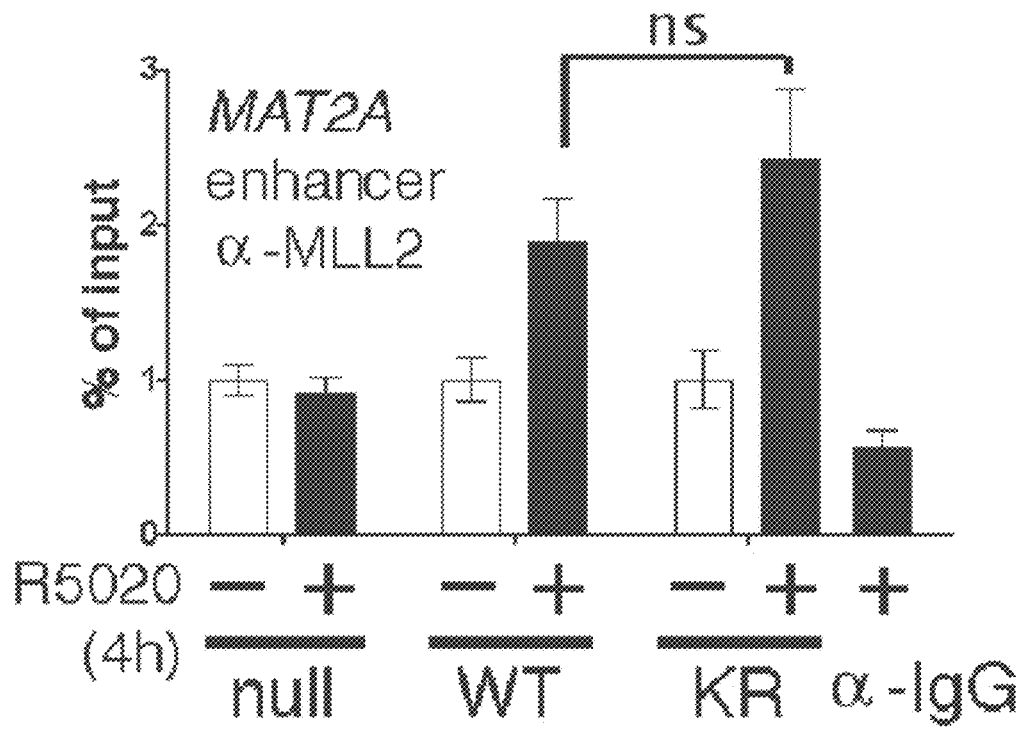
Fig. 3F3
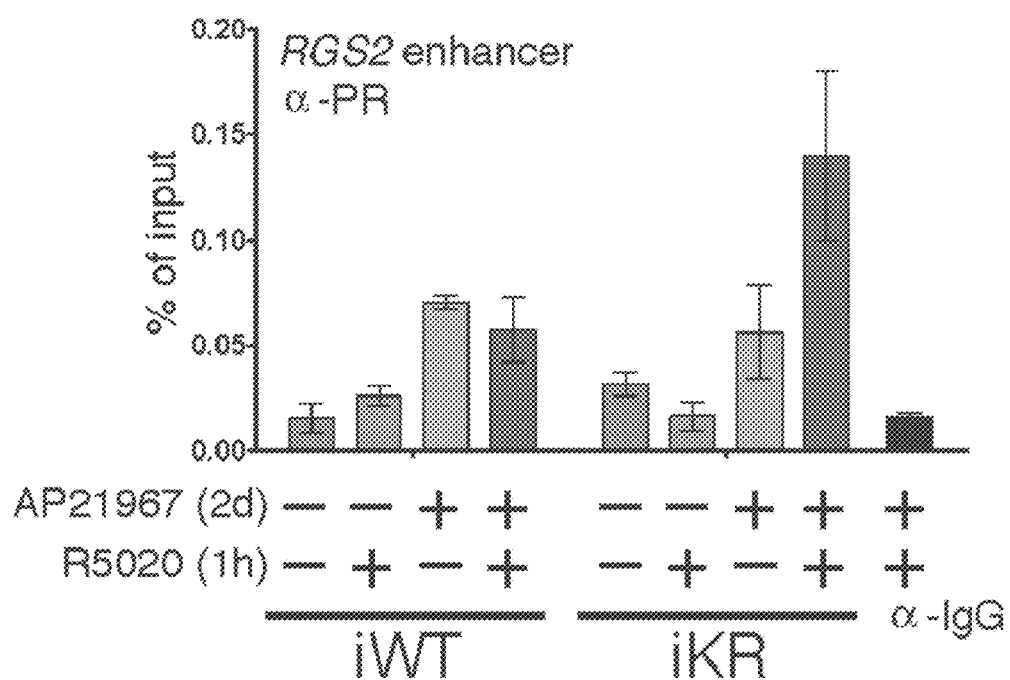
Fig. 3.1A1

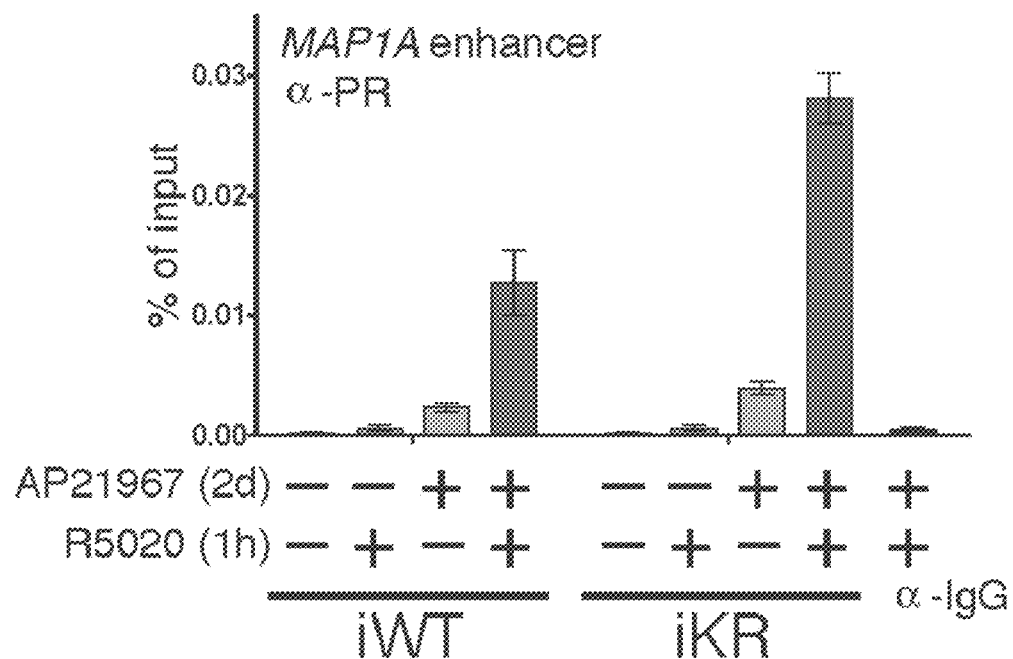
*Fig.3.1A2*
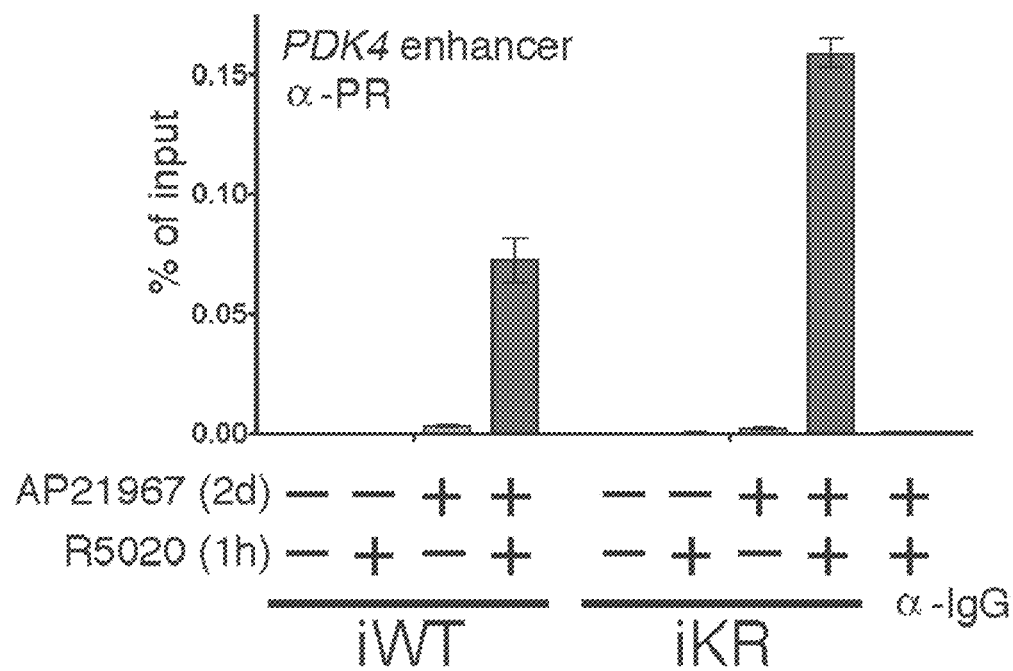
*Fig.3.1A3*

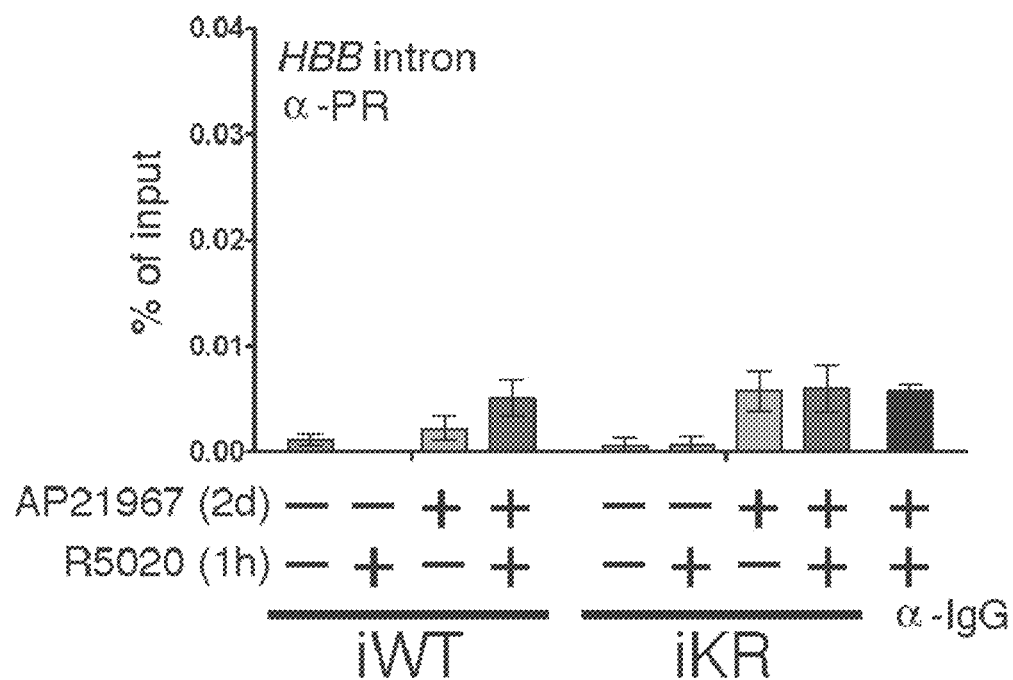
*Fig. 3.1A4*
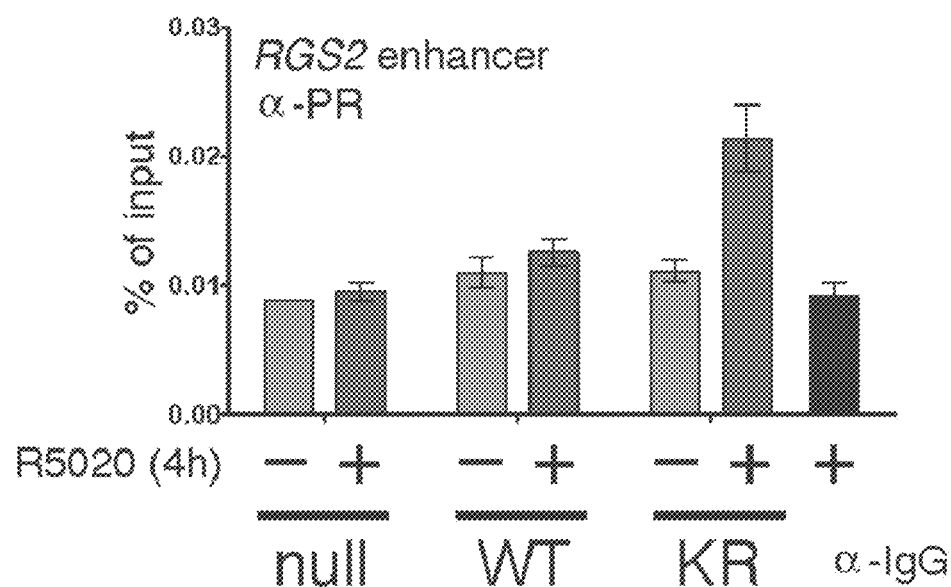
*Fig. 3.1B*

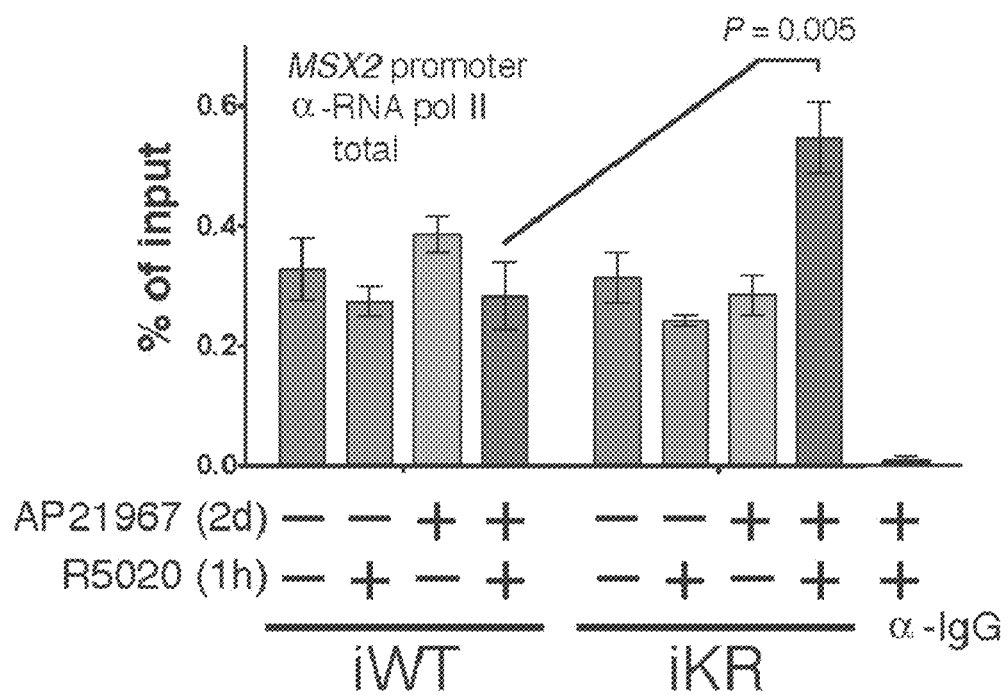
Fig. 3.2A
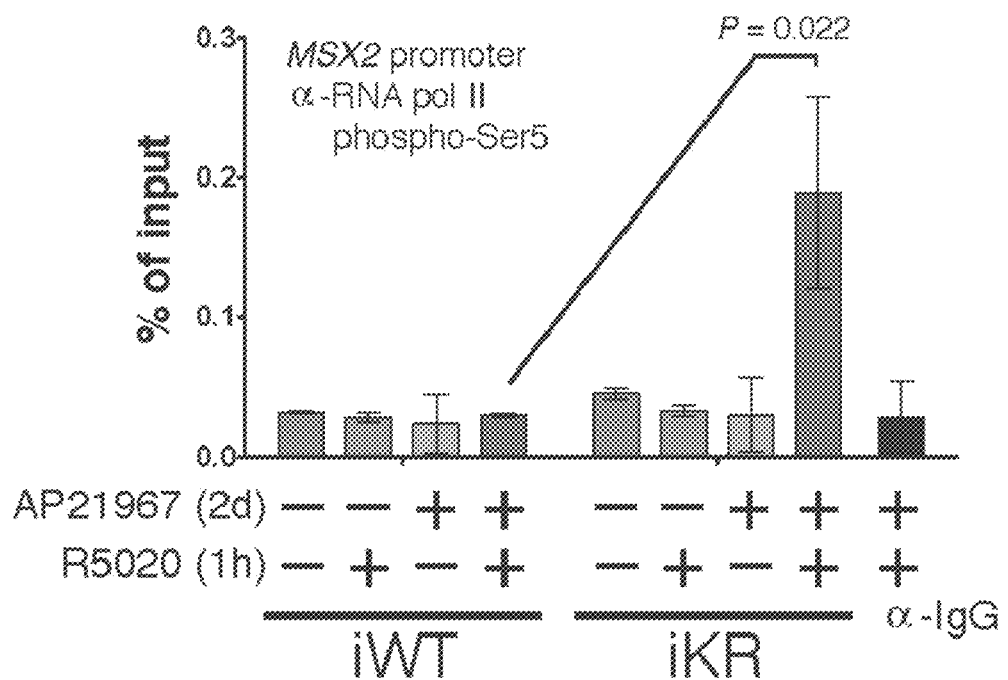
Fig. 3.2B

151 genes LD KR>WT

| Probe ID | Gene Name |
|---|---|
| ILMN_1737850 | DIO2 |
| ILMN_1753648 | SPRYD5 |
| ILMN_1697543 | SPINK5L3 |
| ILMN_1721626 | ARID5B |
| ILMN_1730995 | AFAP1L2 |
| ILMN_1701558 | MAP1A |
| ILMN_1811014 | PGR |
| ILMN_1687978 | PHLDA1 |
| ILMN_1759513 | RND3 |
| ILMN_1683607 | CYP1A2 |
| ILMN_1779875 | THY1 |
| ILMN_1753502 | IGSF11 |
| ILMN_2121409 | HBEGF |
| ILMN_1766951 | MSX2 |
| ILMN_2180232 | UTS2D |
| ILMN_1797161 | LOC93622 |
| ILMN_1706861 | RAB20 |
| ILMN_2197365 | RGS2 |
| ILMN_1693233 | KIAA0513 |
| ILMN_3305614 | ZNF812 |
| ILMN_1684982 | PDK4 |
| ILMN_2153637 | SCNN1G |
| ILMN_1743373 | DLL1 |
| ILMN_1791569 | PLXNA1 |
| ILMN_1762207 | SGSM1 |
| ILMN_1691798 | ZNF26 |
| ILMN_1769201 | ELF3 |
| ILMN_1786041 | ASB9 |

| Probe ID | Gene Name |
|---|---|
| ILMN_1760087 | SLC26A3 |
| ILMN_1809931 | NDRG1 |
| ILMN_3235379 | LOC100134265 |
| ILMN_2389666 | CR2 |
| ILMN_3232519 | LOC100129129 |
| ILMN_1813270 | ELF5 |
| ILMN_1799642 | TRIM24 |
| ILMN_1703955 | FBXO32 |
| ILMN_2201413 | SLC37A2 |
| ILMN_1713744 | C14orf132 |
| ILMN_1712894 | FUT1 |
| ILMN_1731648 | FOXJ2 |
| ILMN_1656938 | LOC731486 |
| ILMN_1780598 | PIAS1 |
| ILMN_1699676 | C14orf147 |
| ILMN_1758404 | TFAP2B |
| ILMN_2094856 | RANBP3L |
| ILMN_2168204 | ATG12 |
| ILMN_2376953 | KCNK2 |
| ILMN_1681515 | CRLF1 |
| ILMN_2406656 | GATA3 |
| ILMN_2228463 | DDC |
| ILMN_1720158 | ETS2 |
| ILMN_2073732 | CBLL1 |
| ILMN_1710209 | MFSD6 |
| ILMN_1807201 | FAM104A |
| ILMN_1765686 | LOC642352 |
| ILMN_1761093 | B3GAT1 |

| (A) | | (B) | |
|---|---|---|---|
| ILMN_1775708 | SLC2A3 | ILMN_1803811 | TRIB1 |
| ILMN_1692177 | TSC22D1 | ILMN_1754600 | FNBP1L |
| ILMN_3287125 | LOC340970 | ILMN_1775380 | SMOX |
| ILMN_1668822 | BATF | ILMN_1738491 | SNX30 |
| ILMN_1758619 | SAG | ILMN_1701007 | PON3 |
| ILMN_2403237 | CHN2 | ILMN_1664440 | TP53BP1 |
| ILMN_1777853 | MBOAT2 | ILMN_1801504 | RUNX1 |
| ILMN_2131661 | SOCS2 | ILMN_1776516 | ITPKA |
| ILMN_1810274 | HOXB2 | ILMN_1680104 | SLC35C1 |
| ILMN_1681848 | LOC399939 | ILMN_2169089 | C18orf54 |
| ILMN_1716265 | PGM2L1 | ILMN_1749675 | LOC728715 |
| ILMN_3279169 | LOC100134006 | ILMN_1805330 | KLHL26 |
| ILMN_1710027 | PNMT | ILMN_2169490 | TDRD9 |
| ILMN_1691747 | KHDRBS3 | ILMN_1732410 | SLC16A9 |
| ILMN_1766534 | BHLHB2 | ILMN_2329914 | SPRY1 |
| ILMN_1802205 | RHOB | ILMN_2405254 | GRB7 |
| ILMN_1795930 | PTGER4 | ILMN_1811364 | SGPP2 |
| ILMN_1713124 | AKR1C3 | ILMN_1736015 | PHF17 |
| ILMN_1766650 | FOXA1 | ILMN_1772137 | LOC650577 |
| ILMN_1661589 | DDIT4 | ILMN_1764629 | SLC39A14 |
| ILMN_1748840 | CALB2 | ILMN_2364272 | MBNL2 |
| ILMN_1652464 | TUBA3E | ILMN_1671554 | LPIN1 |
| ILMN_2305407 | ZBTB16 | ILMN_1752510 | FAM13A |
| ILMN_1762021 | TRIM48 | ILMN_1763228 | MEF2D |
| ILMN_1656951 | APCDD1 | ILMN_1745034 | SLC11A2 |
| ILMN_2388800 | PPAP2B | ILMN_1682015 | GAL |
| ILMN_1700967 | C3orf59 | ILMN_1657679 | VAV3 |
| ILMN_3202863 | LOC440040 | ILMN_1776523 | KLF9 |
| ILMN_1724832 | OVOL2 | ILMN_1697448 | TXNIP |
| ILMN_3229324 | SGK1 | ILMN_3229748 | TRIM53 |
| ILMN_1781514 | PCDH17 | ILMN_1674193 | EMX1 |

| | |
|---|---|
| ILMN_1661994 | ESRRG |
| ILMN_1653496 | GLUL |
| ILMN_2386179 | ZMYND8 |
| ILMN_2275098 | DTX2 |
| ILMN_1770635 | SOX2 |
| ILMN_2095759 | OGFRL1 |
| ILMN_1672403 | ADAMTS8 |
| ILMN_1754114 | FLJ20021 |
| ILMN_2132982 | IGFBP5 |
| ILMN_1672004 | TOB1 |
| ILMN_1657571 | ASNA1 |
| ILMN_1702487 | SGK |
| ILMN_1791447 | CXCL12 |
| ILMN_1661755 | FAM129B |
| ILMN_1734833 | NBN |
| ILMN_2215639 | TUBA3D |

Ⓓ

| | |
|---|---|
| ILMN_1732071 | HIST2H2BE |
| ILMN_1734366 | PORC |
| ILMN_1811272 | GPR81 |
| ILMN_1703531 | S1PR3 |
| ILMN_1765574 | TFAP2A |
| ILMN_1736093 | SNX33 |
| ILMN_3236045 | SPINT3 |
| ILMN_1781400 | SLC7A2 |
| ILMN_1715664 | NHS |
| ILMN_1667295 | VASN |
| ILMN_1670672 | TMEM37 |
| ILMN_1664176 | FBLN5 |
| ILMN_1769400 | FOXD2 |
| ILMN_1657115 | TMEM61 |
| ILMN_1706798 | EAF2 |
| ILMN_1764850 | HPCAL1 |
| ILMN_1771728 | PXMP4 |

*Fig. 4.1A3*

92 genes LI KR>WT

| Probe ID | Gene Name | Probe ID | Gene Name |
|---|---|---|---|
| ILMN_2173592 | BCHE | ILMN_1724734 | UCC9 |
| ILMN_1791270 | CDH10 | ILMN_1879895 | MPP6 |
| ILMN_1706176 | GNAT3 | ILMN_1700357 | C4orf33 |
| ILMN_1801564 | CXCR4 | ILMN_2086329 | SPRY2 |
| ILMN_2189027 | LPO | ILMN_1578757 | BCYRN1 |
| ILMN_1805666 | PLAT3 | ILMN_1713124 | AKR1C3 |
| ILMN_2380367 | DNASE1L3 | ILMN_1851838 | PND1 |
| ILMN_3966042 | VCX3A | ILMN_1810835 | SPRR3 |
| ILMN_2340259 | PDE4B | ILMN_1794482 | HOXC8 |
| ILMN_1804277 | SPRED1 | ILMN_1810127 | ZNF789 |
| ILMN_2316236 | HOPX | ILMN_1794875 | AGPAT9 |
| ILMN_1684836 | VCX | ILMN_2166439 | ITGAV |
| ILMN_1678133 | SERPINB1 | ILMN_1796765 | ITGB5 |
| ILMN_1779241 | CRYM | ILMN_3265742 | LOC100130835 |
| ILMN_2186716 | VCX-C | ILMN_1796359 | PLEKHA2 |
| ILMN_1670870 | ALDAM | ILMN_1757020 | CDH6 |
| ILMN_3303614 | ZNF12 | | |
| ILMN_1704154 | TNFRSF19 | | |
| ILMN_1867199 | LOC440349 | | |
| ILMN_2396020 | DUSP6 | | |
| ILMN_3236667 | GAGE12D | | |
| ILMN_1713006 | ABCC11 | | |
| ILMN_2297766 | KCNMA1 | | |
| ILMN_2374159 | HERPUD1 | | |
| ILMN_1731433 | ABP1 | | |
| ILMN_1674620 | SGCE | | |
| ILMN_1672350 | JAM3 | | |
| ILMN_2394257 | ATP6V0A4 | | |

 

*Fig. 4.1B1*

| | |
|---|---|
| ILMN_2104436 | GAGE6 |
| ILMN_1702652 | EFNB2 |
| ILMN_2364857 | DHRS2 |
| ILMN_2140510 | KLHL13 |
| ILMN_1738236 | L1CAM |
| ILMN_1713496 | ST3GAL5 |
| ILMN_1785410 | ATP2C2 |
| ILMN_2178087 | ANKRD6 |
| ILMN_1739521 | NLGN1 |
| ILMN_1743323 | CXCL14 |
| ILMN_3251587 | LOC100038569 |
| ILMN_1734696 | CLDN1 |
| ILMN_1720511 | LRRN1 |
| ILMN_1772561 | RAP2C |
| ILMN_1763312 | PLXDC2 |
| ILMN_1798523 | ABCA3 |
| ILMN_1760170 | APOO |
| ILMN_1696856 | CST6 |
| ILMN_1796349 | SMPDL3A |
| ILMN_1801216 | S100P |
| ILMN_1825702 | ACOX2 |
| ILMN_1788054 | ABCA1 |
| ILMN_1774110 | CHN2 |
| ILMN_1808508 | KITLG |
| ILMN_1761941 | C4orf18 |
| ILMN_1706257 | DSCR8 |
| ILMN_1758918 | SCRL1 |
| ILMN_2230016 | HIGD1A |
| ILMN_1677807 | SC5DL |
| ILMN_1678616 | GREM2 |
| ILMN_2178302 | PNDC3B |

*Fig. 4.1B2*

| G | |
|---|---|
| ILMN_1738712 | GPR180 |
| ILMN_1770467 | GAGE7 |
| ILMN_1801443 | TSKU |
| ILMN_3242920 | GAGE12F |
| ILMN_1735157 | GALNT13 |
| ILMN_1741422 | FUT8 |
| ILMN_1706015 | FAM43A |
| ILMN_3197757 | LOC645691 |
| ILMN_2235101 | LOC100132985 |
| ILMN_2136133 | PABPC1 |
| ILMN_3269859 | LOC646546 |
| ILMN_2137786 | KLF4 |
| ILMN_1742460 | PCDH11X |
| ILMN_1730351 | FLJ35767 |
| ILMN_3235221 | LOC644936 |
| ILMN_3241021 | RNY4 |
| ILMN_1754664 | SLC35A16 |

*Fig. 4.1B3*

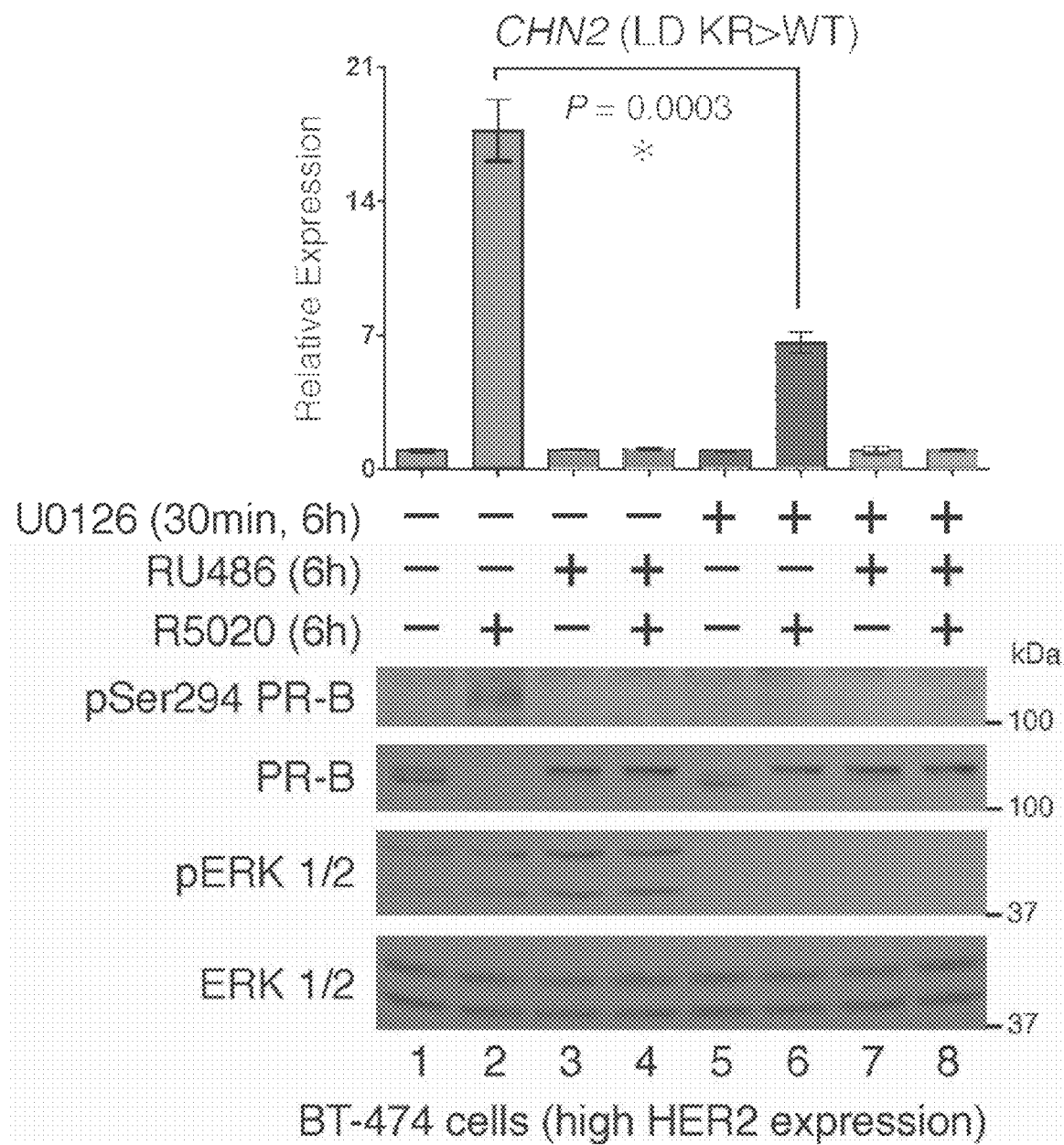
Fig.5B1

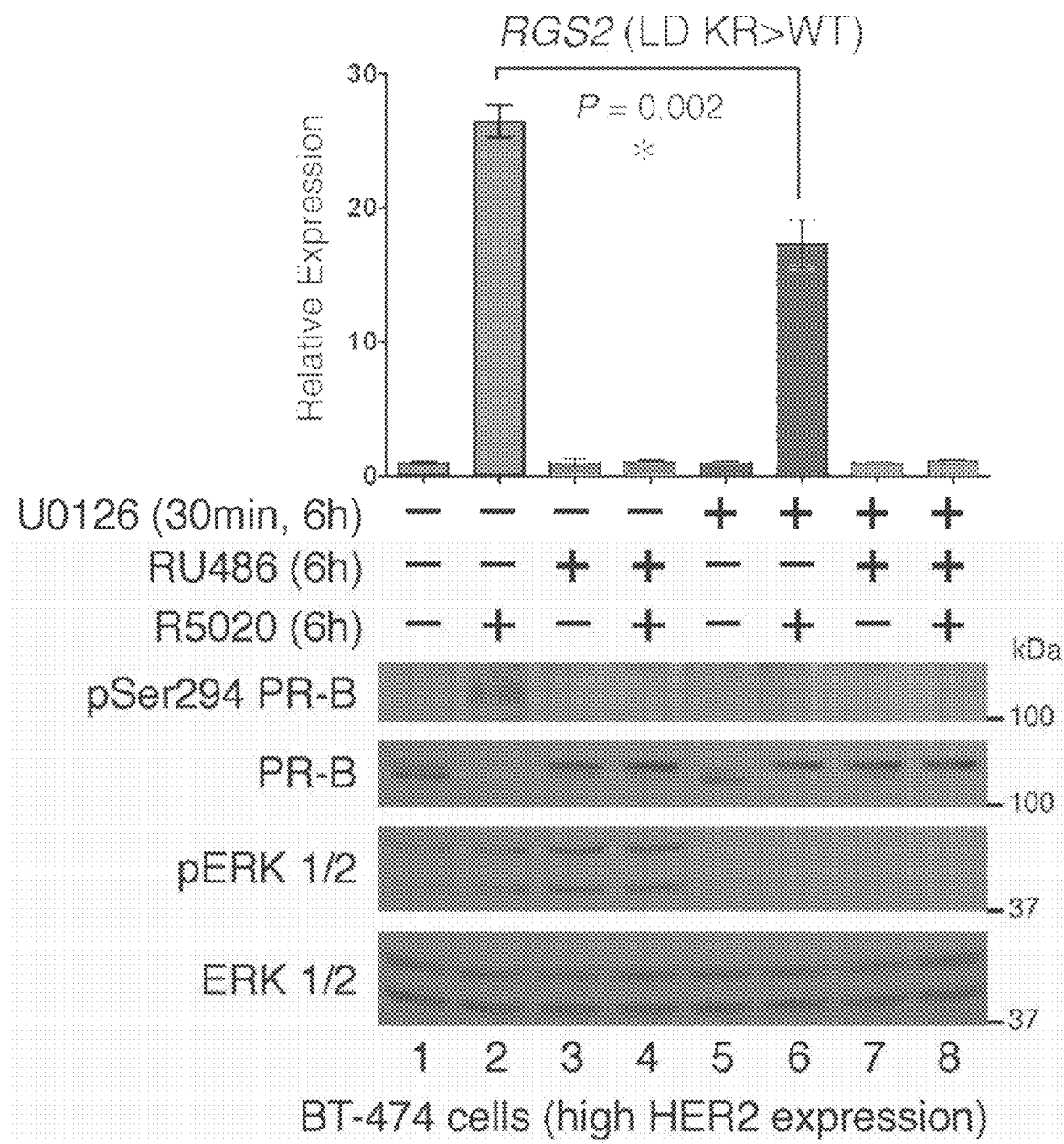
Fig.5B2

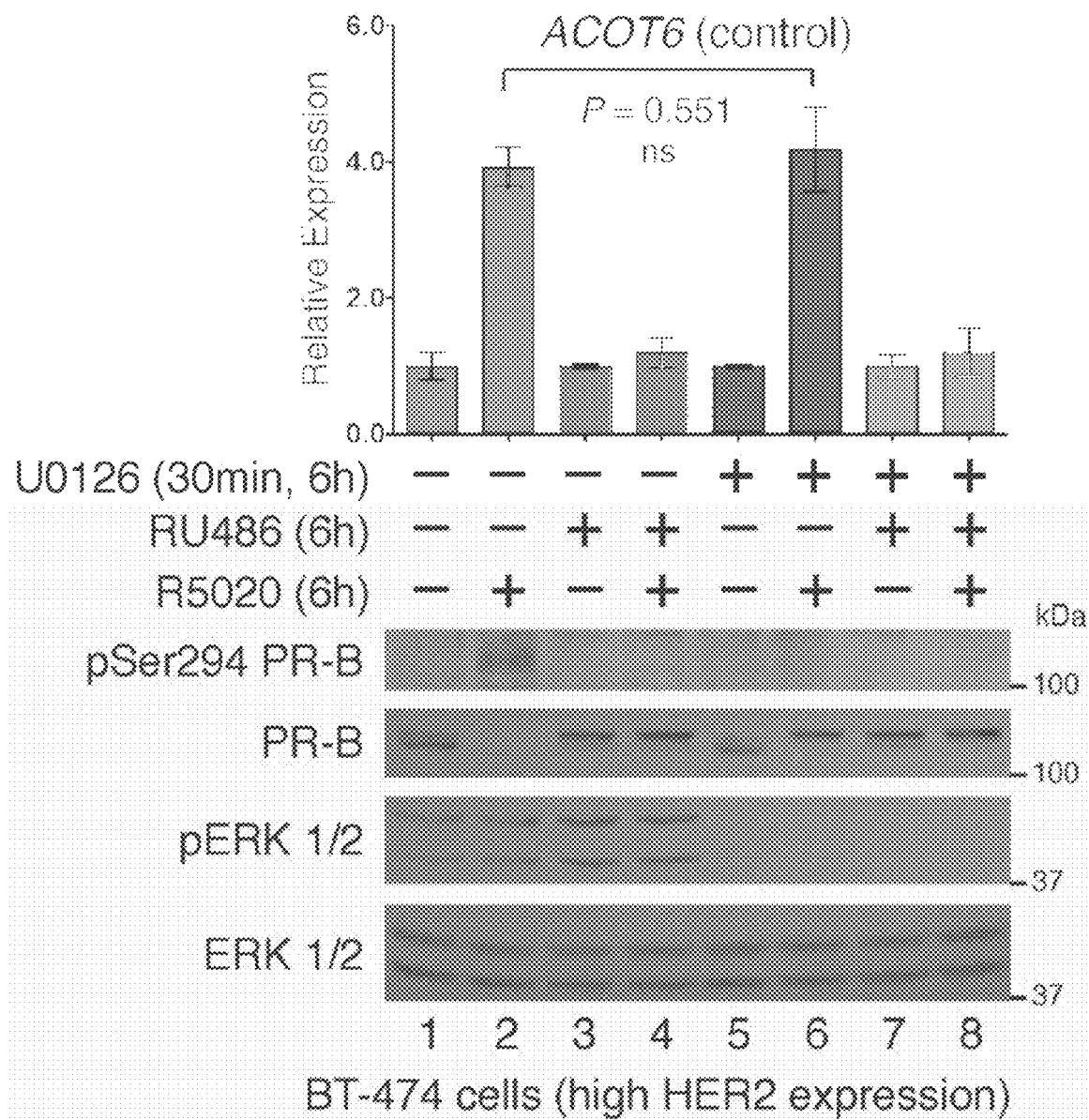
Fig. 5B3

| Antibody Name | Vendor | Catalog Number |
|---|---|---|
| PR | NeoMarkers | Ab-8 |
| phospho-Ser294 PR | Dean Edwards, PhD (Baylor, Houston, TX) | Clemm et al. (2000) Mol Endocrinol 14: 52-65 |
| CBP | Santa Cruz Biotechnology | A-22, sc-369 |
| MLL2 | Santa Cruz Biotechnology | I-18, sc-68671 |
| H3K4me2 | Active Motif | 39141 |
| Beta-Actin | Sigma | a4700 |
| ERK1/2 | Cell Signaling | 9102 |
| phospho-ERK1/2 | Cell Signaling | 9101 |
| PARP | Cell Signaling | 9541 |

Fig. 5.1A

| Primer Name | Sequence (5' to 3') | Application |
|---|---|---|
| ABCA3-RTPCR-F | CTGTCTTTCATCCTTCCCAGAG | RT-PCR |
| ABCA3-RTPCR-R | TCTTTCTGCTTCTTCTCCAGTTTAG | RT-PCR |
| ACOT6-RTPCR-F | GGCTTATTTCAGATTTGAAGACCTC | RT-PCR |
| ACOT6-RTPCR-R | AGAAGCGCAATACTAGGACCTTTC | RT-PCR |
| BCHE-RTPCR-F | TGCTCAACAATGTCGATTCTG | RT-PCR |
| BCHE-RTPCR-R | TTCCACTCCATTCTGCTTC | RT-PCR |
| BCL2L11-RTPCR-F | GTCTGACTCTGACTCTCGGACTG | RT-PCR |
| BCL2L11-RTPCR-R | GAACTTACATCAGAAGGTTGCTTTG | RT-PCR |
| CHN2-RTPCR-F | ACCAGCCTCCTATATGGAAATC | RT-PCR |
| CHN2-RTPCR-R | CTCCCGAGGACAAATGATTC | RT-PCR |
| DNALI1-RTPCR-F | AGAAGAAGCACAATGAGGAGATTC | RT-PCR |
| DNALI1-RTPCR-R | CATGTGGAAATTATCACTTCTTTGG | RT-PCR |
| GAPDH-RTPCR-F | GCCAAAAGGGTCATCATCTCTGCC | RT-PCR |
| GAPDH-RTPCR-R | TGGTGGTGCAGGAGGCATTG | RT-PCR |
| MAP1A-RTPCR-F | TGCTGGATGCCCTGCTGGAG | RT-PCR |
| MAP1A-RTPCR-R | ACCACTCACGAGTCACCTCCG | RT-PCR |
| MAT2A-RTPCR-F | AAATCCCTTGTTAAAGGAGGTCTG | RT-PCR |
| MAT2A-RTPCR-R | CTGAGAGGTACCATAATGGAAAATG | RT-PCR |
| MSX2-RTPCR-F | AGCGGCGTGGATGCAGGAAC | RT-PCR |
| MSX2-RTPCR-R | TGCGCGGCTTCCGATTGGTC | RT-PCR |
| PDK4-RTPCR-F | CATACTCCACTGCACCAACG | RT-PCR |
| PDK4-RTPCR-R | AGAAATTGGCAAGCCGTAAC | RT-PCR |
| RAC2-RTPCR-F | TCTCATCAGCTACACCACCAAC | RT-PCR |
| RAC2-RTPCR-R | ACATTGGCTGAATAGTTGTCAAAC | RT-PCR |
| RGS2-RTPCR-F | AGCTGTCCTCAAAAGCAAGG | RT-PCR |
| RGS2-RTPCR-R | TCTGGGCAATCAGAGTTTTG | RT-PCR |
| SULF1-RTPCR-F | CCGATGATCAAGATGTGGAG | RT-PCR |
| SULF1-RTPCR-R | CAAAGGCATTGATGAAGGTG | RT-PCR |
| P2RY6-RTPCR-F | ATAACAAGACCTCTGCCAGAAGAAC | RT-PCR |
| P2RY6-RTPCR-R | CAGGTGGGTTTCCTATGTTCAG | RT-PCR |
| PARP4-RTPCR-F | AGAAGATGTAGACTTCCTGCCCTAC | RT-PCR |
| PARP4-RTPCR-R | TTTCGTTTGGATAAACGTAATTCTG | RT-PCR |

*Fig. 5.1B*

| Primer Name | Sequence (5' to 3') | Application |
|---|---|---|
| HBB-ChIP-F | TCCAACTCCTAAGCCAGTGC | ChIP |
| HBB-ChIP-R | TGCTCCTGGGAGTAGATTGG | ChIP |
| MAP1A-ChIP-F | GCAAGCAACTGCTATCTTC | ChIP |
| MAP1A-ChIP-R | CTGGGAGTGCTCTGGAAGG | ChIP |
| MAT2A-ChIP-F | GTTCCCTGAGAACCTCATTAAACC | ChIP |
| MAT2A-ChIP-R | GGTCTCTGCAGCCTGTTCTG | ChIP |
| MSX2-ChIP-101-enhancer-F | CACATTCTGTCTGACTCTGAAGG | ChIP |
| MSX2-ChIP-101-enhancer-R | CCACATTTGCTAGCTTATTAGTTCTG | ChIP |
| MSX2-ChIP-102-enhancer-F | GACGTCCAGATCAGAACTAATAAGC | ChIP |
| MSX2-ChIP-102-enhancer-R | CTGACTTTGACAATAGTCCTCAAG | ChIP |
| MSX2-ChIP-103-enhancer-F | CTTGAGGACTATTGTCAAAGTCAG | ChIP |
| MSX2-ChIP-103-enhancer-R | CAAGCTCATGGACATCAAATAGAAG | ChIP |
| MSX2-ChIP-104-enhancer-F | ATTCTTCTATTGATGTCCATGAGC | ChIP |
| MSX2-ChIP-104-enhancer-R | TCAGACCCAGTCACTACACATTCTAC | ChIP |
| MSX2-ChIP-105-enhancer-F | CATGCCAAGAGTAGAAATGTTAGTG | ChIP |
| MSX2-ChIP-105-enhancer-R | AAATGTCCAGAGATACAGAATATGGTAAG | ChIP |
| MSX2-ChIP-106-enhancer-F | GGATCCATTGTCCATACAGAAACTTAC | ChIP |
| MSX2-ChIP-106-enhancer-R | AGAGATTGCCATGGAATACAGGAC | ChIP |
| MSX2-ChIP-107-enhancer-F | GTACTGATGGCAATCTCTGGTTC | ChIP |
| MSX2-ChIP-107-enhancer-R | ATCATTTTGTTCTGAAGGATTTCTC | ChIP |

| Name | Sequence | Type |
|---|---|---|
| MSX2-ChIP-108-enhancer-F | AAATCCTTCAGAACAAAATGATCC | ChIP |
| MSX2-ChIP-108-enhancer-R | TAATCTTCTGGCTCTATCCTTCTCC | ChIP |
| MSX2-ChIP-109-enhancer-F | GTACTGGTTGAGGAGAAGGATAGAG | ChIP |
| MSX2-ChIP-109-enhancer-R | GAGTTTGGAATTCTATTAATGCTC | ChIP |
| MSX2-ChIP-110-enhancer-F | AAACTCAGTATCAGAGCCTGTC | ChIP |
| MSX2-ChIP-110-enhancer-R | CACTGATTTGCTTTCTAACCGATAC | ChIP |
| MSX2-ChIP-111-enhancer-F | TACTGCTGCTCTTCTAACACATG | ChIP |
| MSX2-ChIP-111-enhancer-R | CACAAGGCAACTGGATAATTAACTG | ChIP |
| MSX2-ChIP-112-enhancer-F | TTAATTATCCAGTTGCTTGTGAAG | ChIP |
| MSX2-ChIP-112-enhancer-R | AGAGAGGGCAGACAGATGTAC | ChIP |
| MSX2-ChIP-enhancerPRE-F | TGGCCATTTAAGGGCTGAG | ChIP |
| MSX2-ChIP-enhancerPRE-R | GACTCTGTGGAAGCTGAAG | ChIP |
| MSX2-ChIP-proximal-promoter-F | GCATACATTTCTTTACCAGTTCCAGGATAC | ChIP |
| MSX2-ChIP-proximal-promoter-R | TGGCTTACTTTACCAGTTCTTTCTC | ChIP |
| PDK4 ChIP-F | GGGAGCCCATAGTTCTTCTC | ChIP |
| PDK4 ChIP-R | TTATTTGTCTCCCGCACTC | ChIP |
| RGS2 ChIP-F | AACAAATAAAACTTAATCAAGGAAACTG | ChIP |
| RGS2 ChIP-R | TTTGTTGAGTTAGGATTAGGAGAAC | ChIP |

BREAST CANCER PROGNOSIS

CROSS-REFERENCE TO RELATED APPLICATIONS

This application claims priority from U.S. Provisional Application No. 61/639,407, filed Apr. 27, 2012, the entire disclosure of which is herein incorporated by reference.

STATEMENT OF GOVERNMENT RIGHTS

This invention was made with the assistance of government support under United States Grant No. CA1159712-01 from the National Institutes of Health. The government has certain rights in the invention.

BACKGROUND OF THE INVENTION

Current mRNA (e.g., gene expression based) prognostic breast cancer screening tests (such as Oncotype DX) assay for expression of a limited number of unrelated genes, each known to be involved in breast cancer progression. Because breast cancer is a very heterogeneous disease, these tests fail to select those patients who are most likely to benefit from a given targeted therapy, including a rapidly growing list of existing and new drugs. Thus, health care providers are forced to try random combinations of available drugs in hopes that these combination treatments will provide a clinical response or clinical benefit. These strategies also fail to link expression of any collection of gene expression data to any defined mechanism(s) responsible for their expression (i.e., the targets are unknown).

SUMMARY OF THE INVENTION

Progesterone receptors are emerging as important drivers of breast cancer progression. Progestin treatment (as part of hormone replacement therapy in combination with estrogen) in post-menopausal women significantly increases their breast cancer risk. Recent studies suggest that estrogen-only supplementation may in fact protect women from breast cancer. Herein, one exemplary mechanism responsible for progestin action is described: activated deSUMOylated phospho-progesterone receptor transcription. In one aspect, a unique gene signature is defined that could be used to identify breast cancer patients whose tumors are primarily progesterone receptor (PR) driven and thus likely to be susceptible to anti-estrogen (e.g., tamoxifen), anti-progestin, or aromatase inhibitor therapy. In another aspect, a PR gene signature is used to identify a population of women who are appropriate candidates for therapies that include an antiprogestin.

An important question pertinent to anti-progestin treatment is how to identify activated PRs that are relevant clinical therapeutic targets. In one aspect, the present exemplary methods are aimed at characterizing PRs that are present in a functional (activated) state in the human tumor tissue routinely obtainable in the clinical setting. As antagonizing non-active PR with a specific anti-progestin is therapeutically pointless, the present exemplary methods provide new and critical information to guide treatment of patients with anti-progestins. Such predictive diagnostic tests provide (1) consistent methods to support therapeutic decision-making with respect to anti-progestins, (2) guide selection of individual patients and patient populations that are likely to respond to anti-progestin treatment, and (3) exclude those individual patients that are least likely to respond or benefit from an anti-progestin treatment.

Described herein are exemplary strategies and methods to identify genes that are upregulated by progesterone receptor (e.g., human PR isoform A and/or B) in cancer cells containing high kinase activities, for example, wherein PR-B can be phosphorylated (on Ser294) and/or deSUMOylated (on Lys388), thus creating a transcriptionally hyperactive (nuclear transcription factor) receptor. Prior understanding of PR transcriptional action was hindered by failure to consider the unique transcriptional activities of PR-B (relative to PR-A) that arise as a consequence of its specific interactions with protein kinase cascades. The strategies and methods described herein to identify endogenous genes specifically up or down-regulated by deSUMOylated (and likely phosphorylated) PR-B in cancer cells is the first of its kind.

Currently, at least half of all women with steroid hormone (SR) positive (luminal) breast cancers fail on endocrine therapy aimed at blocking estrogen production or estrogen receptor (ER) action. As part of a novel clinical screening (prognostic) protocol for patients with SR positive or luminal breast cancers (~70% of all breast cancer patients), expression of the deSUMOylated phospho-PR-driven gene signature can be used to identify patients whose tumors are highly likely to undergo PR-driven proliferation and progression to endocrine-resistance in response to available anti-estrogen and aromatase inhibitor treatment. Such patients would be candidates for endocrine therapy that contains an anti-progestin. Selective PR modulators exist, some of which are new, including, but not limited to, antiprogestins/selective PR modulators such as mifepristone (RU486), Lonaprisan (ZK-230211), Telapristone (Proellex or CDB-4124), onapristone (ZK-98299), asoprisnil, ulipristal acetate, aglepristone, ZM172406, ZM172405 and ZM150271.

The present invention provides gene expression profiles and methods for identifying those patients who are likely to respond to treatment with antiprogestins (these patients are referred to as "responders"), as well as those patients who are not likely to benefit from such treatment (these patients are referred to as "non-responders"). Aspects provided herein allow a treatment provider to identify those patients who are responders to treatment with antiprogestins, and those who are non-responders to such treatment, prior to administration of the agent.

The present invention further comprises gene expression profiles (also referred to as "gene signatures") that are indicative of the tendency of a patient afflicted with cancer to respond to treatment with an anti-progestin. The gene expression profile comprises at least one, and preferably a plurality, of genes selected from the group identified in Table 1a and 1b. This group of genes is referred to herein as the "Anti-progestin Responder Genes." According to aspects of the invention, some or all of theses genes are differentially expressed (e.g., up-regulated or down-regulated) in patients who are responders to anti-progestin therapy.

The present invention further comprises methods of determining if a patient with cancer is a responder or non-responder to treatment with an anti-progestin. In one aspect, the methods comprise obtaining a sample of the malignant tissue or cells (e.g., tumor sample, circulating tumor cells) from the patient, determining at least one gene expression profile of the sample, and determining from the at least one gene expression profile whether at least one gene selected from the Antiprogestin Responder Genes is over- or under-expressed in the sample by, for example, comparison to at least one gene expression profile from a control sample. From this information, the treatment provider can ascertain whether the patient is likely to benefit from anti-progestin therapy.

In another aspect, the present invention further comprises an assay for determining the gene expression profile in a patient's tissue sample, and instructions for using the assay.

One embodiment provides an assay for determining if a patient diagnosed with cancer is likely to respond to therapeutic treatment with an antiprogestin, comprising (a) obtaining a biological sample from said patient; (b) determining expression levels in said biological sample of at least one gene identified in Table 1a and/or Table 1b; and (c) comparing the expression levels in step (b) to expression levels of the same gene(s) in a control, wherein the patient is a responder to treatment with an antiprogestin if the level of at least one gene in Table 1a and/or Table 1b is increased/up-regulated in the sample from said biological sample as compared to said control. In another embodiment, the expression level of at least one gene is decreased/down-regulated in the biological sample.

Another embodiment provides a method to determine if a breast cancer patient will respond to antiprogestin treatment comprising: a. measuring the level of expression of at least one gene identified in Table 1a and/or Table 1b in a biological sample from the patient, b. wherein the level of expression of the at least one gene in the biological sample is an indication that the subject will respond to antiprogestin treatment.

In one embodiment, the mRNA levels are measured as an indicator of gene expression levels. In one embodiment, multiple mRNAs are measured separately. In another embodiment, multiple mRNAs are measured simultaneously. In one embodiment, the expression level of at least one gene can be measured using any of the techniques selected from the group consisting of in situ hybridization, Northern blot, nucleic acid amplification, microarray analysis or a combination thereof. In one embodiment, the nucleic acid amplification method is selected from the group consisting of polymerase chain reaction, quantitative polymerase chain reaction, reverse transcription polymerase chain reaction, ligase chain reaction or a combination thereof. In another embodiment, the gene expression levels are measured by microarray analysis.

In one embodiment, the expression of at least two genes identified in Table 1a and/or Table 1b is measured. In another embodiment, the expression of at least 3 genes identified in Table 1a and/or Table 1b is measured. In one embodiment, the expression of at least 4 genes identified in Table 1a and/or Table 1b is measured. In another embodiment, the expression of at least 6 genes identified in Table 1a and/or Table 1b is measured. In one embodiment, the expression of at least 9 genes identified in Table 1a and/or Table 1b is measured. In another embodiment, the expression of at least 12 genes identified in Table 1a and/or Table 1b is measured. In another embodiment, the expression of at least 15 genes identified in Table 1 and/or 16 genes identified in Table 1b is measured.

In one embodiment, the expression of the gene(s) is increased compared to the control.

In one embodiment, the biological sample is a tissue biopsy, ductal lavage, fine needle aspiration, section of a surgically removed tumor, circulating tumor cells, circulating DNA or circulating exosomes. In another embodiment, the control is a sample of non-cancerous tissue. In one embodiment, the control of non-cancerous tissue is from the patient. In another embodiment, the control is a predetermined control amount or concentration of the at least one gene. In one embodiment, the negative control is a numerical value or a control range of numerical values.

In one embodiment, the patient is a mammal. In another embodiment, the mammal is a human. In one embodiment a health care provider is informed. In one embodiment, the patient is treated for breast cancer. In one embodiment, the patient is administered an effective amount of at least one antiprogestin. In another embodiment, the treatment further comprises administering at least one additional therapeutic agent.

One embodiment provides a method to treat a cancer patient, comprising administering an anti-progestin, alone or in combination with other treatment, to a patient wherein the expression level of at least one gene in Table 1a and/or Table 1b is increased/up-regulated in a biological sample from said patient as compared to a control.

One embodiment provides a method to treat a cancer patient, comprising administering an anti-progestin, alone or in combination with other treatment, to a patient wherein the expression level of at least one gene in Table 1a is decreased/up-regulated in a biological sample from said patient as compared to a control.

Many PR genes are secreted factors that could be detected in a biological sample such as blood. Therefore, in another embodiment, the gene array or portions thereof as disclosed herein can be used as biomarkers (e.g., including gene expression at the mRNA and protein level) for early detection of cancer in persons not yet diagnosed.

One embodiment provides a method for determining if a patient diagnosed with cancer is afflicted with a cancer that comprises cells expressing an active progesterone receptor (KR) and is likely to respond to therapeutic treatment with an antiprogestin, comprising: (a) obtaining a biological sample from said patient; (b) determining expression level in cells of said biological sample of at least one gene selected from the group consisting of KBTBD11, RBPMS2, PLA2G4B, FLJ12684, SH2D4A, RASD2, CLDN8 and any combination thereof; and (c) comparing the expression level in step (b) to expression levels of said at least one gene in cells of a wild-type (WT) control sample and/or reference sample, wherein the patient is a responder to treatment with an anti-progestin if the expression sample level of said at least one gene in the biological sample is decreased as compared to said control/reference sample. Another embodiment further provides (d) determining the expression level in cells of said biological sample of at least one gene selected from the group consisting of VCX, CHN2, AFAP1L2, PXMP4, THY1, ZNF26, CDH10, ZNF812 and any combination thereof; and (e) comparing the expression level in step (d) to expression levels of said at least one gene in a wild type (WT) control sample and/or reference sample, wherein the patient is a responder to treatment with an antiprogestin if the expression level of said at least one gene in the biological sample is increased as compared to said WT control sample and/or reference sample.

In one embodiment, the cancer is breast, ovarian, endometrial, brain, lung, prostate, endometrial, meningioma or uterine cancer.

Another embodiment provides a method to determine if a cancer patient will respond to antiprogestin treatment comprising: a. measuring the level in the cancer cells of expression of least one gene selected from the group consisting of KBTBD11, RBPMS2, PLA2G4B, FLJ12684, SH2D4A, RASD2, CLDN8 and any combination thereof in a biological sample from the patient, b. wherein a decreased level of expression of the at least one gene in the biological sample compared to said level in a control WT sample and/or reference sample is an indication that the subject will respond to antiprogestin treatment. One embodiment further comprises (c) determining the expression level in cells of said biological sample of at least one gene selected from the group consisting of VCX, CHN2, AFAP1L2, PXMP4, THY1, ZNF26, CDH10, ZNF812 and any combination thereof; and (d) comparing the expression level in step (c) to expression levels of said at least one gene in a wild type (WT) control sample and/or reference sample, wherein the patient is a responder to treatment with an antiprogestin if the expression level of said at least one gene in the biological sample is increased as compared to said WT control sample and/or reference sample (reference controls would be established and the diagnostic equipment is calibrated against the reference control(s)).

In one embodiment, the mRNA levels of at least one gene are measured as an indicator of gene expression levels. In another embodiment, the expression level of at least one gene is measured at a first time and at a second time. In one embodiment, the expression of, for example, gene KB7BD11, is detected by hybridization to a probe of, for example, SEQ ID NO:1. In one embodiment, multiple mRNAs are measured separately. In another embodiment, multiple mRNAs are measured simultaneously. In one embodiment, the probe is one of a plurality of affixed probes that hybridize to at least two of said genes. In one embodiment, measuring the expression level of at least one of said genes comprises in situ hybridization, Northern blot, nucleic acid amplification, microarray analysis or a combination thereof.

In one embodiment, the expression of at least two genes selected from the group consisting of KBTBD11, RBPMS2, PLA2G4B, FLJ12684, SH2D4A, RASD2, CLDN8, VCX, CHN2, AFAP1L2, PXMP4, THY1, ZNF26, CDH10, ZNF812 and any combination thereof is measured. In another embodiment, the expression of at least 3 genes selected from the group consisting of KBTBD11, RBPMS2, PLA2G4B, FLJ12684, SH2D4A, RASD2, CLDN8, VCX, CHN2, AFAP1L2, PXMP4, THY1, ZNF26, CDH10, ZNF812 and any combination thereof is measured. In another embodiment, the expression of at least 4 genes selected from the group consisting of KBTBD11, RBPMS2, PLA2G4B, FLJ112684, SH2D4A, RASD2, CLDN8, VCX, CHN2, AFAP1L2, PXMP4, THY1, ZNF26, CDH10, ZNF812 and any combination thereof is measured. In a further embodiment, the expression of at least 6 genes selected from the group consisting of KBTBD11, RBPMS2, PLA2G4B, FLJ12684, SH2D4A, RASD2, CLDN8, VCX, CHN2, AFAP1L2, PXMP4, THY1, ZNF26, CDH10, ZNF812 and any combination thereof is measured. In another embodiment, the expression of at least 7, 8, 9, 10, 11, 12, 13, 14 or 15 genes selected from the group consisting of KBTBD11, RBPMS2, PLA2G4B, FLJ12684, SH2D4A, RASD2, CLDN8, VCX, CHN2, AFAP1L2, PXMP4, THY1, ZNF26, CDH10, ZNF812 and any combination thereof, is measured.

In one embodiment, the biological sample is a tissue biopsy, ductal lavage, fine needle aspiration, section of a surgically removed tumor, circulating tumor cells, circulating DNA or circulating exosomes. In another embodiment, the control sample is a sample of non-cancerous tissue. In one embodiment, the control sample is from the patient.

One embodiment provides for advising a health care provider to initiate or cease anti-progestin therapy. Another embodiment treats the patient for cancer, for example, by administering an effective amount of at least one antiprogestin. In one embodiment, treatment further comprises administering at least one additional therapeutic agent.

One embodiment provides a method to treat a cancer patient, comprising administering an anti-progestin, alone or in combination with other treatment, to a patient wherein the expression level of at least one gene selected from the group consisting of KBTBD11, RBPMS2, PLA2G4B, FLJ12684, SH2D4A, RASD2, CLDN8 and any combination thereof is decreased and/or wherein the expression level of at least one gene selected from the group consisting of VCX, CHN2, AFAP1L2, PXMP4, THY1, ZNF26, CDH10, ZNF812 and any combination thereof is increased, as compared to a control, so as to treat said cancer patient. Another embodiment further provides (c) determining the expression level in cells of said biological sample of at least one gene selected from the group consisting of VCX, CHN2, AFAP1L2, PXMP4, THY1, ZNF26, CDH10, ZNF812 and any combination thereof; and (d) comparing the expression level in step (a) to expression levels of said at least one gene in a control, wherein the patient is a responder to treatment with an anti-progestin if the expression level of said at least one gene in the biological sample is increased as compared to said control.

One embodiment provides a method for determining if a patient diagnosed with cancer, comprises cells expressing an active progesterone receptor (KR) and is likely to respond to therapeutic treatment with an anti-progestin, comprising (a) obtaining a biological sample from said patient; (b) determining expression level in cells of said biological sample of at least one gene selected from the group consisting of THY1, KLF9, SPINK5L3, PHLDA1, MAP1A, SPRYD5, ATG12, PDK4, MSX2, TUBA3E, TSC22D1, TUBA3D, KHDRBS3, UTS2D, SLC35C1, KIAA0513 and any combination thereof; and (c) comparing the expression level in step (b) to expression levels of said at least one gene in a wild type (WT) control sample and/or a reference sample, wherein the patient is a responder to treatment with an anti-progestin if the expression level of said at least one gene in the biological sample is increased as compared to said WT control sample and/or reference sample.

In one embodiment, the cancer is breast, ovarian, endometrial, brain, lung, prostate, endometrial, meningioma or uterine cancer.

Another embodiment provides a method to determine if a cancer patient, will respond to anti-progestin treatment comprising: a. measuring the level of expression of at least one gene selected from the group of THY1, KLF9, SPINK5L3, PHLDA1, MAP1A, SPRYD5, ATG12, PDK4, MSX2, TUBA3E, TSC22D1, TUBA3D, KHDRBS3, UTS2D, SLC35C1, KIAA0513 and any combination thereof in a biological sample from the patient, b. wherein an increased level of expression of the at least one gene in the biological sample as compared to its level of expression in a WT control sample and/or a reference sample is an indication that the subject will respond to antiprogestin treatment.

In one embodiment, the mRNA levels are measured as an indicator of gene expression levels. In one embodiment, the expression of gene, for example, THY1, is detected by hybridization to a probe of, for example, SEQ ID NO:16.

In one embodiment, multiple mRNAs are measured separately. In another embodiment, multiple mRNAs are measured simultaneously. In one embodiment, measuring the expression level of the at least one gene comprises in situ hybridization, Northern blot, nucleic acid amplification, microarray analysis or a combination thereof.

In one embodiment, the expression of at least two genes selected from the group consisting of THY1, KLF9, SPINK5L3, PHLDA1, MAP1A, SPRYD5, ATG12, PDK4, MSX2, TUBA3E, TSC22D1, TUBA3D, KHDRBS3, UTS2D, SLC35C1, KIAA0513 and any combination thereof is measured. In another embodiment, the expression level of at least 3 genes selected from the group consisting of THY1, KLF9, SPINK5L3, PHLDA1, MAP1A, SPRYD5, ATG12, PDK4, MSX2, TUBA3E, TSC22D1, TUBA3D, KHDRBS3, UTS2D, SLC35C1, KIAA0513 and any combination thereof is measured. In another embodiment, the expression level of at least 4 genes selected from the group consisting of THY1, KLF9, SPINK5L3, PHLDA1, MAP1A, SPRYD5, ATG12, PDK4, MSX2, TUBA3E, TSC22D1, TUBA3D, KHDRBS3, UTS2D, SLC35C1, KIAA0513 and any combination thereof is measured. In another embodiment, the expression level of at least 6 genes selected from the group consisting of THY1, KLF9, SPINK5L3, PHLDA1, MAP1A, SPRYD5, ATG12, PDK4, MSX2, TUBA3E, TSC22D1, TUBA3D, KHDRBS3, UTS2D, SLC35C1, KIAA0513 and any combination thereof is measured. In another embodiment, the expression level of at least 7 genes selected from the group consisting of THY1, KLF9, SPINK5L3, PHLDA1, MAP1A, SPRYD5, ATG12, PDK4, MSX2, TUBA3E, TSC22D1, TUBA3D, KHDRBS3, UTS2D, SLC35C1, KIAA0513 and any combination thereof is measured. In another embodiment, the expression level of at least 8, at least 9, at least 10, at least 11, at least 12, at least 13, at least 14, at least 15 or 16 genes selected from the group consisting of THY1, KLF9, SPINK5L3, PHLDA1, MAP1A, SPRYD5, ATG12, PDK4, MSX2, TUBA3E, TSC22D1, TUBA3D, KHDRBS3, UTS2D, SLC35C1, KIAA0513 and any combination thereof is measured.

In one embodiment, the biological sample is a tissue biopsy, ductal lavage, fine needle aspiration, section of a surgically removed tumor, circulating tumor cells, circulating DNA or circulating exosomes. In another embodiment, the control sample is a sample of non-cancerous tissue, for example, from said patient.

One embodiment provides for informing a health care provider to initiate or cease anti-progestin treatment. Another embodiment comprises treating the patient for cancer. In one embodiment, the treatment comprises administering an effective amount of at least one anti-progestin. In another embodiment, the treatment further comprises administering at least one additional therapeutic agent.

One embodiment provides a method to treat a cancer patient, comprising administering an anti-progestin, alone or in combination with other treatment, to a patient wherein the expression level of at least one gene selected from the group consisting of THY1, KLF9, SPINK5L3, PHLDA1, MAP1A, SPRYD5, ATG12, PDK4, MSX2, TUBA3E, TSC22D1, TUBA3D, KHDRBS3, UTS2D, SLC35C1, KIAA0513 and any combination thereof is increased as compared to a control, so as to treat said cancer patient.

BRIEF DESCRIPTION OF THE DRAWINGS

FIGS. 1A-F. Gene expression profiling of T47D cells stably expressing WT or SUMO-deficient PR, treated with or without R5020 for 6 h. (A) Western blot showing total and phospho-Ser294 PR proteins (total ERK1/2 served as a loading control) in 12 human breast tumors. (B) T47D cells stably expressing either wild-type PR-B (WT), SUMO-deficient mutant K388R PR-B (KR), or empty vector (null) controls were treated without or with R5020 prior to western blotting for PR-B. (C) Heat map showing normalized expression values for differentially expressed transcripts (fold change >8.0 in at least one sample, BH adjusted P<0.001). Biological duplicates are shown for each treatment group and notable gene expression categories (numbered 1-4 on right side) are described (see Results). (D) Venn diagrams showing up- or downregulated PR target genes following progestin treatment ($\log_2$ fold change >0.6, BH adjusted P<0.01; common fold change >1.5). (E) Venn diagrams (as in part D) depicting the number of ligand-independent PR target genes up- or downregulated relative to PR-null cells. (F) Relative mRNA expression (as determined by RT-qPCR) of selected PR target genes in T47D cells stably expressing vector control (PR-null), WT or KR PR and treated without or with R5020 for 6 h; genes chosen from ligand-dependent (LD) or ligand-independent (LI) Venn categories are indicated (note matching color labels). Data are represented as mean of n=3+/−SD.

FIGS. 1.1A-C. Creation and validation of isogenic models of inducible PR expression in T47D cells. (A) Clonal inducible cell lines were developed as described in the Materials and Methods and PR protein expression was determined by western blotting after treatment with inducer molecule AP21967 for 2 days and R5020 for 1 h. Progestin-dependent PR phosphorylation was measured using a PR phospho-Ser294 specific antibody. Beta-actin western blotting was performed as a loading control. Short-term treatment with R5020 demonstrated progestin-dependent PR global phosphorylation (as indicated by a slight gel upshift in total PR) and equal levels of ligand-dependent Ser294 phosphorylation. (B) Gene set enrichment analysis (GSEA) comparison of whole genome expression profiling data sets derived from two independent model systems and platforms: (i) T47D cells stably expressing WT and mutant KR PRs (−/+R5020) using the Illumina HT-12v4 platform and (ii) T47D cells expressing inducible WT or mutant KR PR (−/+AP21967, −/+R5020) using the Affymetrix U133A 2.0 platform. Genes most upregulated in the Illumina dataset by WT +R5020 (or KR +R5020) appear on the far left and genes most downregulated by WT +R5020 (or KR +R5020) appear on the far right side. Using the GSEA application, Affymetrix genes (black vertical bars) were positioned along the Illumina dataset (from upregulated to downregulated genes) and the statistical enrichment score was determined. All the treatment groups between Affymetrix and Illumina were statistically significant (P<0.001). (C) Gene expression levels were validated for two PR target genes (MSX2 and MAP1A) in T47D cell lines expressing iWT and iKR PR. Cells were treated with AP21967 to induce PR expression and co-treated with RU486 and/or R5020 before RT-qPCR gene expression analysis. Data are represented as mean of n=3+/−SD.

FIGS. 2A-E. Phosphorylation of PR Ser294 drives SUMO-deficient PR gene expression and promoter selectivity in MCF-7 and T47D cells. (A) Relative expression level (copy number) of PR target genes in tissue samples from patient cohorts. (B) Relative gene expression levels of selected PR target genes in MCF-7 cells stably expressing either empty vector (PR-null), WT or SUMO-deficient K388R PRs. Cells were co-treated with the synthetic progestin R5020 and/or antiprogestin RU486 for 6 h and mRNA levels were measured using RT-qPCR (see Methods). (C) Relative gene expression levels of the same PR target genes (as in parts A-B) were measured using RT-qPCR in five vector-matched T47D cell lines stably expressing PRs: empty vector (null), wild-type (WT) PR, K388R mutant (KR) PR, S294A mutant (SA) PR, and K388R and S294A double mutant (KRSA) PR. Cells were treated with R5020 for 6 h. (D) T47D cells expressing WT PR were treated cells with epidermal growth factor (EGF) for 2 days and treated with R5020 for 3, 24, or 48 h. Relative MAP1A and RGS2 mRNA levels were measured using RT-qPCR. (E) Parental T47Dco cells were pretreated with EGF for 20 min prior to 24 h of R5020 treatment. Relative RGS2 mRNA levels were measured by RT-qPCR. Data are represented as mean of n=3+/−SD and significance calculated using Student's t-test.

FIGS. 3A-F. Promoter selectivity is achieved through increased recruitment of SUMO-deficient KR PR, CBP, MLL2 and histone tail modification, H3K4me2, to enhancer loci. (A) Schematic showing the MSX2 gene PRE-containing enhancer region located 15,094 bp upstream from the transcriptional start site. (B) Relative recruitment of PR to the MSX2 enhancer region was measured by ChIP-qPCR assays in T47D cells expressing constitutive PR null, WT or KR PR after treatment with R5020 for 1 or 4 h. PR recruitment values were normalized as a percentage of input chromatin DNA values. To control for background non-specific antibody binding, immunoprecipitated chromatin contained a mixture from all samples with an IgG antibody. Similar ChIP results were obtained in T47D cells expressing inducible PR (right side). (C) The relative recruitment of CBP to the MSX2 enhancer region was measured as described in part B. (D) Levels of H3K4 dimethylation at the MSX2 enhancer were measured in the inducible PR expressing cell lines (iWT and iKR). The presence of H3K4me2 was determined at the MSX2 enhancer, up/downstream from the PRE, using overlapping qPCR products that span the region. (E) MLL2 recruitment to the MSX2 enhancer region was determined in T47D cells expressing both constitutive PR and inducible PR, as described in part B. (F) MAT2A gene expression was measured by RT-qPCR in T47D cells expressing stable WT or SUMO-deficient KR PR. Additionally, PR and MLL2 recruitment was quantified in these cells, as measured by standard ChIP-qPCR assay. Data are represented as mean of n=3+/−SD and significance calculated using Student's t-test. See also FIG. 3.1, 3.2.

FIGS 3.1A-B. ChIP assays showing relative recruitment of WT and SUMO-deficient PR molecules to selected PR target gene enhancers, related to FIG. 3. (A) Recruitment of PR molecules to consensus PRE sequences in upstream promoter/enhancer regions of RGS2, MAP1A, and PDK4 (following 1 h R5020 exposure) was measured by standard ChIP assay in inducible models of T47D cells expressing WT (iWT) and KR (iKR) receptors. Recruitment of PR to an intronic region of the HBB gene was included as a negative control. (B) ChIP assays were performed as in part A, to demonstrate differential PR recruitment to a RGS2 enhancer in T47D cells stably expressing either WT or SUMO-deficient (KR) PR. Data are represented as mean of n=3+/−SD.

FIGS. 3.2A-B. ChIP analysis at the MSX2 proximal promoter region for recruitment of phospho-Ser5 and total-RNA polymerase II. (A) Recruitment of total RNA polymerase II to the MSX2 proximal promoter region (following 1 h R5020 exposure) was measured by standard ChIP assay in inducible models of T47D cells expressing WT (iWT) and KR (iKR) receptors. (B) ChIP assay was performed as in part A, using an antibody targeting functionally active RNA polymerase II, as measured by detection of CTD Ser5 phosphorylation. Data are represented as mean of n=3+/−SD.

FIG. 3.3. SUMO-deficient PR upregulates genes involved in cell proliferation determined by Ingenuity Pathway Analysis. Significant expression (y-axis) of multiple cellular functions (x-axis) containing genes upregulated by progestin ($\log_2$ fold change >1.0, BH adjusted P<0.01; common fold change >2.0) in cells expressing either WT or KR PR. Biological pathways that contain a significant number of upregulated genes display bars above the horizontal line, representing BH adjusted P<0.05.

FIGS. 4.1A1-A3 and 4.1B1-B3. 151 genes LD KR>WT and 92 genes LI KR>WT. The ligand-dependent (LD) and ligand-independent (LI) KR>WT gene signatures are provided. The LD (151 genes) and LI (92 genes) KR>WT gene signature lists are provided in whole along with their respective Probe IDs.

FIGS. 5A-D. The SUMO-deficient PR gene expression signature is associated with HER2-positive human breast tumors and predicts reduced patient survival. (A) Normalized gene expression levels (for genes in our LD KR>WT gene signature) are presented for each tumor in the patient cohort (Bonnefoi et al., 2007), organized by ERBB2 status. (B) Gene expression levels were measured by RT-qPCR for CHN2 and RGS2 (both upregulated by SUMO-deficient PR, and members of the LD KR>WT gene signature) and the control gene ACOT6 (equally upregulated by both WT and KR receptors) in BT-474 human breast cancer cells. Cells were pre-treated with MEK kinase inhibitor U0126 prior to progestin or antiprogestin co-treatment. Protein levels were evaluated by western blotting for total PR, PR Ser294 phosphorylation, total ERK1/2, and ERK1/2 phosphorylation. (C) Kaplan-Meier survival curve for time to distant metastasis for patients whose tumors expressed the combined T47D metagenes (WT or KR, −/+R5020) relative to patient tumors lacking these metagenes. Patient samples include untreated and tamoxifen-treated ER-positive tumors from the Loi et al. dataset (Loi et al., 2007). (D) Survival curves as in part C for patients whose tumors expressed the combined T47D metagenes (KR −R5020, or KR +R5020) relative to patient tumors lacking these metagenes. See also FIG. 4.1.

FIG. 5.1A-C2-Three tables depicting Antibody name and Primer name/sequence. This figure contains all the antibody information and primers sets used in RT- and ChIP-qPCR assays.

upregulated expression values are represented in red and downregulated expression values are represented in blue.

Figure 7:
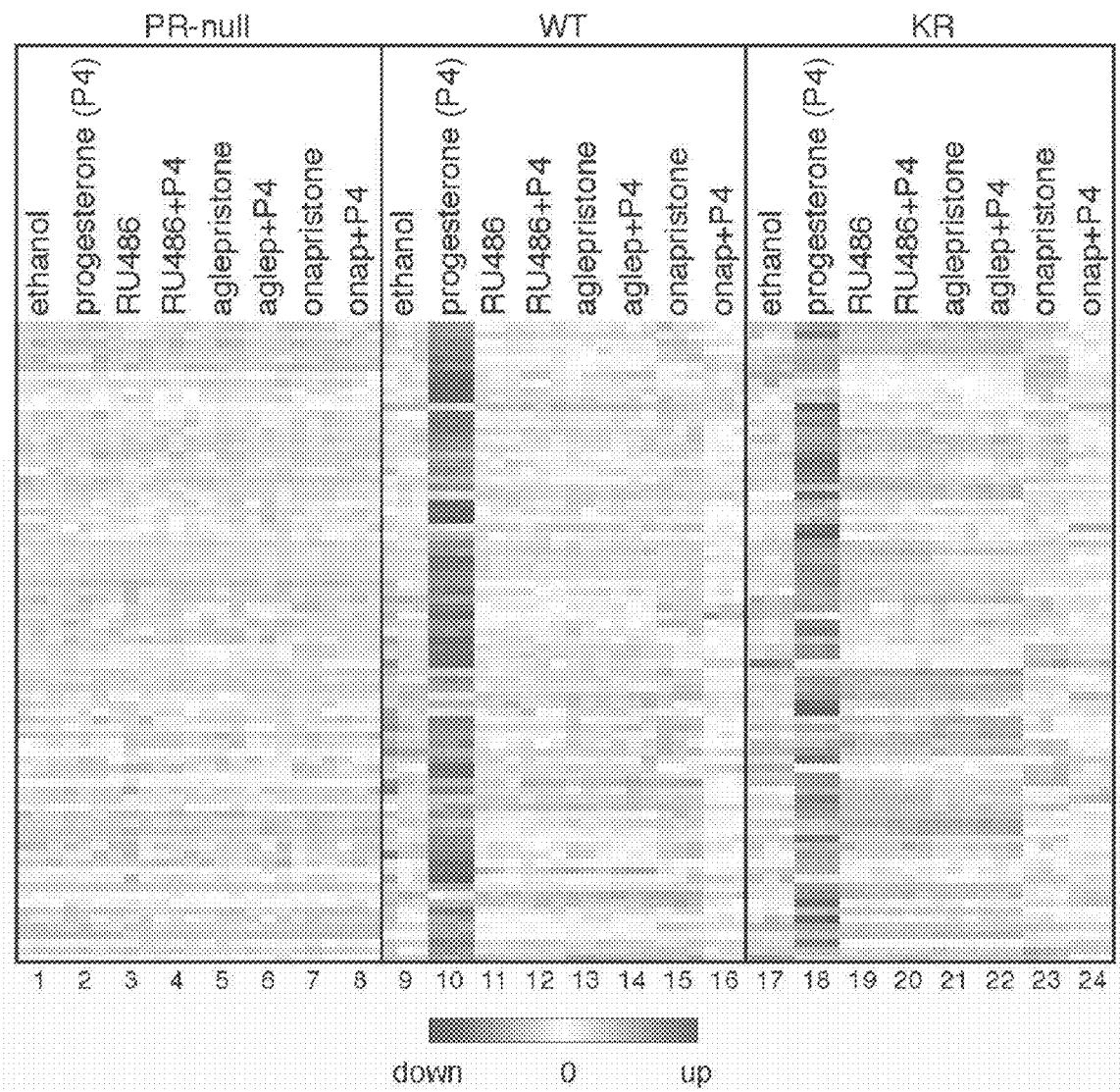

FIG. 7. Top progesterone-regulated genes are also upregulated in cells expressing SUMO-deficient PR after treatment with antiprogestins RU486 and aglepristone, but not onapristone. Heat map displaying normalized relative expression values for any transcripts that were upregulated (>2.5 fold, BH adjusted P<0.01) after progesterone treatment (i.e. progesterone vs. ethanol) in any cell line. Cell lines were treated for 6 hours in each individual cohort and biological triplicates are shown for each treatment group. Genes (rows) were grouped based on unsupervised hierarchal clustering; upregulated expression values are represented in red and downregulated expression values are represented in blue.

Figure 8:
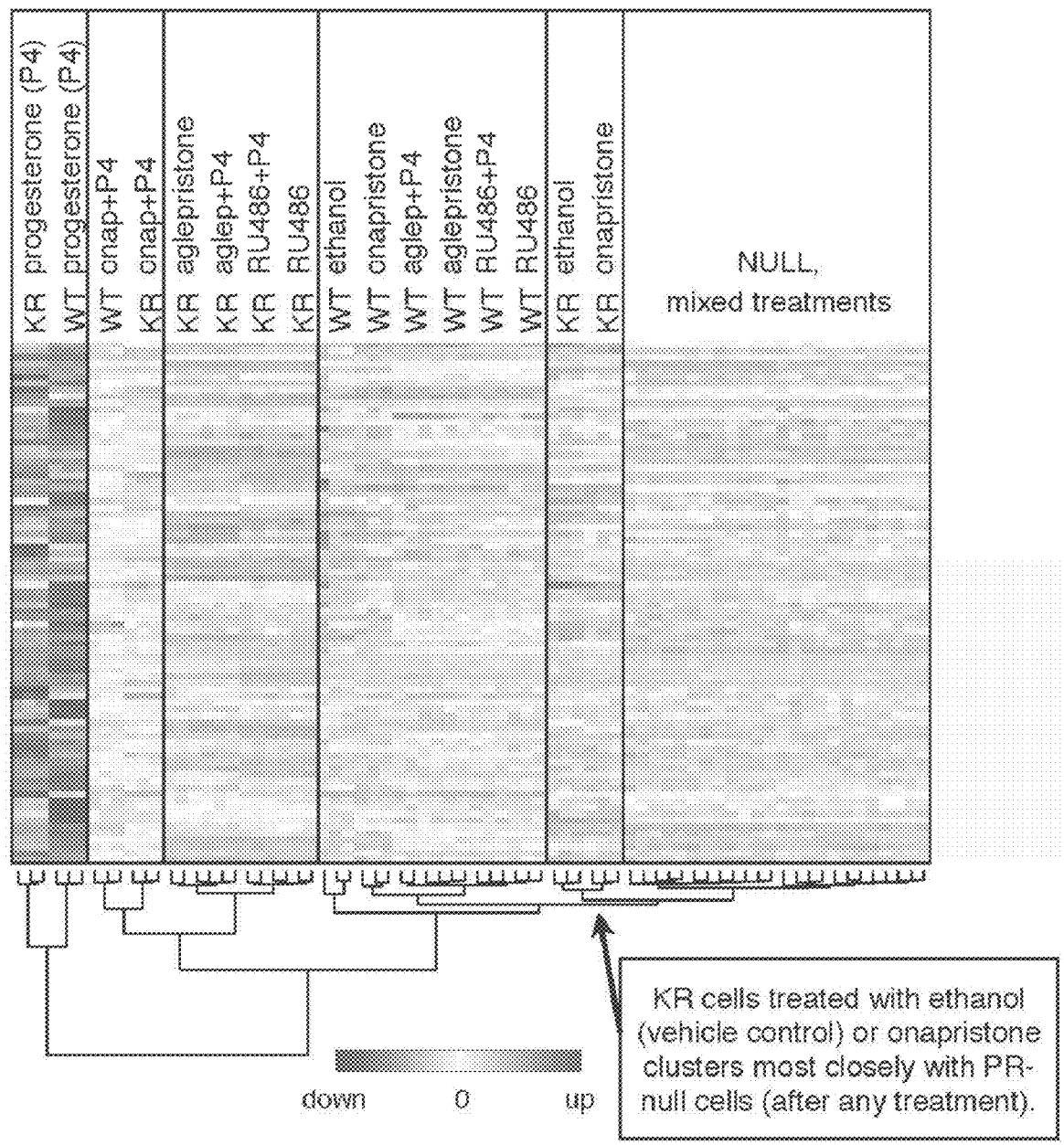

FIG. 8. Cells treated with onapristone do not stimulate gene expression in cells expressing PR. Unsupervised hierarchal clustering of treatment groups (columns) from FIG. 7. Genes (rows) were also grouped based on unsupervised hierarchal clustering; upregulated expression values are represented in red and downregulated expression values are represented in blue.

Figure 9:
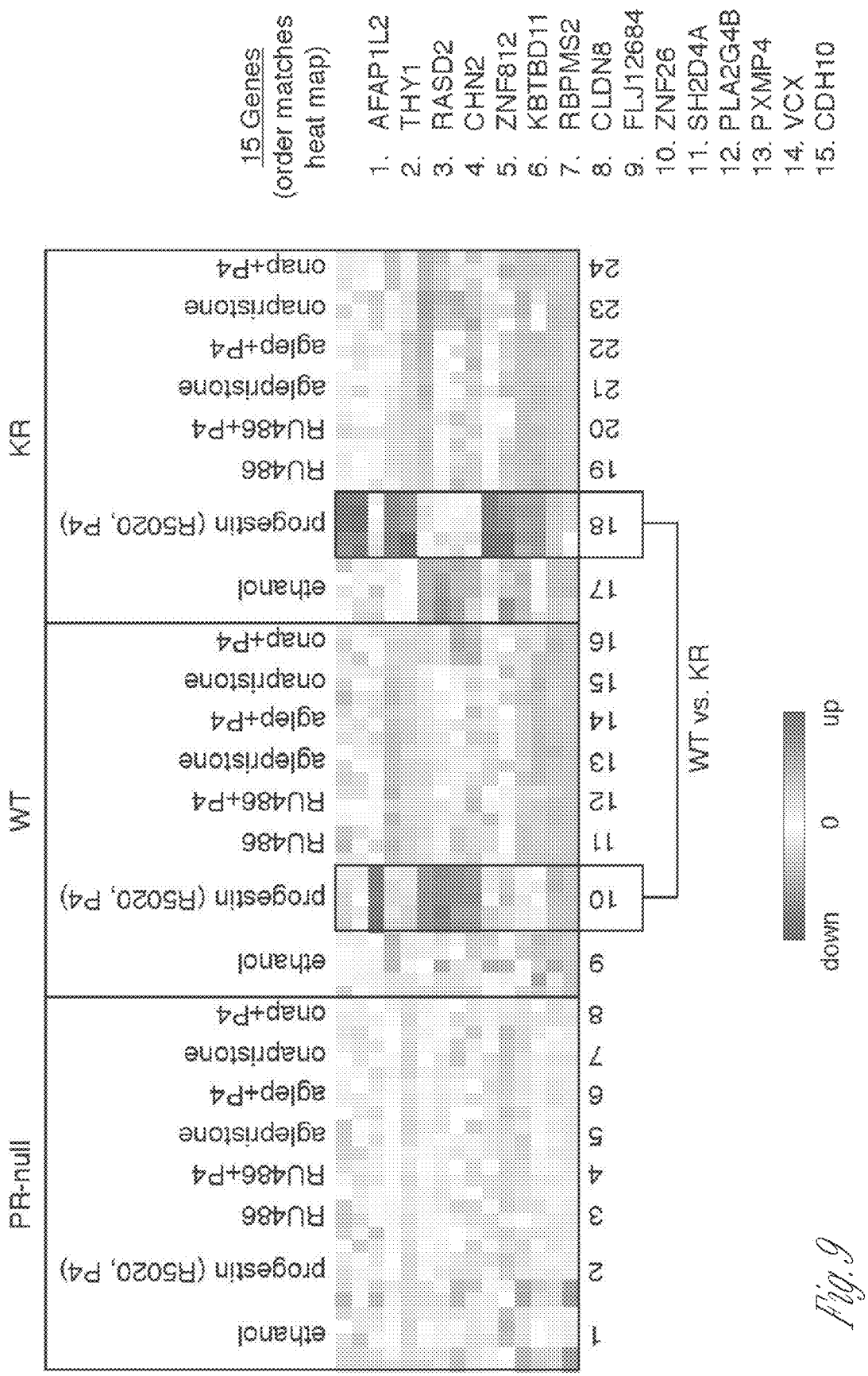

FIG. 9. Fifteen genes that can discriminate between cells expressing WT or KR PR. These 15 genes are uniquely regulated in WT or KR cells, as determined by passing three independent statistical methods (see methods). Heat map displaying normalized relative expression values for each transcript. Samples were treated for 6 hours and biological triplicates are shown for each treatment group (n=5 for ethanol and progestin groups). Genes (rows) were grouped based on unsupervised hierarchal clustering; upregulated expression values are represented in red and down regulated expression values are represented in blue.

Figure 10:
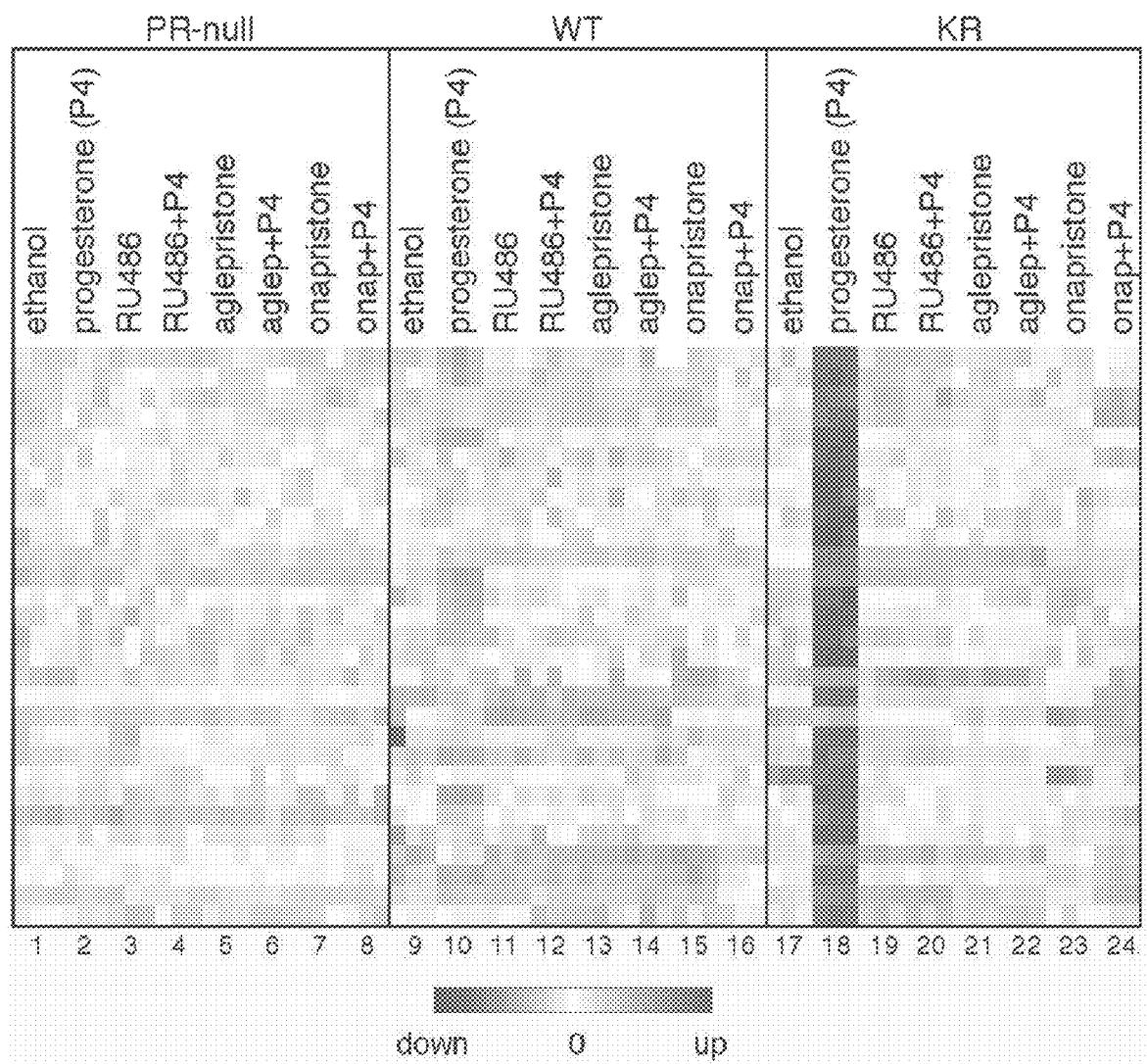

FIG. 10. Twenty-nine genes are specifically upregulated in cells expressing KR, as identified by overlapping two independent microarray experiments. Heat map displaying normalized relative expression values for all transcripts that were upregulated (>1.5 fold, BH adjusted P<0.01) specifically in cells expressing SUMO-deficient PR (KR) after progesterone (P4) treatment, compared to cells expressing WT PR. Samples were treated for 6 hours and biological triplicates are shown for each treatment group. Genes (rows) were grouped based on unsupervised hierarchal clustering; upregulated expression values are represented in red and down regulated expression values are represented in blue.

Figure 11:
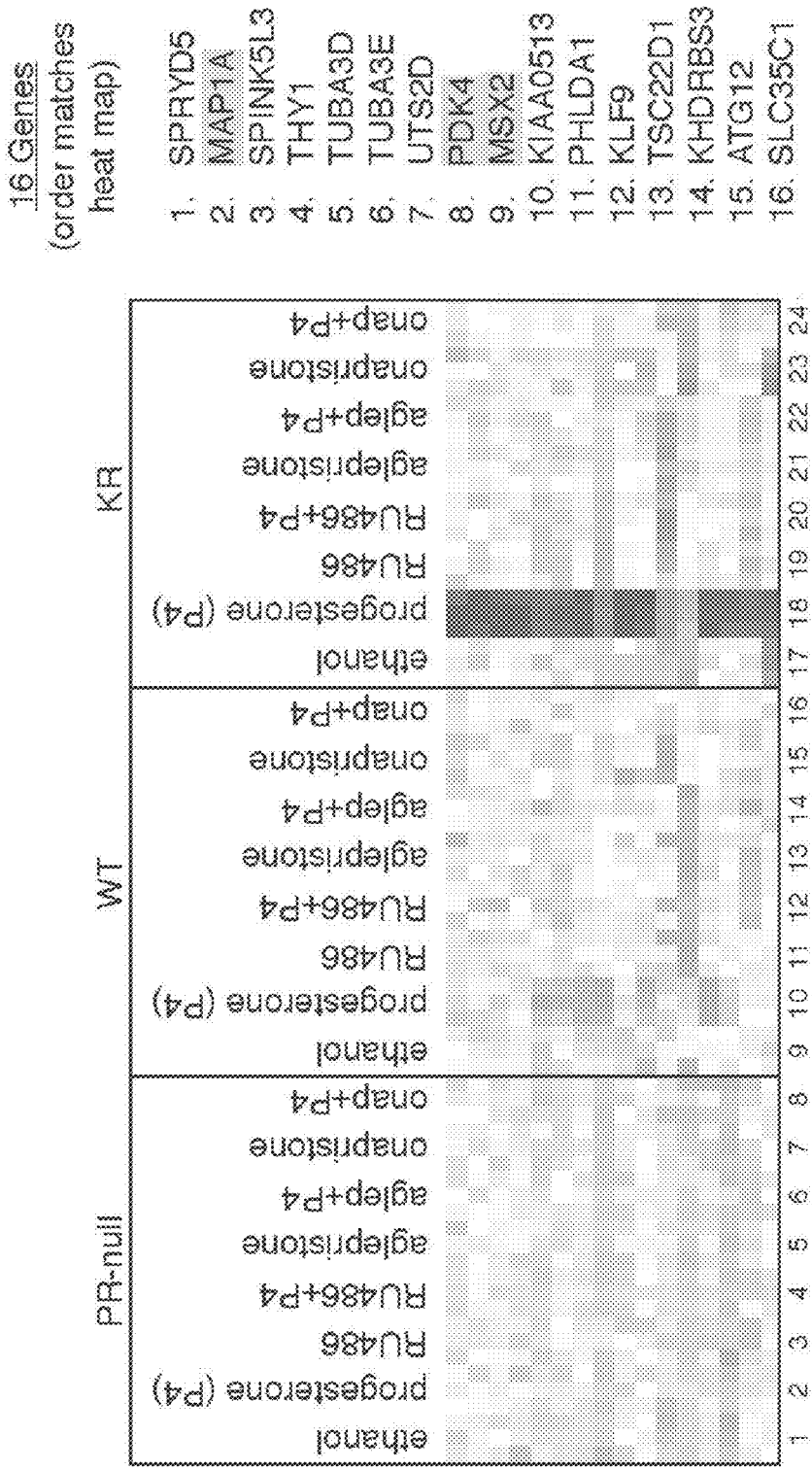

FIG. 11. The refined progestin-dependent KR>WT gene signature. Genes from FIG. 10 that were significantly (BH adjusted P<0.01) stimulated by onapristone treatment (alone or in combination with P4) were removed, resulting in 16 genes. Heat map displaying normalized relative expression values for the 16 transcripts specifically upregulated in cells expressing SUMO-deficient PR (KR) after progesterone treatment, compared to cells expressing WT PR. Samples were treated for 6 hours and biological triplicates are shown for each treatment group. Genes (rows) were grouped based on unsupervised hierarchal clustering; upregulated expression values are represented in red and down regulated expression values are represented in blue.

DETAILED DESCRIPTION OF THE INVENTION

Progesterone receptors (PR) play an important role in the proliferation and growth of certain cancers, including breast and endometrial malignancies. Phosphorylation events common to breast cancer cells impact PR transcriptional activity. Phospho-Ser294 PRs are resistant to ligand-dependent Lys388 SUMOylation (i.e. a repressive modification). Antagonism of PR SUMOylation by protein kinases provides a mechanism for PR derepression (i.e. transcriptional activation). Global gene expression profiling in breast cancer cells expressing wild-type or K388R(SUMOylation-deficient) PR revealed that SUMOylation-deficient PRs primarily regulate genes required for proliferative and pro-survival signaling. K388R PR are preferentially recruited to enhancer regions of candidate "SUMO-sensitive" genes with steroid receptor coactivators, CBP and MLL2, a mediator of nucleosome remodeling. SUMO-deficient (phospho-Ser294) PR gene signatures are significantly associated with ERBB2-overexpressing breast tumors and predictive of early metastasis and shortened survival. It is concluded that reversible PR SUMOylation/deSUMOylation profoundly alters target gene selection in breast cancer cells. Patients whose ER positive and/or PR positive tumors are driven by phospho-PRs can benefit from endocrine therapies containing antiprogestins.

The gene signature described herein contains a collection of related genes known to contribute to cancer progression, and it is now known that their expression is directly dependent on activated phospho-PR (deSUMOylated PR-B). As the mechanism involved has been determined as described herein, the test will identify those breast cancer patients with PR-driven tumors who would benefit from treatments that include the use of anti-progestins (aimed at blocking the activity of PR and the interaction of PR with other malignant growth and proliferation pathways). The defined pattern of gene expression defined herein is due to deSUMOylated phospho-PR, and a drug option (anti-progestin therapy alone or in combination with other anti-cancer agents) is likely to be an effective treatment strategy for those with the activated PR gene expression pattern. This therapy can include an anti-progestin drug plus the current standard of care endocrine treatment for $ER^+$ breast tumors, (for example, anti-estrogen or aromatase inhibitor combined with an anti-progestin) or an anti-progestin drug plus other anti-cancer compounds (e.g., everolimus, trastuzumab, T-DM1, anti-HER2 drugs, m-TOR inhibitors, anti-VEGF drugs, anti-EGF drugs, bevacizumab, paclitaxel, docetaxel, taxanes, doxorubicin, liposomal doxorubicin, pegylated liposomal doxorubicin, anthracyclines, anthracenediones, carboplatin, cisplatin, 5-FU, gemcitabine, cyclophosphamide). Thus, with anti-progestin treatment, tumor regression and reversion of the PR gene signature will occur.

The present invention provides gene expression profiles and their use for predicting a patient's responsiveness to a cancer treatment. More specifically, the gene expression profiles are indicative of whether a patient afflicted with breast cancer is a responder or a non-responder to treatment with endocrine therapy that includes an antiprogestin.

There have been significant improvements in the outcomes of breast cancer treatment. However, many times, the growth of normal cells is often affected by these treatments, causing unwanted and/or unpleasant effects. These other effects may include: diarrhea, rash, acne, dry skin, nausea (feeling sick) and vomiting, loss of appetite and weight loss, asthenia and pruritus, neuropathy and abdominal pain. Aspects of the present invention provides biomarkers that are associated with those patients that will benefit from treatment with antiprogestin. The present invention thus enables the treatment provider to determine in advance those breast cancer patients likely to benefit from treatment with an antiprogestin, and to consider alternative treatment options for non-responders.

Aspects of the present invention comprises gene expression profiles that are indicative of the tendency of a patient afflicted with breast cancer to respond to treatment with an antiprogestin. The gene expression profile comprises at least one, and preferably a plurality, of genes that identified in Table 1a and or 1b. This group of genes is referred to herein as the "Antiprogestin Responder Genes". According to aspects of the invention, some or all of theses genes are differentially expressed (e.g., up-regulated or down-regulated) in patients who are responders to antiprogestin therapy. Accordingly, it is possible to determine in advance if a patient is likely to benefit from such therapy by obtaining a gene expression profile from the patient's tissue, and determining whether one or more of the genes in the Antiprogestin Responder Genes is up- or down-regulated.

In one embodiment, the gene expression profiles of the present invention comprise at least about four, including about four to about nine, and including between about nine and 15 or more of the Antiprogestin Responder Genes that are regulated. In one embodiment, the gene expression profile comprises at least about four, including about six to twelve, of the Antiprogestin Responder Genes that are regulated.

The gene expression profiles of the invention can be used to predict the responsiveness of a breast cancer patient to therapy an anti-progestin. In one aspect, the present method comprises (a) obtaining a gene expression profile from a biological sample (tissue biopsy, ductal lavage, fine needle aspiration sample, section of a surgically removed tumor or circulating tumor cells) from a patient afflicted with breast cancer; (b) determining from the gene expression profile whether expression of one or more of the genes identified in Table 1a and/or 1b is up- or down-regulated (over- or under-expressed). In one embodiment, the predictive value of the gene profile for determining response to these compounds increases with the number of the associated genes that are found to be up- or down-regulated in accordance with the invention.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, several embodiments with regards to methods and materials are described herein. As used herein, each of the following terms has the meaning associated with it in this section.

The articles "a" and "an" are used herein to refer to one or to more than one (i.e. to at least one) of the grammatical object of the article. By way of example, "an element" means one element or more than one element.

"Plurality" means at least two.

A "subject" or "patient" is a vertebrate, including a mammal, such as a human. Mammals include, but are not limited to, humans, farm animals, sport animals and pets.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. In one aspect, the term "about" means plus or minus 20% of the numerical value of the number with which it is being used. Therefore, about 50% means in the range of 45%-55%. Numerical ranges recited herein by endpoints include all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about."

The term "gene" refers to a nucleic acid sequence that comprises control and coding sequences necessary for producing a polypeptide or precursor. The polypeptide may be encoded by a full length coding sequence or by any portion of the coding sequence. The gene may be derived in whole or in part from any source known to the art, including a plant, a fungus, an animal, a bacterial genome or episome, eukaryotic, nuclear or plasmid DNA, cDNA, viral DNA, or chemically synthesized DNA. A gene may contain one or more modifications in either the coding or the untranslated regions that could affect the biological activity or the chemical structure of the expression product, the rate of expression, or the manner of expression control. Such modifications include, but are not limited to, mutations, insertions, deletions, and substitutions of one or more nucleotides. The gene may constitute an uninterrupted coding sequence or it may include one or more introns, bound by the appropriate splice junctions.

The term "gene expression" refers to the process by which a nucleic acid sequence undergoes successful transcription and/or translation such that detectable levels of the nucleotide sequence are expressed.

The terms "gene expression profile" or "gene signature" refer to a group of genes expressed by a particular cell or tissue type wherein presence of the genes taken together or the differential expression of such genes, is indicative/predictive of a certain condition.

The term "nucleic acid" as used herein, refers to a molecule comprised of one or more nucleotides, i.e., ribonucleotides, deoxyribonucleotides, or both. The term includes monomers and polymers of ribonucleotides and deoxyribonucleotides, with the ribonucleotides and/or deoxyribonucleotides being bound together, in the case of the polymers, via 5' to 3' linkages. The ribonucleotide and deoxyribonucleotide polymers may be single or double-stranded. However, linkages may include any of the linkages known in the art including, for example, nucleic acids comprising 5' to 3' linkages. Furthermore, the term "nucleic acid sequences" contemplates the complementary sequence and specifically includes any nucleic acid sequence that is substantially homologous to the both the nucleic acid sequence and its complement.

The terms "array" and "microarray" refer to the type of genes represented on an array by oligonucleotides, and where the type of genes represented on the array is dependent on the intended purpose of the array (e.g., to monitor expression of human genes). The oligonucleotides on a given array may correspond to the same type, category, or group of genes. Genes may be considered to be of the same type if they share some common characteristics such as species of origin (e.g., human, mouse, rat); disease state (e.g., cancer); functions (e.g., protein kinases, tumor suppressors); or same biological process (e.g., apoptosis, signal transduction, cell cycle regulation, proliferation, differentiation). For example, one array type may be a "cancer array" in which each of the array oligonucleotides correspond to a gene associated with a cancer.

The term "activation" as used herein refers to any alteration of a signaling pathway or biological response including, for example, increases above basal levels, restoration to basal levels from an inhibited state, and stimulation of the pathway above basal levels.

The term "differential expression" refers to both quantitative as well as qualitative differences in the temporal and tissue expression patterns of a gene in diseased tissues or cells versus normal adjacent tissue. For example, a differentially expressed gene may have its expression activated or partially or completely inactivated in normal versus disease conditions, or may be up-regulated (over-expressed) or down-regulated (under-expressed) in a disease condition versus a normal condition. Such a qualitatively regulated gene may exhibit an expression pattern within a given tissue or cell type that is detectable in either control or disease conditions, but is not detectable in both. Stated another way, a gene is differentially expressed when expression of the gene occurs at a higher or lower level in the diseased tissues or cells of a patient relative to the level of its expression in the normal (disease-free) tissues or cells of the patient and/or control tissues or cells.

The term "biological sample" refers to a sample obtained from an organism (e.g., a human patient) or from components (e.g., cells) of an organism. The sample may be of any biological tissue or fluid. The sample may be a "clinical sample" which is a sample derived from a patient. Such samples include, but are not limited to, sputum, blood, blood cells (e.g., white cells), amniotic fluid, plasma, semen, bone marrow, circulating tumor cells, circulating DNA, circulating exosomes, and tissue or fine needle biopsy samples, urine, peritoneal fluid, and pleural fluid, or cells therefrom. Biological samples may also include sections of tissues such as frozen sections or formalin fixed paraffin embedded sections aken for histological purposes. A biological sample may also be referred to as a "patient sample."

As used herein, "health care provider" includes either an individual or an institution that provides preventive, curative, promotional or rehabilitative health care services to a subject, such as a patient. In one embodiment, the data is provided to a health care provider so that they may use it in their diagnosis/treatment of the patient.

The term "standard," as used herein, refers to something used for comparison, such as control or a healthy subject.

The terms "comprises", "comprising", and the like can have the meaning ascribed to them in U.S. Patent Law and can mean "includes", "including" and the like. As used herein, "including" or "includes" or the like means including, without limitation.

Cancer

The methods disclosed herein can be used to identify patients whose cancer is likely to undergo PR-driven proliferation and progression to endocrine-resistance to antiestrogen or aromatase inhibitor treatment. Such patients would be candidates for endocrine therapy that contains an antiprogestin. The gene signature described herein can be used in many cancers, such as lung, brain, prostate, endometrial, meningiomas, prostate, ovarian cancers, and uterine sarcomas/cancers. The gene signature described herein can be used in other disorders including lymphangioleiomyomatosis and uterine leiomyoma.

Breast Cancer

Breast cancer is the most commonly diagnosed cancer in women, and the second leading cause of cancer-related death. Breast cancer (malignant breast neoplasm) is a type of cancer originating from breast tissue, most commonly from the inner lining of milk ducts or the lobules that supply the ducts with milk. Cancers originating from ducts are known as ductal carcinomas; those originating from lobules are known as lobular carcinomas. Breast cancer is a disease of humans and other mammals; while the overwhelming majority of cases in humans are women, men can sometimes also develop breast cancer.

The size, stage, rate of growth, and other characteristics of the tumor determine the kinds of treatment. Treatment may include surgery, drugs (hormonal therapy and chemotherapy), radiation and/or immunotherapy. Surgical removal of the tumor provides the single largest benefit, with surgery alone being capable of producing a cure in many cases. To somewhat increase the likelihood of long-term disease-free survival, several chemotherapy regimens are commonly given in addition to surgery. Most forms of chemotherapy kill cells that are dividing rapidly anywhere in the body, and as a result cause temporary hair loss, damage to the bone marrow and immune systems and digestive disturbances. Radiation is indicated especially after breast conserving surgery and substantially improves local relapse rates and in many circumstances also overall survival. Some breast cancers are sensitive to hormones such as estrogen and/or progesterone, which make it possible to treat them by blocking the effects of these hormones.

Worldwide, breast cancer comprises 22.9% of all cancers (excluding non-melanoma skin cancers) in women. In 2008, breast cancer caused 458,503 deaths worldwide (13.7% of cancer deaths in women). Prognosis and survival rates vary greatly depending on cancer type, staging and treatment.

The first noticeable symptom of breast cancer is typically a lump that feels different from the rest of the breast tissue. The earliest breast cancers are detected by a mammogram. Lumps found in lymph nodes located in the armpits can also indicate breast cancer.

Indications of breast cancer other than a lump may include changes in breast size or shape, skin dimpling, nipple inversion, or spontaneous single-nipple discharge. Pain ("mastodynia") is generally an unreliable tool in determining the presence or absence of breast cancer, but may be indicative of other breast health issues.

Breast cancer is usually treated with surgery and possibly with chemotherapy or radiation, or all of the above. A multidisciplinary approach is preferable. Hormone positive cancers are treated with long term hormone blocking therapy. Treatments are given with increasing aggressiveness according to the prognosis and risk of recurrence. Stage 1 cancers (and DCIS) have an excellent prognosis and are generally treated with lumpectomy and sometimes radiation. HER2 positive cancers can be treated with the trastuzumab (Herceptin®) regime. Chemotherapy is uncommon for other types of stage 1 cancers. Stage 2 and 3 cancers with a progressively poorer prognosis and greater risk of recurrence are generally treated with surgery (lumpectomy or mastectomy with or without lymph node removal), chemotherapy (plus trastuzumab for HER2 positive cancers) and sometimes radiation (particularly following large cancers, multiple positive nodes or lumpectomy). Stage 4, metastatic cancer, (i.e. spread to distant sites) has poor prognosis and is managed by various combination of all treatments from surgery, radiation, chemotherapy and targeted therapies. 10 year survival rate is 5% without treatment and 10% with optimal treatment.

Drugs used after and in addition to surgery are called adjuvant therapy. Chemotherapy or other types of therapy prior to surgery are called neoadjuvant therapy.

There are currently three main groups of medications used for adjuvant breast cancer treatment: hormone blocking therapy, chemotherapy, and monoclonal antibodies.

Hormone blocking therapy: Some breast cancers require estrogen to continue growing. They can be identified by the presence of estrogen receptors (ER positive) and progesterone receptors (PR positive) on their surface (sometimes referred to together as hormone receptors). These ER positive cancers can be treated with drugs that either block the receptors, e.g. tamoxifen (Nolvadex®), raloxifene, ormeloxifene or toremifene, or alternatively block the production of estrogen with an aromatase inhibitor, e.g. anastrozole (Arimidex®), exemestane, or letrozole (Femara®). Additionally, there are EGFR inhibitors such as Iressa®/Gefitinib, and Lapatinib.

Anitprogestin agents can also be used in therapy. An antiprogestin (a hormone antagonist) is a substance that prevents cells from making or using progesterone (a hormone that plays a role in the menstrual cycle and pregnancy). Antiprogestins may stop some cancer cells from growing. Antiprogestins include, but are not limited to, onapristone, lonaprisan, PF-02413873, lilopristone, ORG2058, mifepristone (RU486), asoprisnil, telapristone, ulipristal, aglepristone, ZM172406, ZM172405 and ZM150271.

Aglepristone (8S,11R,13S,14S,17R)-11-(4-dimethylaminophenyl)-17-hydroxy-13-methyl-17-[(Z)-prop-1-enyl]-1,2,6,7,8,11,12,14,15,16-decahydrocyclopenta[a]phenanthren-3-one

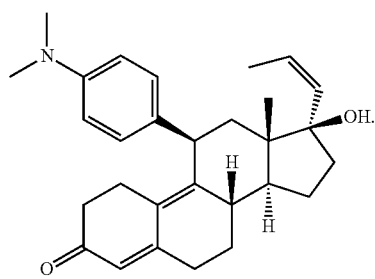

Onapristone, (e.g., (8S,11R,13R,14S,17S)-11-[4-(dimethylamino)phenyl]-17-hydroxy-17-(3-hydroxypropyl)-13-methyl-1,2,6,7,8,11,12,14,15,16-decahydrocyclopenta[a]phenanthren-3-one) has the following chemical structure:

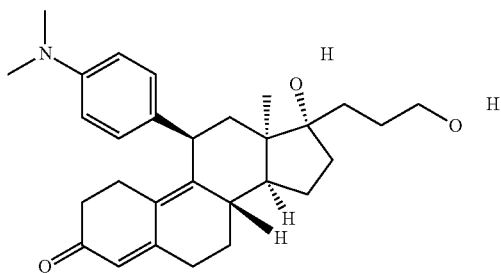

Other anti-progestins include: progestational 3-(6,6-ethylene-17B-hydroxy-3-oxo-17A-pregna-4-ene-17A-YL)propionic acid G-lactones, 3-(6,6-ethylene-17.beta.-hydroxy-3-oxo-17.alpha.-pregna-4-ene-17.alpha.-yl)propionic acid.gamma.-lactone and the following:

Mifepristone (10S,11S,14S,15S,17R)-17-[4-(dimethylamino)phenyl]-14-hydroxy-15-methyl-14-(prop-1-yn-1-yl)tetracyclo[8.7.0.0^{2,7}.0^{11,15}]heptadeca-1,6-dien-5-one

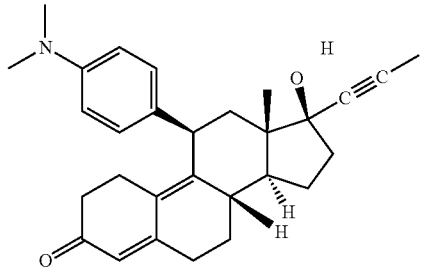

Lilopristone (11-beta,17-beta,17 (z))-ropenyl);estra-4,9-dien-3-one,11-(4-(dimethylamino)phenyl)-17-hydroxy-17-(3-hydroxy-1-p; 11β-[4-(Dimethylamino)phenyl]-17β-hydroxy-17-[(Z)-3-hydroxy-1-propenyl]estra-4,9-dien-3-one

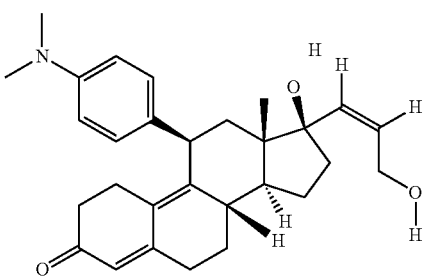

ORG2058 8R,9S,10R,13S,14S,16R,17S)-16-ethyl-17-(2-hydroxyacetyl)-13-methyl-2,6,7,8,9,10,11,12,14,15,16,17-dodecahydro-1H-cyclopenta[a]phenanthren-3-one

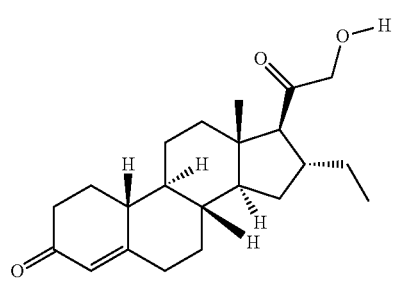

Lonaprisan (8S,11R,13S,14S,17S)-11-(4-acetylphenyl)-17-hydroxy-13-methyl-17-(1,1,2,2,2-pentafluoroethyl)-1,2,6,7,8,11,12,14,15,16-decahydrocyclopenta[a]phenanthren-3-one

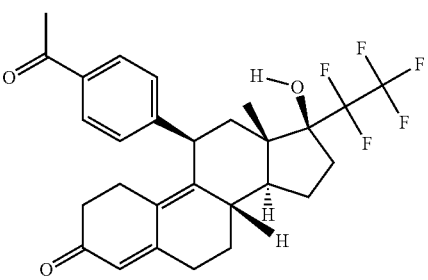 [SMILES: CC(=O)c1ccc([C@H]2C[C@@]3(C)[C@@H](CC[C@@]3(O)C(F)(F)C(F)(F)F)[C@@H]3CCC4=CC(=O)CCC4=C32)cc1]

Asoprisnil (8S,11R,13S,14S,17S)-11-14-[(E)-hydroxyiminomethyl]phenyl]-17-methoxy-17-(methoxymethyl)-13-methyl-1,2,6,7,8,11,12,14,15,16-decahydrocyclopenta[a]phenanthren-3-one

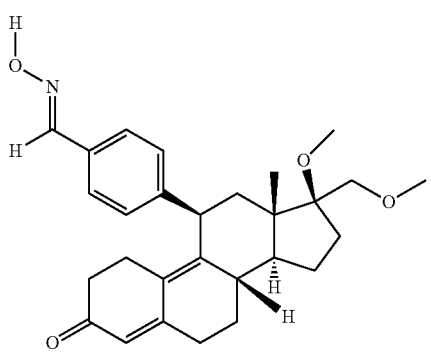 [SMILES: COC[C@]1(OC)CC[C@H]2[C@@H]3CCC4=CC(=O)CCC4=C3[C@@H](c3ccc(/C=N/O)cc3)C[C@@]21C]

Ulipristal (8S,11R,13S,14S,17R)-17-acetyl-11-[4-(dimethylamino)phenyl]-17-hydroxy-13-methyl-1,2,6,7,8,11,12,14,15,16-decahydrocyclopenta[a]phenanthren-3-one

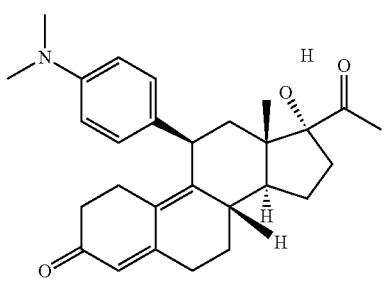

PF-2413873  4-[3-Cyclopropyl-1-(mesylmethyl)-5-methyl-1H-pyrazol-4-yl]oxy,-2,6-dimethylbenzonitrile

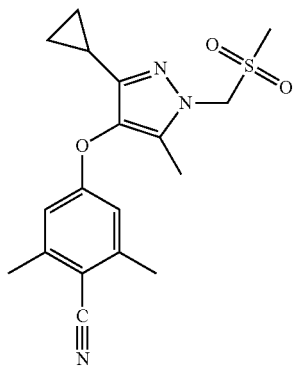 [SMILES: Cc1cc(Oc2c(C3CC3)nn(CS(C)(=O)=O)c2C)cc(C)c1C#N]

Telapristone
[(8S,11R,13S,14S,17R)-11-[4-(Dimethylamino)phenyl]-17-(2-methoxyacetyl)-13-methyl-3-oxo-1,2,6,7,8,11,12,14,15,16-decahydrocyclopenta[a]phenanthren-17-yl]acetate

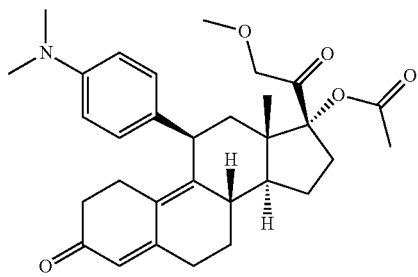

Additional anti-progestins include the following:

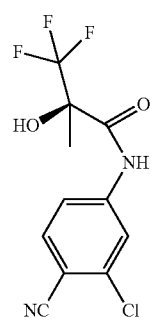

ZM172406

(R)-N-(3-chloro-4-cyanophenyl)-3,3,3-trifluoro-2-hydroxy-2-methylpropanamide

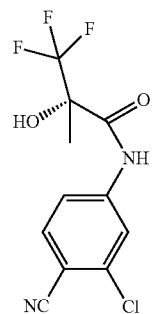

ZM172405

(S)-N-(3-chloro-4-cyanophenyl)-3,3,3-trifluoro-2-hydroxy-2-methylpropanamide

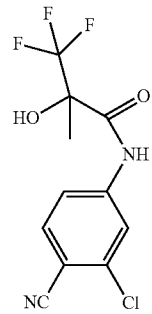

ZM150271

N-(3-chloro-4-cyanophenyl)-3,3,3-trifluoro-2-hydroxy-2-methylpropanamide

The exemplary systems and methods disclosed herein can be used to identify and treat patients suspected of having a malignancy susceptible to growth inhibition by anti-progestins (e.g., onapristone, lonaprisan, mifepristone, PF-02413873, telapristone, lilopristone, ORG2058, apoprisnil, ulipristal, ZM172406, ZM150271, ZM172405 and aglepristone). In one aspect, patients suspected of having a malignancy (cancer) susceptible to growth inhibition with anti-progestins can be treated with anti-progestins. In another aspect, tumors susceptible to treatment with anti-progestins include, but are not limited to, breast, brain, meningiomas, prostate, ovarian, endometrial, uterine sarcomas, uterine leiomyoma, lung, and uterine tissue. In a further aspect, the anti-progestin can be administered to a patient in an amount from about 10 mg to about 200 mg per day. Optionally, an anti-tumor compounds (e.g., everolimus, trastuzumab, T-DM1, anti-HER2 drugs, m-TOR inhibitors, anti-VEGF drugs, anti-EGF drugs, bevacizumab, paclitaxel, docetaxel, taxanes, doxorubicin, liposomal doxorubicin, pegylated liposomal doxorubicin, anthracyclines, anthracenediones, carboplatin, cisplatin, 5-FU, gemcitabine, cyclophosphamide), aromatase inhibitors (anastrozole, letrozole, exemestane, vorozole, formestane and fadrozole), anti-estrogens (fulvestrant), selective estrogen receptor modulators (raloxifene, tamoxifen, toremifene, lasofoxifene, afimoxifene, arzoxifene, and bazedoxifene), androgen receptor blockers (enzalutamide) or inhibitors of 17 α-hydroxylase/C17,20 lyase (abiraterone) may also be administered to the patient concurrently, before, or after treatment with the anti-progestin.

Chemotherapy: Predominately used for stage 2-4 disease, being particularly beneficial in estrogen receptor-negative (ER negative) disease. They are given in combinations, usually for 3-6 months. One of the most common treatments is cyclophosphamide plus doxorubicin (Adriamycin®), known as AC. Most chemotherapy medications work by destroying fast-growing and/or fast-replicating cancer cells either by causing DNA damage upon replication or other mechanisms; these drugs also damage fast-growing normal cells where they cause serious side effects. Damage to the heart muscle is the most dangerous complication of doxorubicin. Sometimes a taxane drug, such as docetaxel, is added, and the regime is then known as CAT; taxane (e.g., docetaxel and paclitaxel) attacks the microtubules in cancer cells. Another common treatment, which produces equivalent results, is cyclophosphamide, methotrexate, and fluorouracil (CMF). Chemotherapy can generally refer to any drug.

Monoclonal antibodies: Trastuzumab (Herceptin®), a monoclonal antibody to HER2, has improved the 5 year disease free survival of stage 1-3 HER2-positive breast cancers to about 87% (overall survival 95%). Trastuzumab, however, is associated with cardiotoxicity and approximately 2% of patients suffer significant heart damage. Other monoclonal antibodies are also undergoing clinical trials. Trastuzumab is only effective in patients with HER2 amplification in their tumors.

Radiotherapy is usually given after surgery to the region of the tumor bed and regional lymph nodes, to destroy microscopic tumor cells that may have escaped surgery. It may also have a beneficial effect on tumor microenvironment. Radiation therapy can be delivered as external beam radiotherapy or as brachytherapy (internal radiotherapy). Conventionally radiotherapy is given after the operation for breast cancer. Radiation can also be given at the time of operation on the breast cancer—intraoperatively. Radiation can reduce the risk of recurrence by 50-66% (½-⅔ reduction of risk).

The molecular factors driving its initiation and progression are not completely understood. A randomized clinical trial by the Women's Health Initiative (WHI) demonstrated that hormone replacement therapy (HRT), containing estrogens and progestins (but not estrogens alone), significantly increased the risk of developing invasive breast cancer in post-menopausal women (Chlebowski et al., 2003; LaCroix et al., 2011). A similar conclusion was made from the Million Women observational study (Million Women Study Collaborators, 2003). These findings resulted in dramatically fewer prescriptions for HRT and, as a result, breast cancer incidence dropped considerably (Chlebowski et al., 2009). Further analysis of the WHI data demonstrated that women prescribed HRT containing estrogens alone experienced a reduced risk of developing invasive breast cancer (Anderson et al., 2012; LaCroix et al., 2011). PR expression is traditionally used as a clinical indicator of estrogen receptor (ER) function (i.e. PR is an ER target gene). However, while controversial, this surprising epidemiological evidence provides a strong rationale for further investigation of the unique actions of progesterone receptors (PRs) as mediators of breast cancer initiation and early progression (reviewed in (Lange, 2008)).

Classically, PRs are defined as ligand-activated transcription factors that bind target gene promoters or enhancers as dimers capable of recruiting coregulatory molecules required for efficient transcription. More recently, it has become well recognized that protein kinases are rapidly activated by steroid hormones (as in response to peptide growth factors). Indeed, phosphorylation events provide regulatory inputs to PR action (reviewed in (Daniel et al., 2009) and discussed below). A few mutations in PR have been linked to cancer risk; these appear to primarily alter PR expression levels rather than impact PR transcriptional activity (De Vivo et al., 2002; Pooley et al., 2006; Terry et al., 2005). Two PR protein isoforms, PR-A and PR-B, are co-expressed in breast tissues. PR-B is the full-length receptor, containing 164 amino acids at the N-terminus (termed the B-upstream segment or BUS) that are absent from PR-A. Both isoforms are heavily post-translationally modified (phosphorylation, ubiquitination, acetylation). PR N-termini contain key regulatory phosphorylation sites (e.g. Ser294) as well as a SUMOylation site (Lys388) investigated herein. PR-B (see, for example, NCBI database as accession number NM_000926.4 (GI:160358783)), but not PR-A (see, for example, NCBI database as accession number NM_001202474.1 (GI:321117149)), is phosphorylated on Ser294 in cell culture and in vivo (Clemm et al., 2000). Upon ligand binding, both PR isoforms are rapidly (15 min) SUMOylated at Lys388 (Daniel et al., 2007a). SUMOylation occurs via the covalent attachment of a small ubiquitin-like modifier (SUMO) peptide (~11.5 kD) to lysine residues of substrate molecules, primarily at consensus SUMOylation motifs (IKxE) through an ATP-dependent enzymatic (three step) mechanism, similar to that of ubiquitination (Melchior, 2000). Substrate SUMOylation often alters protein-protein interactions, subcellular location, protein stability (i.e. it can oppose ubiquitination), and/or enzyme or transcriptional activities (Geiss-Friedlander and Melchior, 2007).

Recently, Daniel et al. discovered that PR-B phosphorylation at Ser294, in response to activated mitogen activated protein kinases (MAPKs) or cell cycle-dependent protein kinase-two (CDK2), prevents progestin-induced rapid SUMOylation at Lys388 (Daniel et al., 2007a; Daniel and Lange, 2009). Additionally, Ser294 phosphorylation-induced antagonism of PR SUMOylation derepressed (activated) PR transcriptional activity at selected breast cancer-associated gene promoters, namely HBEGF (Daniel et al., 2007a), STC1 and IRS1 (Daniel and Lange, 2009); phospho-PR-dependent upregulation of the breast cancer-associated drivers, STC1 and IRS, occurred in the absence of progestins (Daniel and Lange, 2009). Promoter structure (i.e. the number of hormone response elements) can be a determinant of reporter-gene promoter recognition by SUMOylated glucocorticoid receptors (GRs) (Iniguez-Lluhi and Pearce, 2000), while much less is known about how steroid receptor SUMOylation alters the regulation of endogenous genes (i.e. in chromatin). To date, only a few endogenous genes have been shown to be sensitive to PR SUMOylation (Daniel et al., 2007a; Daniel and Lange, 2009). It is herein disclosed that PR acts as a sensor for activated mitogenic protein kinases (i.e. MAPKs and CDK2) frequently elevated in human breast cancer; under the influence of elevated Ser294 phosphorylation, genes that are sensitive to (i.e. normally repressed by) PR SUMOylation may instead cooperate to drive breast cancer cell proliferation and pro-survival signaling. A phospho-PR (SUMO-deficient) gene signature can identify a subset of human breast cancer patients likely to respond to endocrine therapies that contain a selective antiprogestin.

Herein, mechanisms of PR promoter selectivity related to dynamic post-translational events (i.e. PR Ser294 phosphorylation coupled to Lys388 deSUMOylation) are addressed. Whole genome expression analysis was employed to identify genes that are differentially regulated by wild-type (WT) and SUMO-deficient (K388R) PR-B and the mechanisms responsible for altered PR promoter selectivity was explored. The findings implicate SUMO-deficient phospho-PR-B in the selective regulation of genes important for breast cancer cell proliferation and pro-survival, and suggest that phosphorylated and deSUMOylated PRs may be important drivers of the ERBB2-positive phenotype associated with rapid (luminal) breast cancer tumor progression.

Gene Expression Profile (Markers) and Determination of Gene Expression Profiles

The expression of certain genes has been demonstrated herein to be predictive of breast cancer treatment with antiprogestins. These genes include the following (or those homologous thereto):

TABLE 1a

| Gene | Up or Down Regulated in KR | WT (mean ± SD) n = 5 | KR (mean ± SD) n = 5 | P value α = 1.06E-06 | Fold Change (KR/WT) or -(WT/KR) | ROCAUC | Probe ID | Accession | Probe Sequence |
|---|---|---|---|---|---|---|---|---|---|
| KBTBD11 | Down | 9.303 ± 0.050 | 7.787 ± 0.097 | 1.24E-09* | -1.195* | 1.00 0* | ILMN_ 1784630 | NM_ 014867.1 | GGTAAACTACACCTGTTGAAGGCCAA GTTCAGGGCAGCTGTTGTGATCTG SEQ ID NO: 1 |
| VCX | Up | 8.941 ± 0.115 | 10.568 ± 0.064 | 3.27E-09* | 1.182* | 1.00 0* | ILMN_ 1684886 | NM_ 013452.2 | GAACCACTGAGTCAGGAGAGCCAGGT GGAGGAACCACCGAGTCAGGAGAG SEQ ID NO: 2 |
| RBPMS2 | Down | 9.062 ± 0.089 | 7.642 ± 0.076 | 3.65E-09* | -1.186* | 1.00 0* | ILMN_ 1808238 | NM_ 194272.1 | GGCCATTTCAGACTTGGGAGATGAGG CGGCTGTTGTCATTGCTGATCCTG SEQ ID NO: 3 |
| CHN2 | Up | 7.861 ± 0.096 | 9.200 ± 0.065 | 5.59E-09* | 1.170* | 1.00 0* | ILMN_ 2403237 | NM_ 004067.2 | CCATTGGCACAGGGAGGTTTGACCTC TTCCCTGCTATTATCCCTCCTCCC SEQ ID NO: 4 |
| PLA2G4B | Down | 9.219 ± 0.043 | 8.168 ± 0.090 | 1.05E-08* | -1.129* | 1.00 0* | ILMN_ 1697629 | NM_ 005090.2 | GTGTAATCACCCAAAACCCCCGGCC TGTGCCTGTTTTCCCTTCTGCGCT SEQ ID NO: 5 |
| FLJ12684 | Down | 8.129 ± 0.058 | 7.309 ± 0.074 | 4.95E-08* | -1.112* | 1.00 0* | ILMN_ 2072622 | NM_ 024534.4 | AGCAGGTCTTACCGAGAATTCAGCTG CCAAAACCCTCCTCTGAGTGTTCC SEQ ID NO: 6 |
| AFAP1L2 | Up | 6.521 ± 0.037 | 7.297 ± 0.081 | 4.97E-08* | 1.119* | 1.00 0* | ILMN_ 2404917 | NM_ 032550.2 | GGGTCACGTGTCTTTGGTGAGTGAGA AGACCTAAACTCCTGGCCATCATC SEQ ID NO: 7 |
| PXMP4 | Up | 10.015 ± 0.123 | 11.066 ± 0.062 | 1.39E-07* | 1.105* | 1.00 0* | ILMN_ 1664025 | NM_ 007238.4 | ACGCATTCCTGGCGGCCTTCCTCGGG GGTATCCTGGTGTTTGGAGAAAAC SEQ ID NO: 8 |
| SH2D4A | Down | 8.671 ± 0.065 | 7.777 ± 0.120 | 4.79E-07* | -1.115* | 1.00 0* | ILMN_ 1679322 | NM_ 022071.2 | ACCAGCAGAAGCCAGCAGAGAGGCAT GGGACAGGTTCCCCACAAGCCTTA SEQ ID NO: 9 |
| THY1 | Up | 6.602 ± 0.063 | 7.406 ± 0.111 | 6.27E-07* | 1.122* | 1.00 0* | ILMN_ 1779875 | NM_ 006288.2 | CTGAGGCAAGCCATGGAGTGAGACCC AGGAGCCGGACACTTCTCAGGAAA SEQ ID NO: 10 |
| RASD2 | Down | 7.827 ± 0.095 | 6.865 ± 0.121 | 6.56E-07* | -1.140* | 1.00 0* | ILMN_ 2170209 | NM_ 014310.3 | TCTCACCCAGGCACAGCCCCGCCACC ATGGATCTCCGTGTACACTATCAA SEQ ID NO: 11 |
| CLDN8 | Down | 8.325 ± 0.085 | 7.534 ± 0.094 | 6.68E-07* | -1.105* | 1.00 0* | ILMN_ 1746676 | NM_ 199328.1 | TGTCAAGGGGCTTTGCATTCAAACTG CTTTTCCAGGGCTATACTCAGAAG SEQ ID NO: 12 |
| ZNF26 | Up | 8.759 ± 0.168 | 10.017 ± 0.128 | 9.61E-07* | 1.144* | 1.00 0* | ILMN_ 1691798 | NM_ 019591.2 | TGGGGTGCTTCCTGTGGTAGTGTCTT TCAGGTATCCGTTCCACTAGCTAC SEQ ID NO: 13 |
| CDH10 | Up | 6.605 ± 0.041 | 9.251 ± 0.638 | 1.50E-05 | 1.401* | 1.00 0* | ILMN_ 1791270 | NM_ 006727.2 | AGCAACCTCACAAACAAGCCGCTTCT GTTAGGTACATGTCCTGCCCTTGC SEQ ID NO: 14 |

TABLE 1a-continued

| Gene | Up or Down Regulated in KR | WT (mean ± SD) n = 5 | KR (mean ± SD) n = 5 | P value α = 1.06E-06 | Fold Change (KR/WT) or -(WT/KR) | ROCAUC | Probe ID | Accession | Probe Sequence |
|---|---|---|---|---|---|---|---|---|---|
| ZNF812 | Up | 7.883 ± 0.221 | 9.730 ± 0.592 | 1.82E-04 | 1.234* | 1.000* | ILMN_3305614 | XM_001719513.1 | CTCACCCCTTAATGTTCACCTGCAAA CTCATACCAGAGAGAAAGCCCTCA SEQ ID NO: 15 |

Table 1a. Top 15 most significant genes with differential expression between progestin-stimulated KR and WT cells. (*) Statistically significant according to the criteria of the respective method.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGGC share 50% homology.

As used herein, "homology" is used synonymously with "identity." The determination of percent identity between two nucleotide or amino acid sequences can be accomplished using a mathematical algorithm. For example, a mathematical algorithm useful for comparing two sequences is the algorithm of Karlin and Altschul (1990), modified as in Karlin and Altschul (1993). This algorithm is incorporated into the NBLAST and XBLAST programs of Altschul, et al., and can be accessed, for example at the National Center for Biotechnology Information (NCBI) world wide web site. BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. Alternatively, PSI-Blast or PHI-Blast can be used to perform an iterated search which detects distant relationships between molecules and relationships between molecules which share a common pattern. When utilizing BLAST, Gapped BLAST, PSI-Blast, and PHI-Blast programs, the default parameters of the respective programs (e.g., XBLAST and NBLAST) can be used.

The percent identity between two sequences can be determined using techniques similar to those described above, with or without allowing gaps. In calculating percent identity, typically exact matches are counted.

As used herein, a "substantially homologous amino acid sequences" or "substantially identical amino acid sequences" includes those amino acid sequences which have at least about 92%, or at least about 95% homology or identity, including at least about 96% homology or identity, including at least about 97% homology or identity, including at least about 98% homology or identity, and at least about 99% or more homology or identity to an amino acid sequence of a reference antibody chain Amino acid sequence similarity or identity can be computed by using the BLASTP and TBLASTN programs which employ the BLAST (basic local alignment search tool) 2.0.14 algorithm. The default settings used for these programs are suitable for identifying substantially similar amino acid sequences for purposes of the present invention.

As used herein, the term "conservative amino acid substitution" is defined herein as an amino acid exchange within one of the following five groups:

I. Small aliphatic, nonpolar or slightly polar residues:
Ala, Ser, Thr, Pro, Gly;
II. Polar, negatively charged residues and their amides:
Asp, Asn, Glu, Gln;
III. Polar, positively charged residues:
His, Arg, Lys;
IV. Large, aliphatic, nonpolar residues:
Met Leu, Ile, Val, Cys
V. Large, aromatic residues:
Phe, Tyr, Trp "Substantially homologous nucleic acid sequence" or "substantially identical nucleic acid sequence" means a nucleic acid sequence corresponding to a reference nucleic acid sequence wherein the corresponding sequence encodes a peptide having substantially the same structure and function as the peptide encoded by the reference nucleic acid sequence; e.g., where only changes in amino acids not significantly affecting the peptide function occur. In one embodiment, the substantially identical nucleic acid sequence encodes the peptide encoded by the reference nucleic acid sequence. The percentage of identity between the substantially similar nucleic acid sequence and the reference nucleic acid sequence is at least about 50%, 65%, 75%, 85%, 92%, 95%, 99% or more. Substantial identity of nucleic acid sequences can be determined by comparing the sequence identity of two sequences, for example by physical/chemical methods (i.e., hybridization) or by sequence alignment via computer algorithm.

Suitable nucleic acid hybridization conditions to determine if a nucleotide sequence is substantially similar to a reference nucleotide sequence are: 7% sodium dodecyl sulfate SDS, 0.5 M NaPO4, 1 mM EDTA at 50° C. with washing in 2× standard saline citrate (SSC), 0.1% SDS at 50° C.; preferably in 7% (SDS), 0.5 M NaPO4, 1 mM EDTA at 50° C. with washing in 1× SSC, 0.1% SDS at 50° C.; preferably 7% SDS, 0.5 M NaPO4, 1 mM EDTA at 50° C. with washing in 0.5×SSC, 0.1% SDS at 50° C.; and more preferably in 7% SDS, 0.5 M NaPO4, 1 mM EDTA at 50°

C. with washing in 0.1×SSC, 0.1% SDS at 65° C. Suitable computer algorithms to determine substantial similarity between two nucleic acid sequences include, GCS program package. The default settings provided with these programs are suitable for determining substantial similarity of nucleic acid sequences for purposes of the present invention.

Determination of Expression Levels

In one embodiment, the expression of the nucleic acid, such as mRNA of the genes of interest is determined. The expression levels of preselected mRNAs can be identified and/or quantified by any of a variety of techniques including, for instance, in situ hybridization, Northern blot, nucleic acid amplification techniques (e.g., PCR, quantitative PCR, the ligase chain reaction, etc.), RNA Seq and microarray analysis. Levels of mRNA can be quantitatively measured by Northern blotting. A sample of RNA is separated on an agarose gel and hybridized to a radio-labeled RNA probe that is complementary to the target sequence. The radio-labeled RNA is then detected by an autoradiograph.

Another approach for measuring mRNA abundance is reverse transcription quantitative polymerase chain reaction. RT-PCR first generates a DNA template from the mRNA by reverse transcription, which is called cDNA. This cDNA template is then used for qPCR where the change in fluorescence of a probe changes as the DNA amplification process progresses. With a standard curve qPCR can produce an absolute measurement such as number of copies of mRNA, typically in units of copies per nanoliter of homogenized tissue or copies per cell. qPCR is very sensitive (detection of a single mRNA molecule is possible).

Another approach is to individually tag single mRNA molecules with fluorescent barcodes (nanostrings), which can be detected one-by-one and counted for direct digital quantification (Krassen Dimitrov, NanoString Technologies). Also, "tag based" technologies like Serial analysis of gene expression (SAGE), which can provide a relative measure of the cellular concentration of different mRNAs, can be used.

Also, DNA microarrays can be used to determine the transcript levels for many genes at once (expression profiling). Recent advances in microarray technology allow for the quantification, on a single array, of transcript levels for every known gene in several organism's genomes, including humans.

Computer/Processor

The detection, prognosis and/or diagnosis method can employ the use of a processor/computer system. For example, a general purpose computer system comprising a processor coupled to program memory storing computer program code to implement the method, to working memory, and to interfaces such as a conventional computer screen, keyboard, mouse, and printer, as well as other interfaces, such as a network interface, and software interfaces including a database interface find use one embodiment described herein.

The computer system accepts user input from a data input device, such as a keyboard, input data file, or network interface, or another system, such at the system interpreting, for example, the microarray or PCR data, and provides an output to an output device such as a printer, display, network interface, or data storage device. Input device, for example a network interface, receives an input comprising detection of the proteins/nucleic acids described herein and/or quantification of those compounds. The output device provides an output such as a display, including one or more numbers and/or a graph depicting the detection and/or quantification of the compounds.

Computer system is coupled to a data store which stores data generated by the methods described herein. This data is stored for each measurement and/or each subject; optionally a plurality of sets of each of these data types is stored corresponding to each subject. One or more computers/processors may be used, for example, as a separate machine, for example, coupled to computer system over a network, or may comprise a separate or integrated program running on computer system. Whichever method is employed these systems receive data and provide data regarding detection/diagnosis in return.

EXAMPLES

The following examples are provided in order to demonstrate and further illustrate certain embodiments and aspects of the present invention and are not to be construed as limiting the scope thereof.

Example I

Phosphorylated and SUMO-Deficient Progesterone Receptors Drive Proliferative Gene Signatures During Breast Cancer Progression Materials and Methods Progesterone Receptor Expression in Human Breast Tumor Samples De-identified human breast tumor samples were obtained from the University of Minnesota Tissue Procurement Facility's Biological Materials Procurement Network (Bio-Net) for protein and mRNA analysis. Frozen tissue samples were derived from patients diagnosed with either ductal carcinoma, infiltrating ductal carcinoma, lobular carcinoma, or metastatic carcinoma. Specimens were analyzed by the University of Minnesota clinical pathology department and scored for estrogen receptor (ER) and progesterone receptor (PR) expression using standard clinical histological methods. Tumor samples were harvested individually for protein or mRNA using standard methods (frozen tissue grinding, RIPA buffer, tri-reagent), and total PR, phospho-Ser294 PR, and ERK1/2 protein expression levels were measured by western blotting (described below). All specimens were obtained from patients who had provided informed consent regarding the use of their tissue samples for research purposes and approval from University of Minnesota Institutional Review Board (IRB).

Cell Culture, Expression Vectors and Western Blotting

T47Dco parental cell lines were characterized previously (Horwitz et al., 1982). T47D cells stably expressing PR were created by molecular cloning of cDNAs encoding either WT, K388R, S294A, or K388R/S294A PR into a pIRES-neo3 expression vector (Clontech, catalog #631621), followed by transfection of vectors into T47D-Y cells (Sartorius et al., 1994) using FuGENE HD (Roche, catalog #04709713001). Single-cell clones were expanded under high G418 selection (500 ug/ml) and maintained in low G418 selection (200 ug/ml) (EMD Chemicals, catalog #345810). These cells were maintained in complete minimal essential medium (cMEM) supplemented with 5% fetal bovine serum (FBS), 1% non-essential amino acids (NEAA), 1% penicillin/streptomycin, 6 ng/ml insulin (CellGro, catalog #10-010-CV). T47D cells expressing inducible PR were described previously (Hagan et al., 2011). Inducible PR expression was achieved by adding AP21967 ($10^{-9}$ M, Ariad Pharmaceuticals, Cambridge, Mass.) to cell culture medium for a minimum treatment time of 2 d. MCF-7 cell lines expressing PR were created by transfection of pIRES-neo3 vectors containing cDNA inserts encoding either WT or KR PR into cells using FuGENE HD. Single-cell clones were expanded under high G418 selection and maintained in low G418 selection. MCF-7 cells were maintained in DMEM (Dulbecco's modification of Eagle's medium, CellGro, catalog #10-013-CV) supplemented with 5% FBS, 1% penicillin/streptomycin. BT-474 cells (ATCC, Manassas, Va.) were maintained in RPMI 1640 medium (Gibco, catalog #11875) supplemented with 10% FBS, 1% penicillin/streptomycin. SDS-PAGE was performed using 8% gels and western blotting analysis was performed as previously described (Daniel et al., 2007a). For antibody information, see FIG. 5.1.

Gene Expression Profiling

T47D cells stably expressing pIRES-neo3 empty vector, WT or KR PR were serum starved in modified IMEM (Gibco, catalog #A10488) for 1 day, treated with R5020 ($10^{-8}$ M) or vehicle control for 6 h before RNA extraction using a RNeasy kit (QIAgen, catalog #74104). Six h of progestin treatment allowed for substantial PR-dependent gene expression as compared to prior studies (Jacobsen et al., 2005; Richer et al., 2002). DNase I treated (QIAgen, catalog #79254) RNA samples from duplicate experiments were prepared for expression analysis using the Illumina HT-12v4 bead chip platform according to manufacture's protocols. Data were analyzed within R software using the Bioconductor (Gentleman et al., 2004) package called lumi where raw intensities were $\log_2$ transformed and quantile normalized. Differentially expressed genes were analyzed using the limma package, where empirical Bayes was used to better estimate the variance of the genes. Gene expression data presented contain $\log_2$ normalized intensities and biological comparisons presented (e.g. R5020/vehicle) contain $\log_2$ fold change with the Benjamini and Hochberg (BH) adjusted P value (Benjamini and Hochberg, 1995). To generate the heat map in FIG. 1C, unsupervised hierarchical clustering of genes was carried out using heatmap. 2 function in the R package gplots. Clustering was performed using Euclidean distance and complete linkage. Rows were scaled to have mean zero and standard deviation equal to one.

Gene expression profiles in T47D cells expressing inducible PR were measured using the Affymetrix microarray platform. PR expression was induced with AP21967 ($10^{-9}$ M) for 2 d, cells were serum starved in modified IMEM for 1 day and treated with R5020 ($10^{-8}$ M) or vehicle control for 6 h before RNA extraction using an RNeasy kit. DNase I treated samples were prepared for expression analysis using the Affymetrix U133A 2.0 microarrays according to manufacture's protocols. Raw Affymetrix CEL files were processed and normalized within R using the Bioconductor (Gentleman et al., 2004) packages, affy and affyQCReport. Data were normalized using the Robust Multi-array Average (Irizarry et al., 2003) algorithm within the affy package. Wilcoxon-signed rank tests as part of the MAS 5.0 algorithm (also included in the affy package) were used to determine presence/absence calls for all probe sets (Liu, 2004). Normalized expression levels for selected pairs of conditions were computed as $\log_2$ ratios. All gene expression data is available in the NCBI Gene Expression Omnibus (GEO) database (accession number: GSE34149, www.ncbi.nlm.nih.gov/geo/query/acc.cgi?acc=GSE34149).

Gene expression profiles in T47D cell lines treated with antiprogestins were obtained using identical methods as described above, except for these notable differences. After serum starvation, cells stably expressing empty vector, WT, or KR PR were treated for 6 hours under one of eight possible conditions: (1) ethanol (vehicle control), (2) progesterone ($10^{-8}$ M), (3) RU486 ($10^{-7}$ M), (4) aglepristone ($10^{-7}$ M), (5) onapristone ($10^{-7}$ M), (6) RU486 ($10^{-7}$ M) plus progesterone ($10^{-8}$ M), (7) aglepristone ($10^{-7}$ M) plus progesterone ($10^{-8}$ M), or (8) onapristone ($10^{-7}$ M) plus progesterone ($10^{-8}$ M). Gene expression levels were measured, normalized, analyzed, and heat maps were generated using the methods described above.

Identification of Genetic Markers in Tumors Driven by Activated PR

Raw microarray data from two independent microarray experiments (both performed using the Illumina HT-12v4 platform described above) were combined and normalized together within R software using the Bioconductor (Gentleman et al., 2004) package called lumi where raw intensities were log 2 transformed and quantile normalized.

Sample Sizes & Composition: For the first analysis, two KR cell replicates were used that had been stimulated with R5020 a synthetic progestin in the first experiment and three KR cell replicates that had been stimulated with progesterone in the second experiment. The same was accomplished regarding the corresponding WT cell replicates. Pertaining to the first analysis, therefore, a sample size of n=5 was used for each of the two groups (KR & WT). Regarding the second analysis, we used three KR cell replicates that had been co-treated with progesterone plus onapristone in the second experiment; and we used three WT cell replicates that had been co-treated with progesterone plus onapristone also in the second experiment (n=3 for each of the two groups). Regarding the third analysis, we used three KR cell replicates that had been co-treated with progesterone plus RU486 in the second experiment; and we used three WT cell replicates that had been co-treated with progesterone plus RU486 also in the second experiment (n=3 for each of the two groups). Regarding the fourth analysis, three KR cell replicates was used that had been co-treated with progesterone plus onapristone; and three WT cell replicates were used that had been treated with vehicle control (ethanol) (n=3 for each of the two groups). Regarding the fifth analysis, three WT cell replicates was used that had been co-treated with progesterone plus onapristone; and three WT cell replicates were used that had been treated with vehicle control (ethanol) (n=3 for each of the two groups).

Control Genes In order to assess the quality of the processed (normalized) data, the following list of control genes was used: TBP, GAPDH, ACTB, TRAP1, PPIB, FPGS, EEF1A1, UBC, TXN, B2M, HMBS, and FARP1. In order to account for the well-documented shortcomings of microarray technology, all probes in this chip (Illumina HT-12v4) that target the aforementioned control genes were identified and utilized. The following numbers in the parentheses indicate the number of different probes in this chip that target the particular control gene: TBP (1), GAPDH (3), ACTB (3), TRAP1 (1), PPIB (1), FPGS (3), EEF1A1 (4), UBC (3), TXN (2), B2M (2), HMBS (3), and FARP1 (4).

Statistical Methods: To assess statistical significance, the following three different and independent methods were used.

1) P-Value.

Independent t-Test were used for parametric gene variables (both normality and equality of variance conditions were met); the Aspin-Welch unequal-variance test (AW) for gene variables that met the normality condition, but not the equality of variance condition; and the Mann-Whitney U test (MW) for the non-parametric gene variables, i.e., for those variables that i) the normality condition was not met or ii)

the normality and the equality of variance conditions were not met. Taking into account that there are 47,231 probe sets in the Illumina HT-12v4 chip, and using the Bonferroni correction, the significance level for the entire study was set at $\alpha=1.06\times10$-6. Therefore, in order for any variable to be deemed significant according to the P-value method, the following condition must be met: $P<\alpha$. Regarding the Mann-Whitney U test (MW), if a non-parametric variable had no ties (a subject from one group having the same expression value as a subject from the other group), the exact probability was used; otherwise, the approximated probability with correction was used.

2) Fold Change (FC).

For all gene variables, fold change (FC) was defined as the mean expression value of the KR group over the mean expression value of the WT group in the case where the former is greater than the latter (over-expression), and the statistical significance was set at $FC\geq1.10$, which represents a change $\geq10\%$ in a log 2 scale. In the case where the mean expression value of the KR group is less than the mean expression value of the WT group (under-expression), the FC was defined as the negative ratio of the mean expression value of the WT group over the mean expression value of the KR group, and the statistical significance was set at $FC\leq-1.10$, which also represents a change $\geq10\%$ in a log 2 scale. According to this method, therefore, a gene variable must have $|FC|\geq1.10$ in order to be deemed statistically significant.

3) ROC Curve Analysis.

ROC curve analysis was performed on all gene variables in order to assess their discriminating power with respect to the two groups. In order to offset, as much as possible, the effects of small sample sizes, the statistical significance was set at ROC AUC=1.00. A variable with an ROC AUC=1.00 has a perfect discriminating power, that is to say, the two groups are completely separate with respect to that variable, and there is no overlap between the two groups. (AUC: Area Under the Curve). The empirical ROC curves were used for this analysis.

Overall Criteria of Statistical Significance: Incorporating the three aforementioned independent methods of statistical significance assessment, the overall significance criterion was set as follows: in order for any variable to be included in the final list of the most significant variables, it would have to have i) $P<1.06\times10$-6, ii) $|FC|\geq1.10$, and iii) ROC AUC=1.00. Furthermore, in order to minimize the number of false negatives in the case of the first method, is was deemed statistically significant a given variable if it failed to meet the criterion of the first method ($P<1.06\times10$-6), but it met the criteria of the other two methods, and only if its $|FC|\geq1.20$, which represents a change of more than 20% in a log 2 scale.

Probe Multiplicity: All gene variables that fulfilled all three criteria of statistical significance and were included in the final list were investigated for the possibility of multiple probes targeting that same gene variable. In the event there were multiple probes (more than one) targeting a given gene variable, all probes were assessed for statistical significance. If the majority of those probes met all three criteria of significance, then the given gene variable was retained in the final list of the most significant variables. In the case of a tie, whereby half of the probes were determined to be significant (by all three methods) and the other half were determined not to be so, then the given gene variable was excluded from the final list.

RT-qPCR

For reverse transcription quantitative polymerase chain reaction (RT-qPCR) assays, $5\times10^5$ cells/well were plated in 6-well dishes, serum starved in modified IMEM for 1 day before treatments (see individual figures). RNA was extracted using TriPure reagent (Roche, catalog #11667157001) and cDNA was created using the Transcriptor cDNA first-strand cDNA synthesis kit (Roche, catalog #04897030001). Relative expression levels were determined by qPCR assays performed on a Roche LightCycler II using SYBR green master-mix (Roche, catalog #04887352001). Target gene quantification levels were normalized to the expression of standard housekeeper genes: TBP, ACTB, and/or GAPDH. For cells expressing inducible PR, the protocol was the same as above, except prior to ligand treatments, the cells were induced with AP21967 ($10^{-9}$ M) for 2 d.

For RT-qPCR assays involving epidermal growth factor (EGF) treatment, cells were plated at $5\times10^5$ cells/well in 6-well dishes and serum starved for 2 days in modified IMEM. Cells were pre-treated with 100 ng/ml EGF (Sigma, catalog #E9644) before treatment with R5020 ($10^{-8}$ M).

For experiments using MEK inhibitors, BT-474 cells were plated in E-well dishes at $5\times10^5$ cells/well. One day later, the cells were washed and serum starved in modified IMEM for 1d. These cells were pre-treated with the MEK inhibitor U0126 (5 uM, EMD Chemicals, catalog #662005) for 30 min R5020 ($10^{-8}$ M) and/or RU486 ($10^{-7}$ M) was then added to cell culture wells for 6 h before RNA/protein isolation and RT-qPCR/western blotting was performed, as described above. PCR primer sets used in this study are provided in FIG. 5.1.

Ingenuity Pathway Analysis

Ingenuity Pathway Analysis (IPA) was used to compare two distinct gene lists: those upregulated by progestin in T47D cells expressing WT PR compared to genes upregulated by progestin in cells expressing SUMO-deficient PR (+R5020/−R5020 $\log_2$ fold change >1.0, BH adjusted P<0.01). These gene lists were uploaded into the IPA software where a core analysis was completed to determine the association of each gene with various biological functions or network pathways. IPA comparison analyses were used to reveal whether or not cells expressing WT or KR PR upregulated functionally distinct pathways. Analyses were scored based on significance (the BH adjusted P value, corrected for multiple hypothesis testing) and the threshold for a gene list to be significantly involved in a particular biological function was P<0.05 (or $-\log_{10}$(BH adjusted P value)>1.30).

Identification of PR Expression Metagenes

Figure 5A:
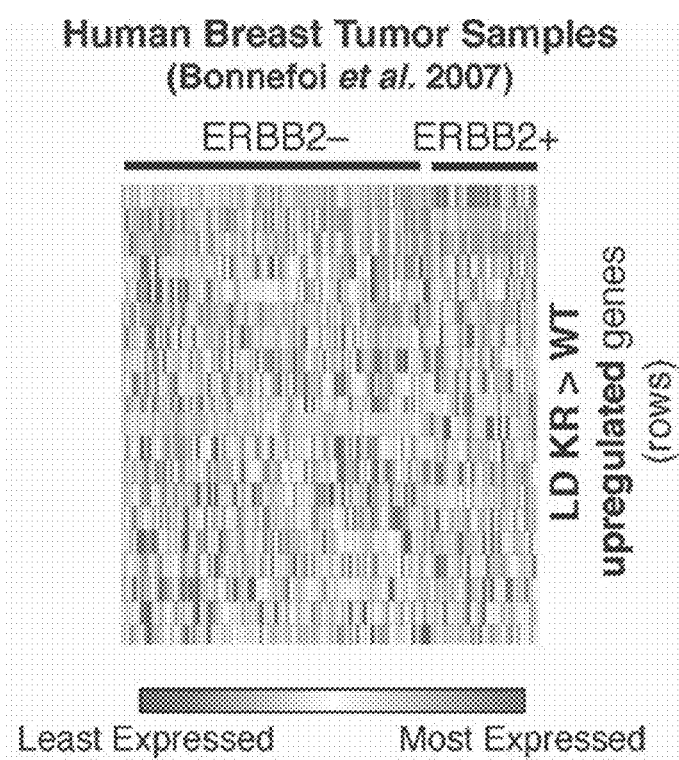
Figure 5C:
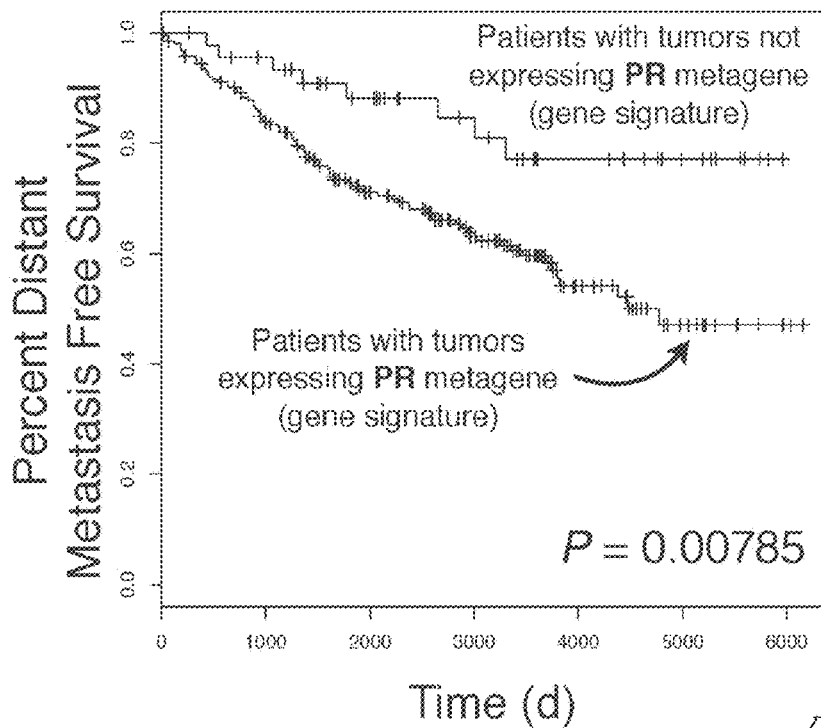
Figure 5D:
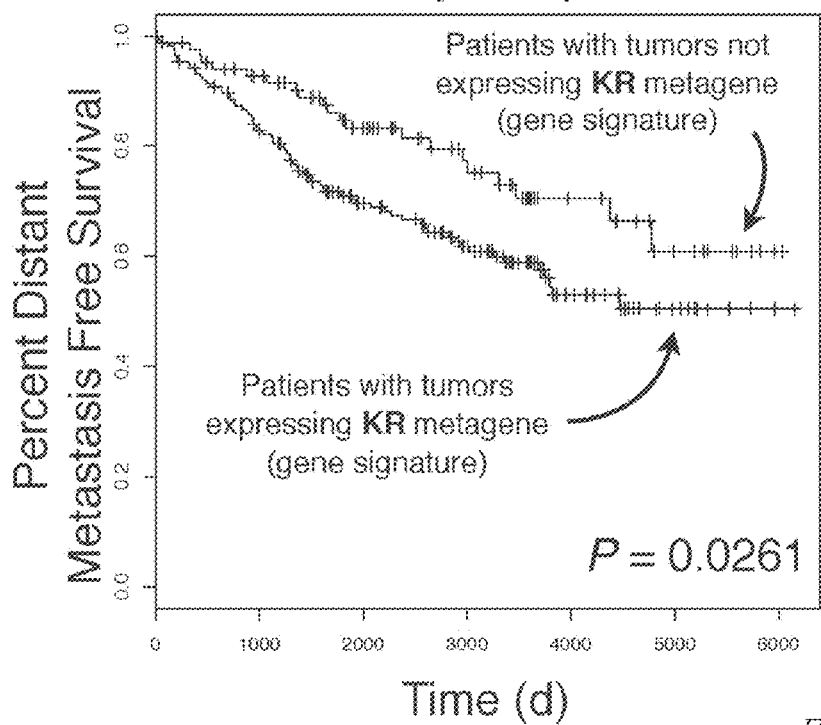

Metagene analysis was conducted using gene expression microarray data from cell lines constitutively expressing empty vector, WT PR, or K388R PR, and treated with either vehicle or R5020 (FIG. 5C-D). A strategy of identifying metagenes within each sample was employed using non-negative matrix factorization (Gaujoux and Seoighe, 2010). This strategy facilitated identification of metagenes and application to other datasets. To limit the study to genes under high variance and to limit the number of probes used in calculating the metagene fit, probes were considered for metagene analysis based on the interquartile range (IQR) of the probe being in the upper 80th percentile. The optimum rank of the data was calculated as eight; therefore, eight metagenes are present in the data. Three of these metagenes were either highly expressed in all samples, or expressed in no samples, indicating that they are likely metagenes for housekeeping or continually expressed genes. The remaining five metagenes corresponded to the empty vector PR-null samples (with no distinction between the −R5020 and +R5020 treatment), and the pairwise combination of WT or KR PR, with or without R5020. Thus, these analyses identified metagenes from biologically relevant subtypes of cells.

The Loi et al. human breast tumor dataset (Loi et al., 2007) contains gene expression data for both tamoxifen treated and untreated samples across several datasets. These data were aggregated together and are available through the gene expression omnibus (GEO) (accession number GSE6532). The dataset (Loi et al., 2007) was loaded into Red-R (Covington and Parikh, 2011) for processing. The basis matrix for the metagene analysis was reshaped to aggregate across the gene symbols and average the metagene values across each probe of the gene (average value). The same manipulation was performed on the expression data. Non-matching genes (those that were present in the metagene data but not in the clinical expression data or vice versa) were removed from analysis. The reshaped data were supplied to the nonnegative matrix factorization (NMF) package function (fcnnls) for scoring (as was done to generate the initial metagene fit on the T47D cell line data). As the Loi et al. data are supplied as z-scores, the data were un-logged and used in the fcnnls algorithm (as they contain negative numbers in their normal form). Samples were taken to express a metagene if they showed a non-zero value in the fitted coefficient matrix (scoring matrix).

Identification of Novel PR-Target Genes and Comparison Analysis of Gene Expression Platforms Ligand-dependent and -independent PR-target gene lists from two previously published studies (Jacobsen et al., 2005; Richer et al., 2002) were combined (duplicates were removed). Genes identified herein were upregulated (>1.5 fold BH adjusted P<0.01) as measured using either platform (Illumina and Affymetrix were combined) and duplicates were removed before Venn diagram comparison to previously known upregulated genes using the bioinformatics tool, VENNY (Oliveros, 2007).

Gene set enrichment analysis (GSEA) software (Mootha et al., 2003; Subramanian et al., 2005) was employed to compare genes up- or downregulated in cells stably expressing WT or KR PR to cells expressing inducible iWT or iKR PR. Using the Affymetrix expression data, four gene sets were created: genes up- or downregulated >2.0 fold by iWT with R5020, and genes up- or downregulated >2.0 fold by iKR with R5020. Similarly, two GSEA-formatted datasets were created from the Illumina expression data: the first dataset compares the two phenotypes (WT +R5020 vs WT −R5020), and the second compares the two phenotypes (KR +R5020 vs KR −R5020). GSEA was performed using those Illumina datasets and queried for enrichment of the Affymetrix gene sets. GSEA was executed using the default settings, except the permutation type was set to Gene_set with 1000 permutations, and the metric for ranking genes was set to Diff_of_Classes because our dataset contained log-scale data.

Chromatin Immunoprecipitation (ChIP)

ChIP assays were performed according to the ChIP-IT Express instruction manual (Active Motif, catalog #53008). Cells were plated at $15 \times 10^6$ cells per 15 cm culture dish in cMEM for 2 d, then serum starved in modified IMEM for 2 d. Cells were treated with R5020 ($10^{-8}$ M) or vehicle for 1 or 4 h. For T47D cells expressing inducible PR, AP21967 ($10^{-9}$M) was added during the starvation step. Chromatin was sheared using a Bioruptor sonicator (Diagenode, model UCB-200), for 30 min (30 s on/off). Immunoprecipitations were prepared with 60 ul of sheared chromatin, 2 ug antibody and immunoprecipitated overnight. Using the purified ChIP and input DNA, relative recruitment was determined by qPCR in triplicate. Assays were performed on a Roche LightCycler II using SYBR green master-mix. Target locus quantification was normalized as a percentage of the input DNA quantification.

To assay H3K4me2 levels, nucleosomes were isolated using micrococcal nuclease (MNase). In 15 cm dishes, $12 \times 10^6$ cells were plated in cMEM, serum starved in modified IMEM and induced with AP21967 ($10^{-9}$ M) treatment for 2 d. One day later, cells were treated with R5020 ($10^{-8}$ M) for 4 h and chromatin was harvested and immunoprecipitated as previously described (Verzi et al.).

Cell Proliferation and Apoptosis Assays

Cell proliferation was measured using MTT assays (3-[4,5-dimethylthiazol-2-yl]-2,5-diphenyltetrazolium bromide, Sigma catalog #M2128). In 24-well plates, $1 \times 10^4$ cells/well were plated in cMEM (inducible PR expression was induced with AP21967 ($10^{-9}$ M) for 2 days), cells were washed and steroid starved in modified IMEM supplemented with 5% dextran-coated charcoal-treated (DCC) FBS for 1 day before the addition of R5020 ($10^{-8}$ M). At days 0, 2, 4, 6, cell proliferation was determined by adding 60 ul MTT (5 mg/ml) to each 0.5 ml cell culture well for 3 hours, medium was carefully removed and soublization solution (90% v/v DMSO/PBS) was added to lyse the cells. Lysate absorbance (650 and 570 nm) was measured using a plate reader. 650 nm measurements were subtracted from 570 nm measurements and sample means were normalized to day zero.

Poly (ADP)-ribose polymerase 1 (PARP) cleavage assays were used to measure the level of apoptosis in cell cultures after treatment with cytotoxic concentrations of doxorubicin. T47D cells expressing inducible PR were plated in 10 cm dishes ($2 \times 10^6$ cells/dish) in cMEM and induced with AP21967 ($10^{-9}$ M). Cells were washed, induced, and serum starved for 4 d. Cells were then treated with R5020 ($10^{-8}$ M) for 6 h before adding doxorubicin (8 uM) to dishes for 24 h. Protein was harvested using standard RIPA lysis buffer, subjected to SDS-PAGE and western blotting using cleaved-PARP and PR antibodies. Beta-actin western blotting was performed for sample loading controls.

Cell viability after treatment with cytotoxic doxorubicin was determined by measuring the concentration of adenosine triphosphate (ATP), which is directly proportional to viable cell number (Crouch et al., 1993), using Cell-Titer-Glo bioluminescence assays (Promega, catalog #G7571). T47D cells expressing WT or KR PR were plated in 24-well dishes ($1 \times 10^4$ cells/well) containing cMEM. Cells were washed and steroid starved in modified IMEM supplemented with 5% DCC FBS for 1d. Cells were treated with R5020 ($10^{-8}$ M) for 6 h before doxorubicin (6 uM) was added to the wells. After 4 d, cell viability was determined by adding Cell-Titer-Glo substrate and luminescence was measured using a plate reader. Sample means were normalized to day zero (n=6, −/+SD).

Oncomine Data Analysis

The relative expression of individual PR target genes in human breast tumor samples was determined by searching the Oncomine database (version 4.4, October 2011 data release). Individual PR target genes (e.g. RGS2) were queried in The Cancer Genome Atlas (TCGA) Breast 2 dataset. Oncomine output data was sorted to isolate "cancer versus normal" associations, and reported (FIG. 2A) as the copy number unit expression values for blood, normal breast and breast carcinoma samples using box-and-whiskers plots (dots: max/min, whiskers: 90/10 percentiles, box: 75/25 percentiles, line: median of all samples). For each analysis, specific breast carcinomas specified for each gene are: Invasive Lobular Breast Carcinoma (MSX2), Invasive Ductal and Lobular Carcinoma (RGS2), Intraductal Cribriform Breast Adenocarcinoma (MAP1A), and Mucinous Breast Carcinoma (PDK4).

Multiple breast cancer "concepts", as described in the Oncomine database, were associated with the ligand dependent (LD) KR>WT gene signature. According to Oncomine, concepts are derived from gene expression microarrays or gene-copy-number datasets derived from tumor cohorts or cancer cell line experiments. Specifically, concepts are a list of genes from various published datasets that are defined by some criteria (e.g. top 5% of genes expressed in ERBB2-positive breast tumors). The ligand dependent (LD) gene signature was created by normalizing the gene expression values in the R5020 treatment group to the non R5020 treatment group, then comparing those normalized fold change values between the KR and WT PR expressing cell lines. This analysis identified 151 LD genes upregulated >1.5 fold in cells expressing SUMO-deficient PR versus WT PR expressing cells. The ligand-independent (LI) gene signature was created by normalizing the gene expression values in the non R5020 treatment group in WT or KR expressing cells to the non R5020 treatment group in the PR-null expressing cells, then comparing those normalized fold change values between the KR and WT expressing cell lines. This analysis identified 92 LI genes upregulated >1.5 fold in cells expressing SUMO-deficient PR versus WT PR expressing cells. These PR gene signatures were uploaded into Oncomine Research Premium Edition software (Compendia Bioscience, Ann Arbor, Mich.) and the database was searched for associated concepts.

Results

Figure 1A:
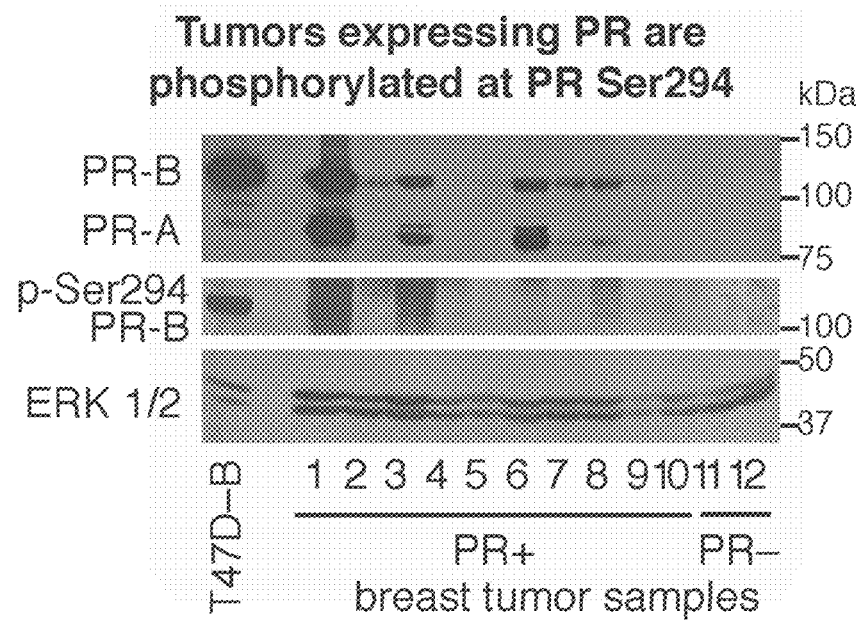

PR SUMOylation alters promoter selection in T47D breast cancer cells. For unknown reasons, there is little overlap between PR-regulated genes in normal relative to neoplastic breast tissues (Graham et al., 2009). One mechanism for the apparent divergence of PR functions may relate to early events in breast cancer development, such as altered signal transduction. Based in part on our prior studies (Daniel et al., 2007a; Daniel and Lange, 2009; Daniel et al., 2007b), it is predicted that the balance between SUMOylated and phosphorylated (i.e. deSUMOylated) PRs is frequently altered in breast cancer, resulting in changes in PR promoter selectivity and altered patterns of gene expression. In a screen of 10 breast tumors clinically defined as PR positive, a wide range of total PR mRNA (not shown) and protein expression (FIG. 1A) was detected. Of the 7 (out of 10) breast tumors that were confirmed to be PR positive by both RT-qPCR and western blotting, at least 5 samples (lanes 1, 3, 6, 8, and 9) also clearly contained some level of phospho-Ser294 PR-B (FIG. 1A). Remarkably, 2 of 10 tumors (lanes 1 and 3) contained abundant phospho-Ser294 PR-B. Notably, PR-B, but not PR-A, Ser294 is rapidly phosphorylated in response to either progestins or peptide growth factors that input to proline-directed protein kinases, primarily within the MAPK and CDK families (Clemm et al., 2000). Consistent with this finding, EGF blocked progestin-induced PR-B, but not PR-A SUMOylation (Daniel et al., 2007a).

Figure 1B:
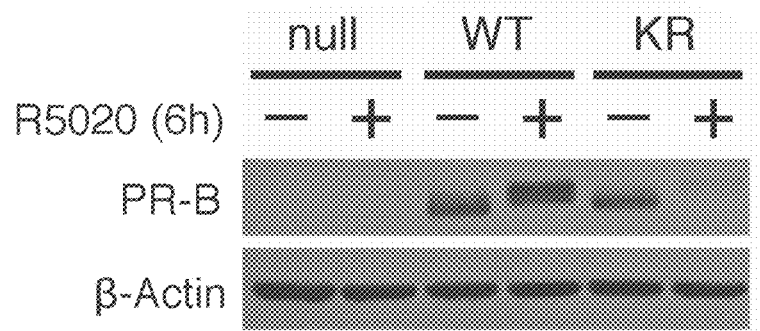
Figure 1C:
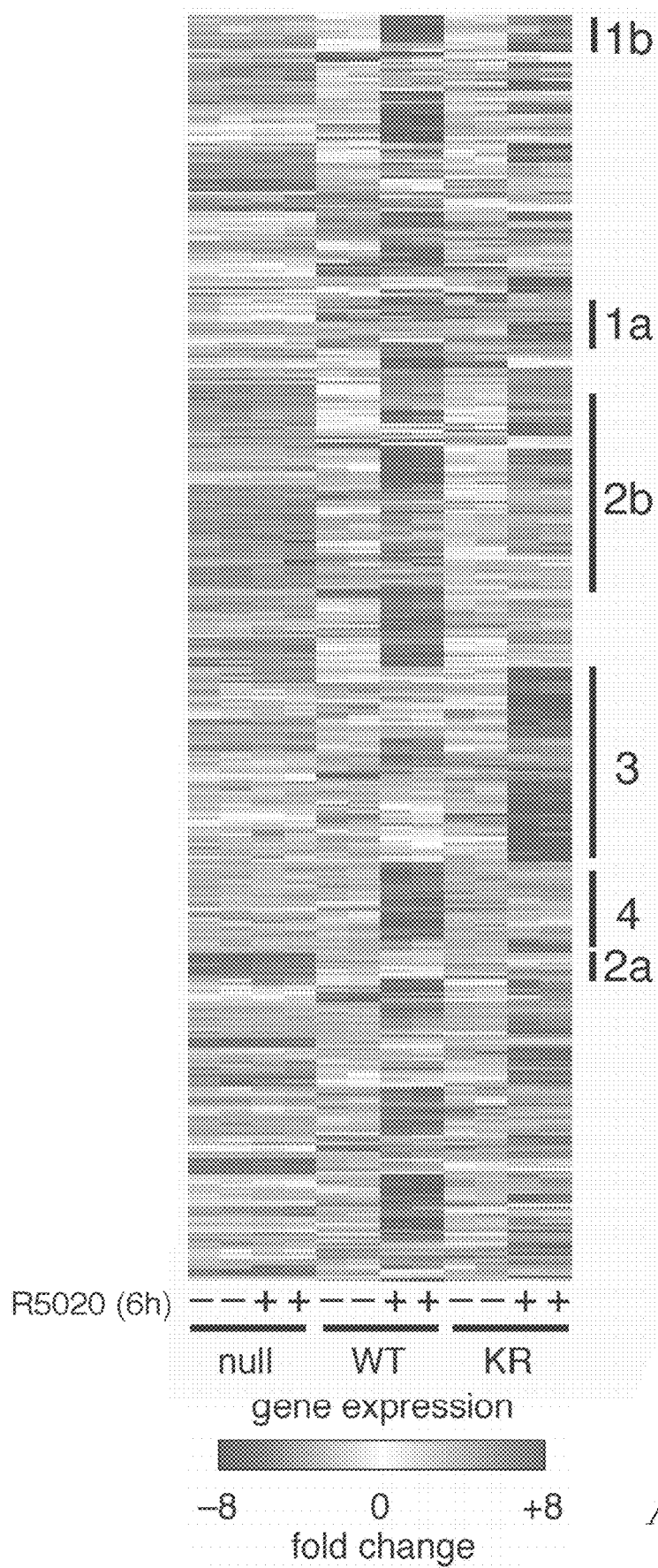

It is disclosed herein that PR target genes differ according to PR SUMOylation status. The broad range of PR expression in clinical specimens (FIG. 1A and (Liu et al., 2010)) suggests that PR-dependent gene expression may provide a more accurate marker of PR contribution to breast cancer phenotypes. To address the unique actions of phosphorylated and SUMO-deficient PR-B, the transcriptional profiles of breast cancer cells stably expressing either wild-type (capable of SUMOylation) or SUMO-deficient (K388R mutant/phospho mimic) PR-B molecules was measured using whole genome expression profiling. Multiple clones were engineered of vector-matched PR-null T47D breast cancer cells expressing either wild-type (WT) PR-B or mutant K388R (KR) PR-B that is unable to undergo SUMO modification at Lys388; this SUMO-deficient receptor is a functional mimic for PR-B that is persistently phosphorylated on Ser294 (Daniel et al., 2007a; Lange et al., 2000). Phospho-Ser294 and S294D receptors are hyperactive transcription factors that undergo rapid ligand-dependent (ubiquitin-mediated) downregulation relative to WT PRs (Daniel et al., 2007b). Cells expressing either WT or KR PR-B were then treated with the synthetic progestin, R5020 ($10^{-8}$ M), for 6 h (FIG. 1B). Upon ligand-binding, PR is globally phosphorylated at multiple sites, as indicated by a slight gel upshift (Takimoto et al., 1996). Consistent with the previous reports (Daniel et al., 2007a; Daniel and Lange, 2009) hyperactivated KR PR undergoes slightly more rapid ligand-induced (ubiquitin proteasome-dependent) downregulation (apparent at 6 h) relative to WT PR (Lange et al., 2000). Using these experimental conditions, global gene expression profiles were simultaneously measured using Illumina HT-12v4 whole genome gene expression bead arrays (FIG. 1C). Top regulated genes were organized by heat maps showing up- or downregulated genes (fold change >8.0 in at least one sample, BH adjusted P<0.001, FIG. 1C). Upon progestin treatment, these cells displayed diverse expression patterns; multiple PR-regulated gene sets became readily apparent (FIG. 1C; compare groups of PR-regulated genes upregulated (1a) or downregulated (1b) by ligand-dependent PRs relative to untreated controls, genes upregulated (2a) or downregulated (2b) by ligand-independent PRs relative to PR-null controls, and ligand-dependent genes upregulated primarily in KR relative to WT (3) or WT relative to KR (4) expressing cell lines).

Figure 1E:
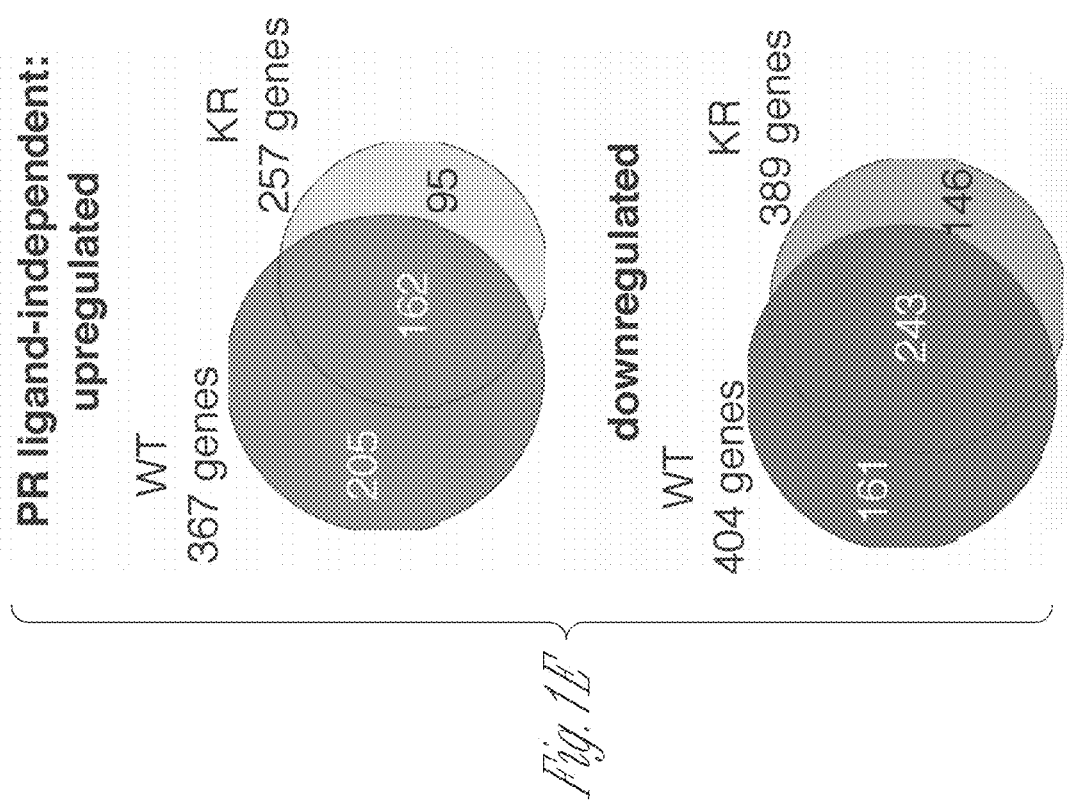
Figure 1D:
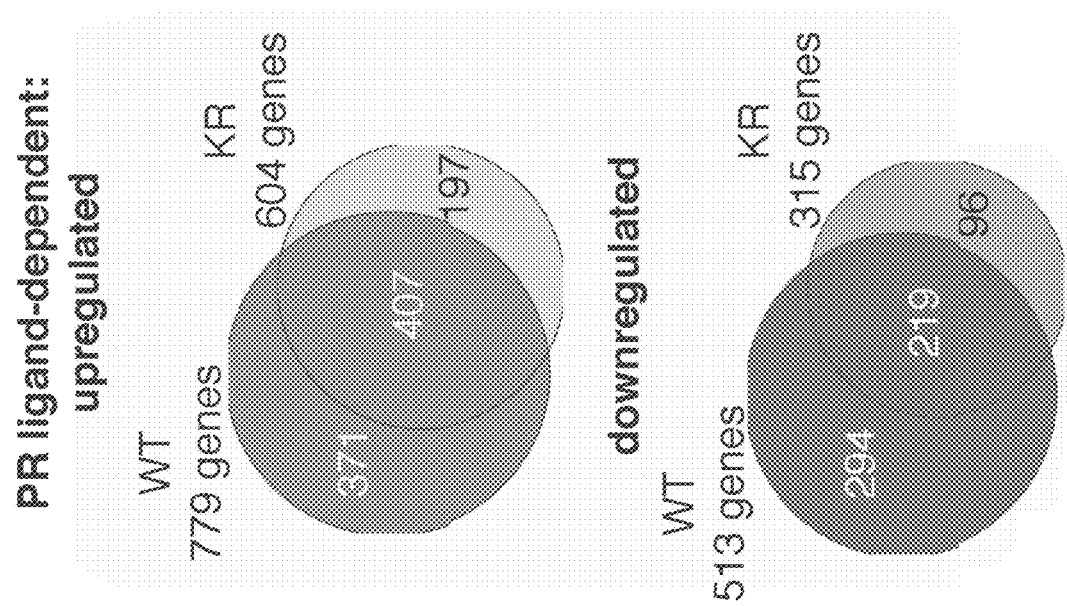

Genes were identified that were upregulated >1.5 fold by PR in a ligand-dependent or -independent manner and discovered gene expression overlap between cells expressing either KR or WT receptors, as well as subsets of uniquely regulated genes (FIG. 1D-E). The expression profiles were next validated for numerous PR target genes from these classes using RT-qPCR (FIG. 1F). Notably, RGS2 expression (primarily upregulated by the KR receptor) is over-expressed in the basal/myoepithelial compartment and substantially elevated in a majority of breast tumors (Smalley et al., 2007). In contrast, BCL2L11 (BIM) is a pro-apoptotic mediator involved in ERBB/MAPK-dependent luminal cell clearing (Reginato et al., 2005) whose expression is primarily upregulated by WT but not KR receptors. As these examples suggest, the gene array robustly identified diverse classes of PR target genes, and contains gene expression profiles indicative of mechanisms of PR-mediated cellular proliferation and survival.

These results essentially repeated in T47D cells engineered to express either WT or KR PR from an inducible vector system (FIG. 1.1). In this model, inducible expression of PRs (iWT or iKR) is solely dependent on the presence of a small molecule dimerizer, AP21967, added to the cell culture medium; equal levels of either iWT or iKR were induced upon treatment with AP21967 and these receptors were equally phosphorylated on Ser294 in response to progestin (FIG. 1.1A). Cells were treated with AP21967 ($10^{-9}$ M) and R5020 ($10^{-8}$ M) and assayed for changes in gene expression using the Affymetrix U133A 2.0 microarray platform. PR-dependent gene expression profiles obtained from T47D cells stably expressing PR (assayed using the Illumina platform) were significantly similar to gene array data obtained from the same parental cells (T47D) inducibly expressing PR (assayed via the Affymetrix platform; see FIG. 1.1B-C). Together, the arrays identified a greater number of PR regulated genes (>1.5 fold, BH adjusted P<0.01) than previous reports (Jacobsen et al., 2005; Richer et al., 2002); microarray platforms now contain thousands more "reporters" relative to earlier technologies. 70% of the previously known PR target genes were identified but also revealed hundreds of novel PR target genes (data not shown).

Phosphorylation of PR Ser294 drives SUMO-deficient PR gene expression. To investigate mechanisms of regulation of "SUMO-sensitive" PR-target genes, we selected four genes were selected (MSX2, RGS2, MAP1A and PDK4) from the microarray analysis for further study. These specific genes were upregulated in cells expressing KR, but not WT receptors (FIG. 1D, 197 gene category). A query of the Oncomine database demonstrated that all four genes are amplified in breast carcinomas relative to normal breast tissue and blood (FIG. 2A). To validate SUMO-dependent changes in PR target gene expression in an additional breast cancer model, we stably introduced vector control, WT or KR receptors into MCF-7 cells expressing low levels of endogenous PR (in the absence of estrogen). These cells were treated with vehicle control (ethanol) or R5020 ($10^{-8}$ M) in the absence or presence of the PR antagonist, RU486 ($10^{-7}$ M) for 6 h (FIG. 2B). Progestin-induced gene expression profiles in MCF-7 cells were nearly identical to those obtained in our T47D cell models (MSX2, RGS2, MAP1A, and PDK4). Additionally, their R5020-induced mRNA expression was completely abolished by addition of RU486, indicating that regulation of these genes is entirely PR-dependent.

It was shown previously that SUMO-deficient KR receptors closely mimic phospho-Ser294 (WT) PR species (Daniel et al., 2007a). To demonstrate the phosphorylation-dependence of PR regulation on the same set of genes (MSX2, RGS2, MAP1A, and PDK4), PR-null T47D cells or T47D cells stably expressing WT, KR, or phospho-mutant S294A (SA) PR-B (Lange et al., 2000) were employed. Mutation of PR Ser294 results in a heavily SUMOylated receptor that is transcriptionally repressive, as measured by luciferase reporter assays (Daniel et al., 2007a). Consistent with this finding, progestin-induced upregulation of endogenous PR target genes was blocked in cells expressing S294A PR relative to cells expressing SUMO-deficient KR PR (FIG. 2C). Progestin-induced gene expression was rescued (i.e. comparable to that induced in R5020-treated KR cells) in cells expressing the PR double mutant (KRSA), containing point mutations at both Ser294 and Lys388, suggesting that PR deSUMOylation is the dominant event required for ligand-dependent upregulation (derepression) of these phosphorylation-dependent PR target genes.

Figure 2D:
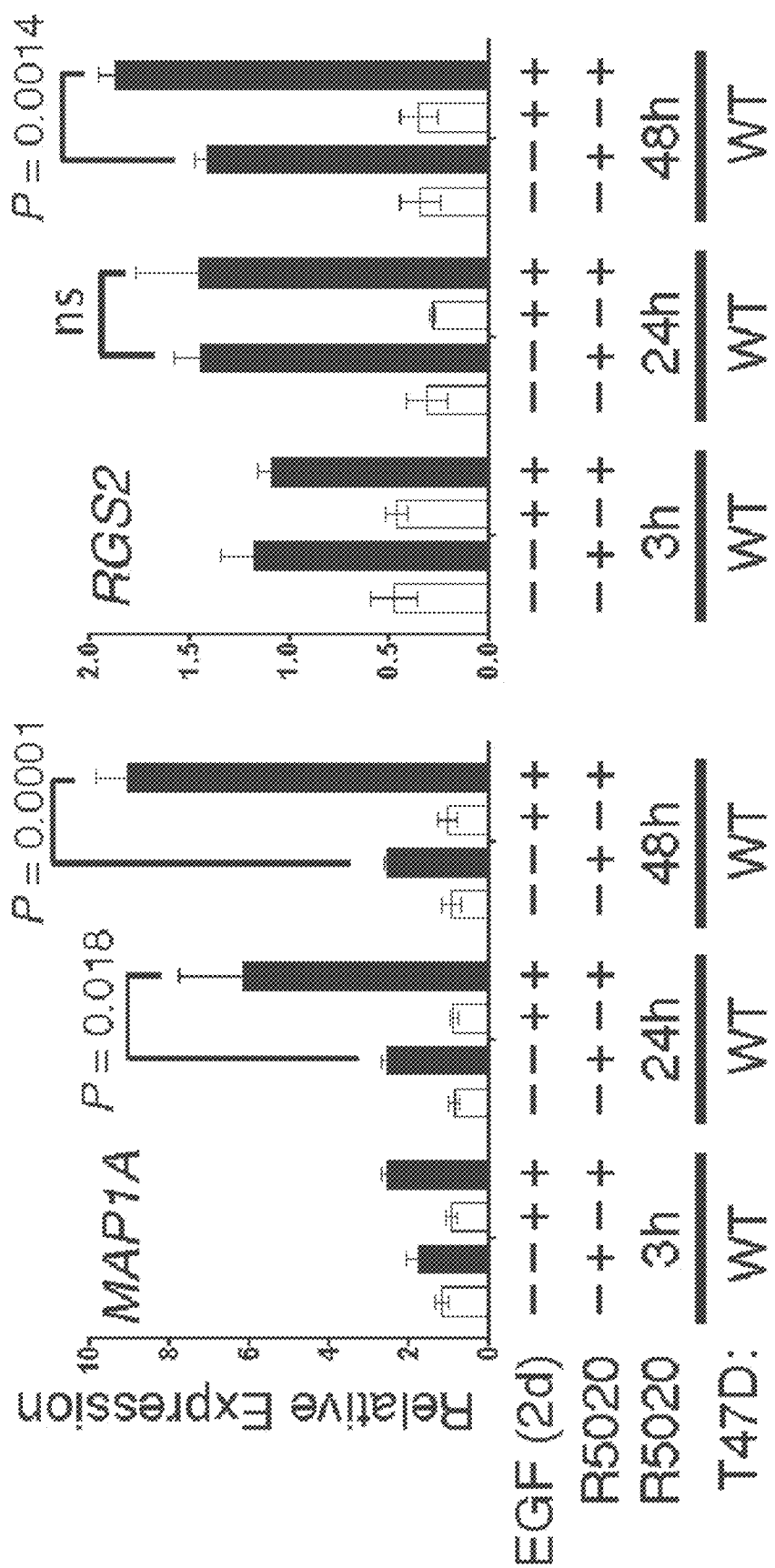
Figure 2E:
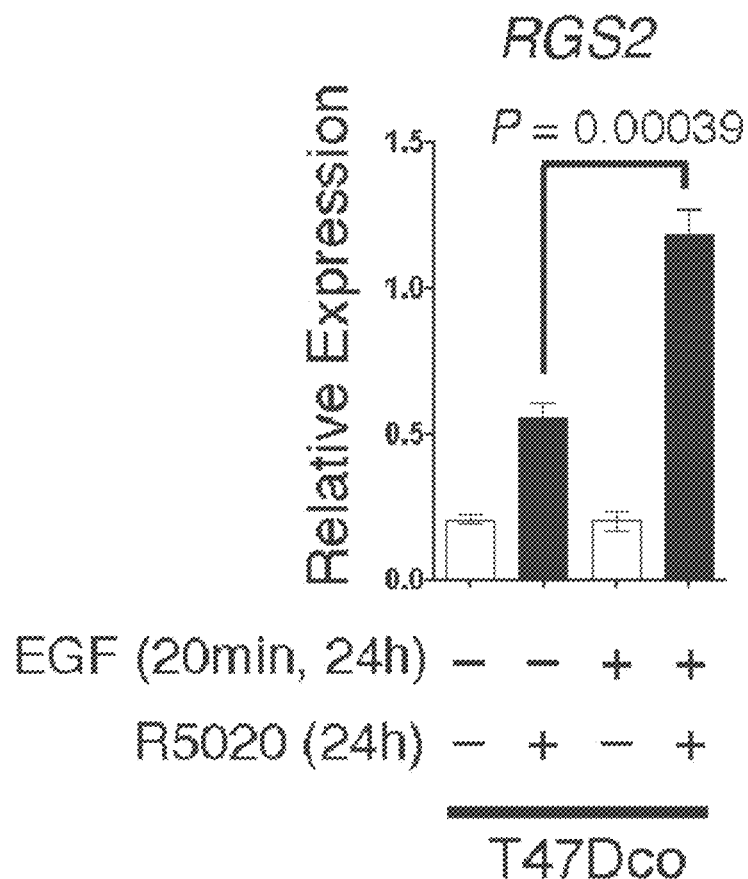

Treatment of breast cancer cells with EGF induces robust PR Ser294 phosphorylation and deSUMOylation (Daniel et al., 2007a). T47D cells stably expressing WT PR were therefore pre-treated with EGF (100 ng/ml) followed by vehicle control or R5020 ($10^{-8}$ M). Both MAP1A and RGS2 were insensitive to EGF alone over a 2-day time course (FIG. 2D). However, EGF pre-treatment significantly augmented progestin stimulated mRNA expression of both genes (FIG. 2D). Similar results were observed for RGS2, but not MAP1A expression in parental (expressing both endogenous PR-A and PR-B isoforms) T47Dco cells treated for 6 hours (FIG. 2E). Multiple factors (i.e. strength and duration of PR phosphorylation, transcriptional activity, and protein levels) likely influence the kinetics of PR-regulated MAP1A expression in cells stimulated broadly with growth factors. In T47D cells stably expressing WT PR-B, MAP1A mRNA expression was synergistically upregulated following just 3 h of treatment with progestin plus heregulin-eta1; progestin-alone treatment approached this level by 24 h (data not shown). Taken together, the data suggest that PR dynamically regulates multiple endogenous genes according to its phosphorylation and SUMOylation status; growth factors favor phospho-PR that act as derepressed transcription factors.

Figure 3A:
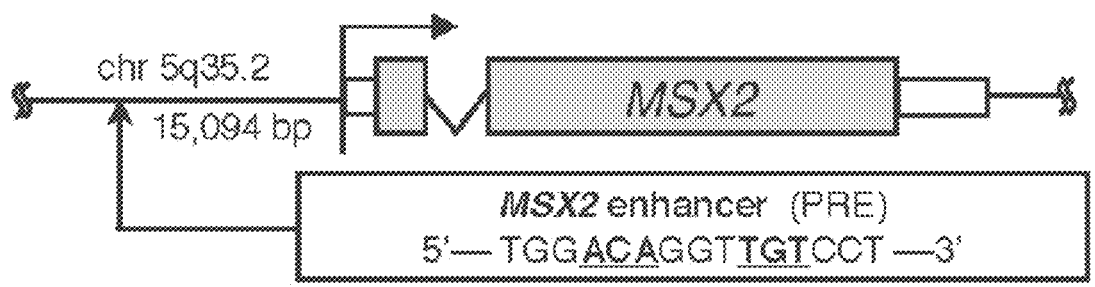

PR SUMO modification provides a mechanism for promoter selection. The gene array analyses indicated that SUMO modification of PR alters the magnitude of transcriptional response on selected promoters, while the regulation of other PR target genes is completely insensitive to PR SUMOylation (FIG. 1). To investigate mechanisms of PR promoter selection, the recruitment of PR and selected coregulators to the chromatin of differentially regulated PR target genes was examined. Initially the experimental focus was on MSX2. Similar to PR-B, this homeobox transcription factor is essential for mammary gland development and transgenic expression of MSX2 causes ductal hyperplasia in mice (Satoh et al., 2007; Satokata et al., 2000). Functional studies indicate that MSX2 induces cyclin D1 and E1 expression (Satoh et al., 2004), is involved in RAS-mediated cellular transformation (Takahashi et al., 1997) and drives epithelial-to-mesenchymal transition through downregulation of epithelial markers (di Bari et al., 2009). Lanigan et al. (Lanigan et al., 2010) showed that MSX2 expression is significantly elevated in both luminal B and HER2-enriched molecular subtypes of breast cancer, despite being associated with good prognosis (i.e. similar to ER and PR). Multiple consensus progesterone response element (PRE) sequences up- and downstream of the MSX2 transcriptional start site were identified using MatInspector software (Cartharius et al., 2005). In particular, one PRE aligned with a region of known PR recruitment, based on the PR cistrome (i.e. derived from unpublished ChIP-chip experiments provided by Myles Brown, Harvard University, Boston, Mass.). MSX2 is transcriptionally upregulated in response to progestin treatment of T47D or MCF-7 cells stably or inducibly (T47D) expressing SUMO-deficient PR, but not WT receptors (FIG. 2B-C, 1.1C). To investigate direct recruitment of PR to the PRE enhancer region of MSX2 (FIG. 3A), cells constitutively (or inducibly) expressing either WT or KR PR were treated with R5020 ($10^{-8}$ M), and performed chromatin immunoprecipitation (ChIP) assays. Following progestin treatment, both WT and KR PR were readily detected at the PRE enhancer region (FIG. 3B left), although no transcriptional activity (mRNA levels as measured by RT-qPCR) in progestin-treated cells expressing WT PR (FIG. 2B-C, 1.1C) was detected. Notably, significantly more SUMO-deficient KR PR was recruited to the MSX2 enhancer locus relative to that of WT PR. This finding repeated in cells expressing inducible PR (FIG. 3B right) as well as at PRE-containing enhancers of multiple other genes upregulated by SUMO-deficient PR (FIG. 3.1). The recruitment of a common PR transcriptional coactivator, cAMP-response element-binding protein (CREB)-binding protein (CBP) to the MSX2 enhancer locus was then investigated. CBP interacts with multiple nuclear receptors, functions as a transcriptional scaffold, and has histone acetyltransferase (HAT) activity (Lambert and Nordeen, 2003; Li et al., 2003; Ogryzko et al., 1996). Using ChIP assays, it was determined that upon progestin treatment, CBP recruitment to the MSX2 locus is significantly elevated in cells expressing SUMO-deficient KR PR, but not WT PR (FIG. 3C). Consistent with the increased presence of this coactivator associated with KR PR, increased recruitment of total and functionally active phospho-Ser5 RNA polymerase II to the MSX2 proximal promoter region in progestin-treated cells expressing iKR PR relative to cells expressing iWT PR was observed (FIG. 3.2). These data may explain why although WT PR is clearly recruited to this region in the presence of progestin (FIG. 3B), significant mRNA expression does not occur (FIG. 2B-C, 1.1C). The constitutive association of deSUMOylated PRs and SRC1 at endogenous gene loci was previously reported (Daniel and Lange, 2009).

Figure 3B:
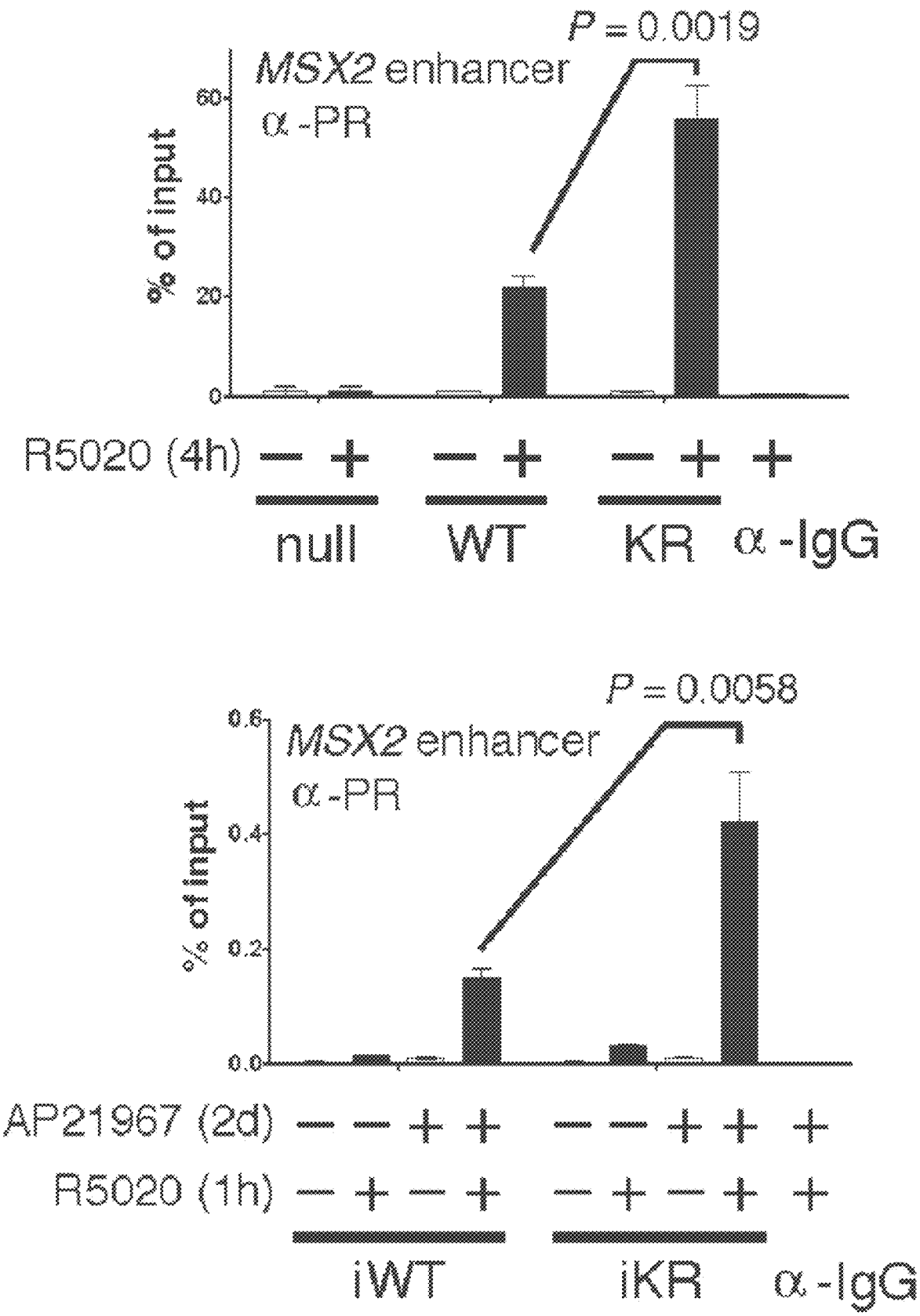
Figure 3D:
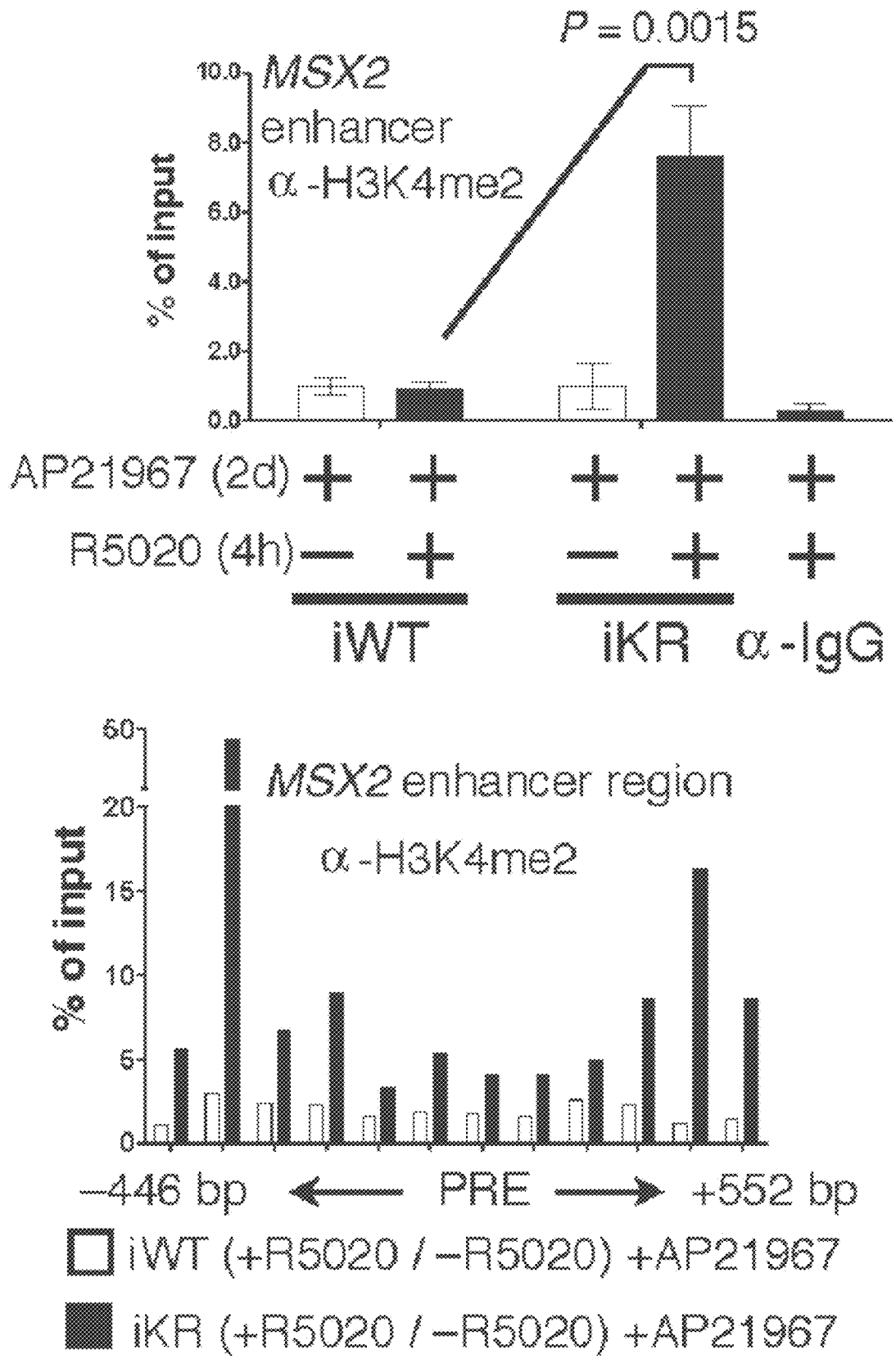

Histone tail modifications (methylation, acetylation, phosphorylation, etc.) are epigenetic modifications known to significantly impact chromatin dynamics and thereby affect changes in gene expression (reviewed in (Ong and Corces, 2011)). Generally, histone H3 Lys4 dimethylation (H3K4me2) is an epigenetic mark associated with transcriptional activation (Barski et al., 2007; He et al., 2010). H3K4me2 marks areas of transcription factor-facilitated paired nucleosome positioning, and is an indicator of nearby gene activation (He et al., 2010). To measure the level of H3K4me2 at the MSX2 enhancer locus, T47D cells expressing inducible PRs (iWT and iKR) were treated with R5020 ($10^{-8}$ M) for 4 h and nucleosomes were isolated after micrococcal nuclease (MNase) digestion; histone methylation was determined by ChIP, followed by qPCR (FIG. 3D left). H3K4me2 levels were elevated in progestin-treated cells expressing iKR relative to cells expressing iWT PR. The R5020-induced fold change in H3K4me2 surrounding the MSX2 PRE locus (approximately 500 base pairs up- and downstream using overlapping qPCR products) was also measured to visualize local histone dimethylation patterns (FIG. 3D right). Progestin-dependent H3K4me2 was enriched in cells expressing SUMO-deficient iKR PR compared to cells expressing iWT. Indeed, the higher levels of histone methylation flanking the PRE sequence is likely a consequence of nucleosome remodeling and spreading that facilitates recruitment of transcription factor complexes at this functional enhancer region (He et al., 2010).

Figure 3E:
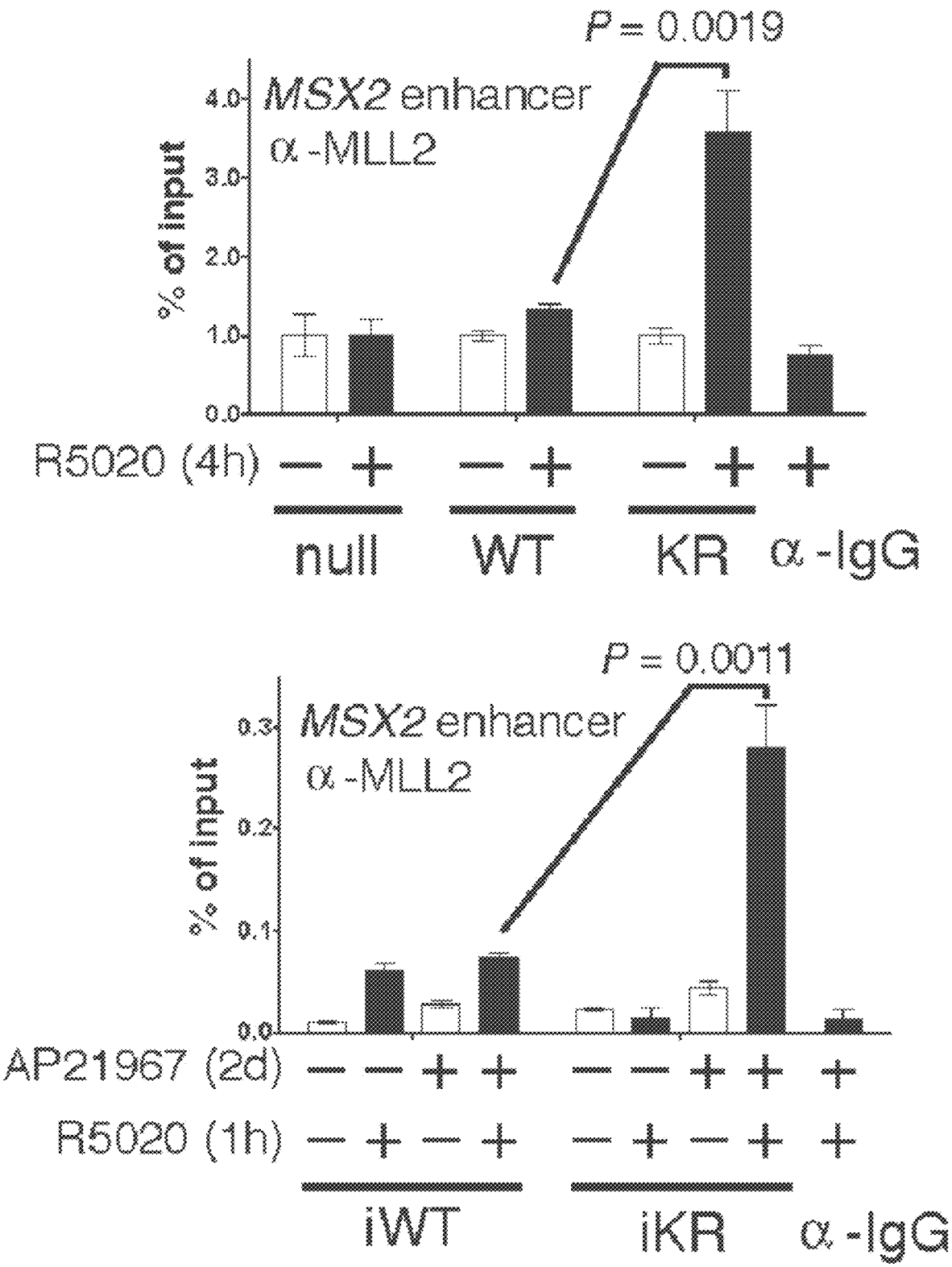
Figure 33:
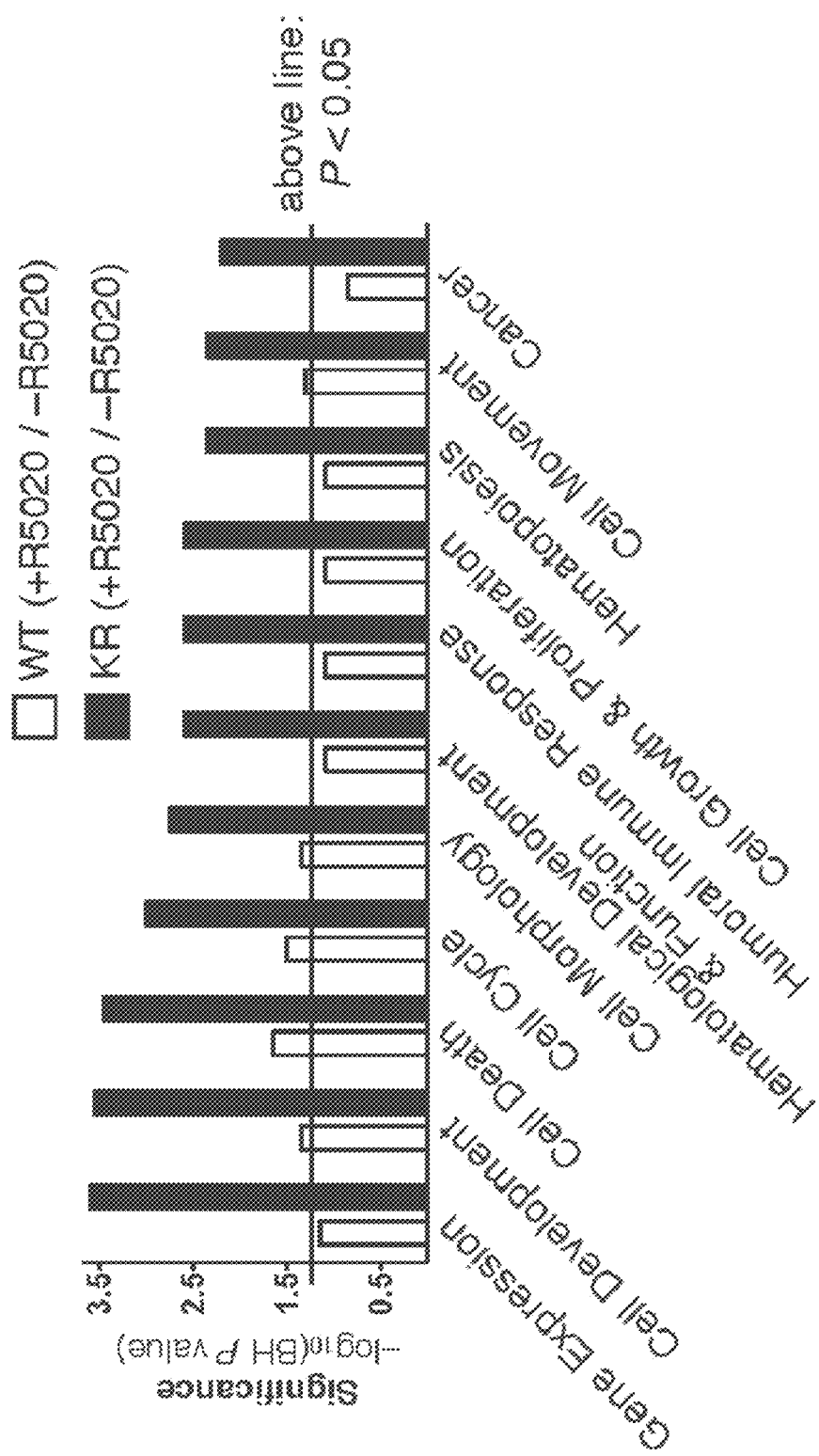

These results suggest that one or more histone methyltransferases are differentially recruited to the MSX2 enhancer in cells expressing either iWT or iKR PR. Recently, a chromatin remodeling complex, including the subunit mixed lineage leukemia 2 (MLL2) methyltransferase, was implicated in progestin-dependent H3K4 trimethylation (Vicent et al., 2011). Additionally, ER-alpha interacts directly with MLL2 though its LXXLL motifs and MLL2 mediates estrogen-dependent transcriptional upregulation in MCF-7 cells (Mo et al., 2006). Herein, using both stable and inducible T47D models, it was discovered that MLL2 is significantly recruited to the MSX2 enhancer in progestin treated cells expressing SUMO-deficient KR PR, but not WT PR (FIG. 3E).

Finally, the relative recruitment of PR to a PRE-containing enhancer locus near MAT2A, a control PR-target gene that is insensitive to PR SUMOylation status was measured (FIG. 1D, overlapping Venn category). MAT2A mRNA expression was equally upregulated in progestin-treated cells expressing either WT or KR PR (FIG. 3F left). Likewise, progestin-dependent recruitment of PR and MLL2 to the same PRE-containing region in the MAT2A enhancer was very similar in cells expressing either WT or KR PR (FIG. 3F center and right). Taken together, these data suggest that enhancer/promoter structure (in chromatin) functions in combination with PR SUMOylation to block important interactions between PR and mediators of early chromatin remodeling (MLL2) as well as major coregulators, including CBP; higher levels of these factors were specifically associated with "sensitive" PRE regions in cells expressing SUMO-deficient PR. Perhaps SUMO-sensitive enhancer regions require PR-dependent recruitment of MLL2 in order to initiate changes in nucleosome positioning at relatively "closed" regions (i.e. with regard to genes like MSX2). In contrast, pre-existing "open" regions may be insensitive to PR SUMO modification (i.e. with regard to genes like MAT2A). Additionally, preferential association of SUMO-deficient PR with other factors (i.e. pioneer-type transcription factors) may contribute to PR promoter selection; KR recruitment to the MSX2 enhancer region is significantly enhanced relative to WT receptor in the presence of progestin (FIG. 3B). These questions await further detailed global gene and cistrome analyses (see Discussion).

Figure 4A:
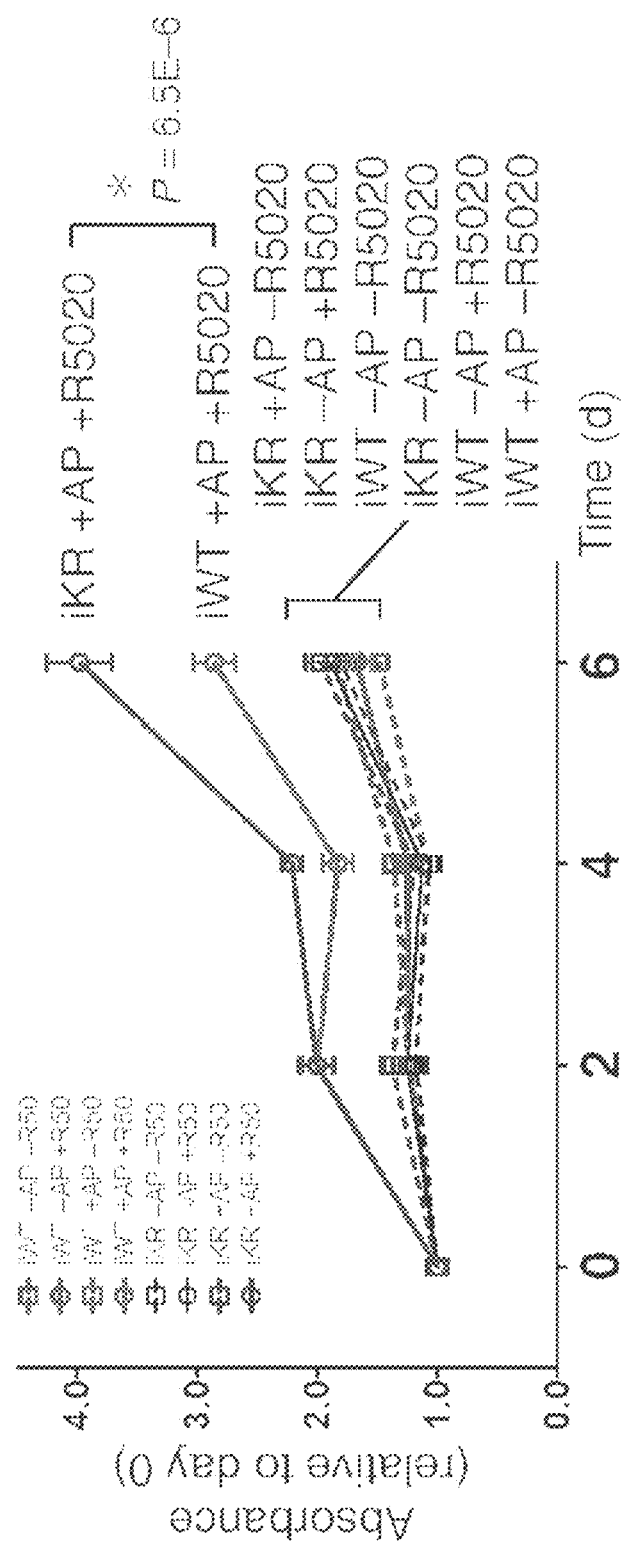
FIGS. 4A-D. SUMO-deficient progesterone receptors promote increased cell proliferation and decreased apoptosis. (A) The proliferative potential of T47D cell lines expressing inducible PR was measured using MTT assays in the presence of progestin (R5020) and inducer, AP21967 (AP) (B) Western blot showing that inducible PR expression is sustained for at least five days following the addition of AP21967 to the cell culture media, ERK1/2 western blotting was performed as a loading control. (C) Apoptosis occurring in cells expressing inducible PRs was detected by western blotting for poly (ADP)-ribose polymerase 1 (PARP) cleavage. Cells were treated with progestin and/or doxorubicin before protein harvest. (D) Proliferation and apoptosis was measured in cells constitutively expressing PR using cell viability luciferase assays, where day 4 luminescence was normalized to day 0. Pooled data are represented as mean of n=6+/−SD and significance calculated using Student's t-test.
Figure 4B:
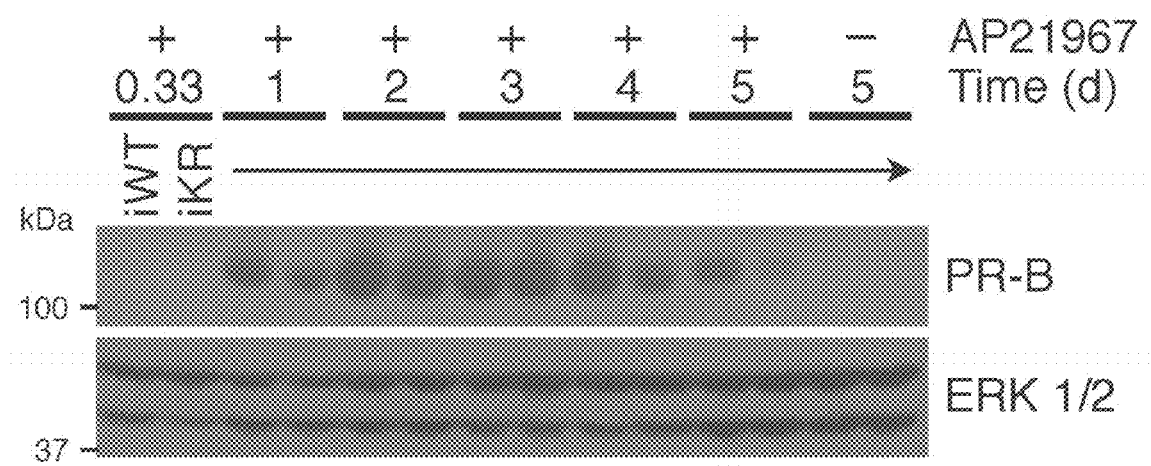

SUMO-deficient phospho-PR promotes increased cell proliferation and decreased apoptosis. Ingenuity Pathway Analysis (IPA, Ingenuity Systems) software contains a large database of genes that are manually assigned to molecularly defined pathways, biological functions or disease states, and based on current literature. Using this tool, ligand-dependent upregulated genes (>2 fold, BH adjusted P<0.01) in cells stably expressing either WT or KR receptors were compared. Upon progestin treatment, SUMO-deficient PR, but not WT, significantly upregulated gene sets assigned to multiple proliferative and pro-survival biological functions (FIG. 3.3). Breast cancer cells stably expressing SUMO-deficient PR exhibit increased growth in soft-agar relative to cells stably expressing either WT or phosphorylation-deficient S294A PR (Daniel et al., 2007a; Daniel and Lange, 2009). Herein, MTT proliferation assays were performed using the inducible models (FIG. 4A). The advantage of this isogenic system is the elimination of clonal variation in cell growth/death rates and phenotypic drift that can occur in stable cell line models. Cells were plated at equal density on day zero and treated with or without the AP21967 compound to induce PR expression, prior to exposure to either vehicle (ethanol) or R5020. R5020-treated cells expressing iWT or iKR PRs grew faster than their un-induced or untreated counterparts. However, by day six of continuous exposure to both AP21967 and R5020, significantly more cells were present in cultures expressing iKR relative to those expressing iWT receptors, while all control groups remained very similar. Western blotting demonstrated that inducible PR expression was sustained when AP21967 was added to the cell culture media and that comparable levels of iWT and iKR PR protein were expressed (FIG. 4B).

Figure 4C:
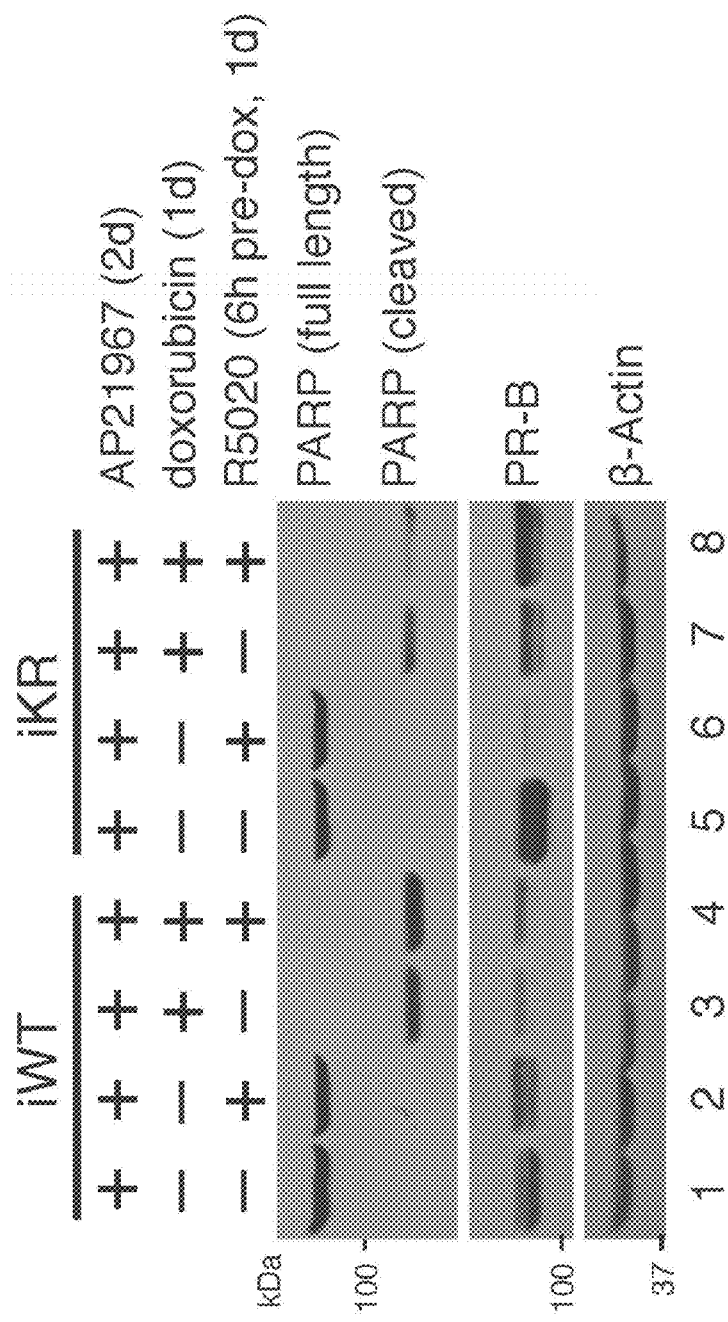
Figure 4D:
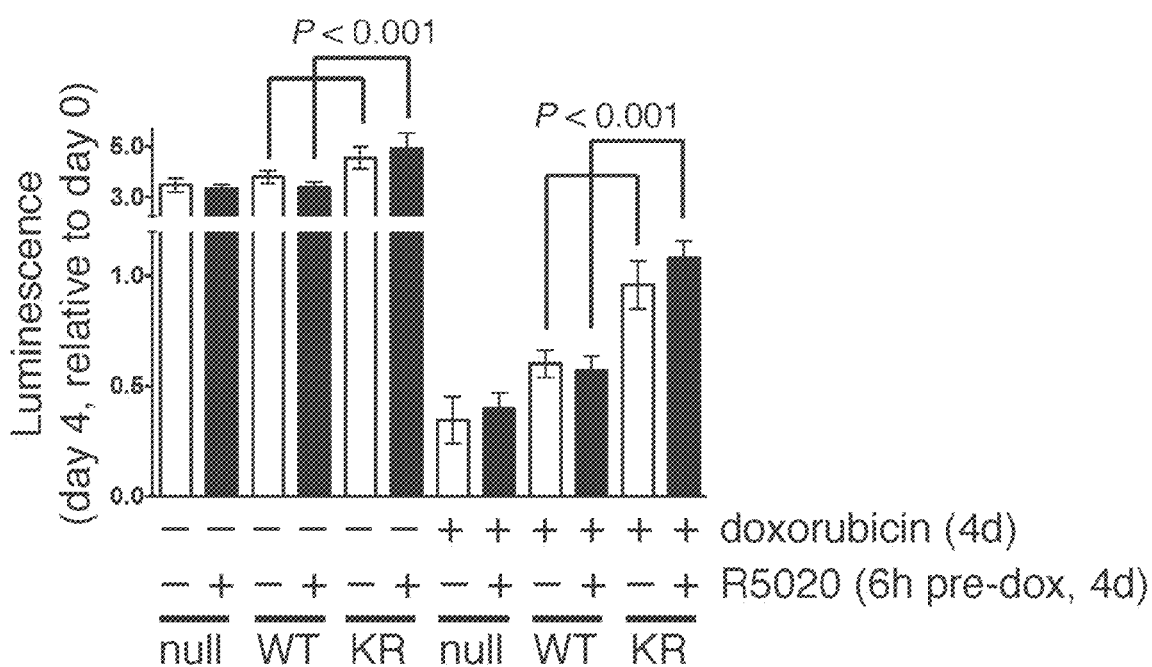

MTT assays measure viable (surviving) cells over time and PRs have been implicated in breast cancer cell pro-survival (Lange, 2008; Moore et al., 2000). Thus, cleavage of poly (ADP-ribose) polymerase 1 (PARP) was also measured as an indirect indicator of apoptosis. PARP is targeted for cleavage at Asp214 by activated Caspase-3 and is a sensitive measure of committed apoptotic signaling (Nicholson et al., 1995). PR expression was induced by AP21967 treatment and cells were pre-treated with R5020 for 6 h to activate the respective iWT or SUMO-deficient iKR gene expression programs. Following R5020 pre-treatment, doxorubicin was added to the cell culture medium to induce apoptosis for one day, after which the cell lysate was harvested and the relative levels of cleaved PARP were measured by western blotting (FIG. 4C). Notably, doxorubicin-treated cells expressing SUMO-deficient iKR PR had reduced levels of PARP cleavage relative to cells expressing iWT PR, especially in cells pre-treated with R5020 (compare lanes 4 and 8). Doxorubicin treatment reduced both WT and KR PR protein expression (FIG. 4C, compare lanes 1 and 3, or lanes 5 and 7). However, in multiple repeat experiments normalized to protein expression changes, cells expressing iKR PR consistently exhibited reduced PARP cleavage relative to cells expressing iWT PR. These findings were validated in T47D cells stably expressing PRs. PR-null cells and cells stably expressing either WT or KR PR were plated in complete media, serum starved and treated with R5020, with or without doxorubicin (FIG. 4D). Again, significantly increased cell viability was observed in progestin-treated cells expressing SUMO-deficient KR PR. Interestingly, when these cells were challenged with cytotoxic concentrations of doxorubicin, their viability was doubled relative to cells expressing WT PR (FIG. 4D). These data suggest that SUMO-deficient PRs are important mediators of increased cell proliferation and pro-survival signaling; cells expressing modified PRs undergo biological processes consistent with their associated gene expression profiles (FIG. 1).

The SUMO-deficient PR gene signature is associated with ERBB2 positive breast cancers. Human breast cancers often contain high levels of MAPK, AKT, and/or CDK protein and/or kinase activities, thus favoring PR derepression (Daniel et al., 2007a; Daniel and Lange, 2009). To probe published human breast cancer databases for evidence of genetic patterns suggestive of phospho-PR-driven (SUMO-deficient) lesions, unique PR gene signatures were defined that were comprised of genes whose expression was greater in cells expressing KR relative to cells expressing WT receptors (expression >1.5 fold in KR vs. WT, BH adjusted P<0.01). These genes were predominantly upregulated in cells expressing KR receptors and/or down regulated only in cells expressing WT receptors. This analysis was performed for both ligand-dependent and ligand-independent PR target genes. Using these criteria, unique 151- and 92-gene signatures were created and defined as PR-target genes differentially upregulated (compared to WT) by ligand-dependent (LD) and ligand-independent (LI) KR receptors, respectively (FIG. 4.1).

These gene signatures were then uploaded into the Oncomine Research Premium Edition (Compendia Bioscience, Ann Arbor, Mich.) and the database was interrogated for associated concepts (reviewed in (Rhodes et al., 2007)). Oncomine concepts are gene lists defined by specific criteria (e.g. top over-expressed genes in a particular tumor cohort). The LD 151-gene signature was associated with multiple breast cancer concepts with high significance (P<0.0001, FDR <0.01) (data not shown). Remarkably, five distinct ERBB2-positive breast cancer concepts (two from cell lines and three from tumor cohorts) were independently associated with this LD PR-gene signature. Thus, genes specifically upregulated in the presence of progestin in cells expressing SUMO-deficient PR are among the same genes highly over-expressed (top 5-10%) in ERBB2-positive breast cancers (FIG. 5A, data not shown). Notably, the LI 92-gene signature was also significantly associated with at least one ERBB2-positive concept (Bonnefoi et al., 2007). These data indicate that both ligand-dependent and -independent unique PR-regulated gene sets are significantly upregulated in protein-kinase-driven tumors, including those known to be ERBB2-positive (FIG. 5A).

Expression of these related genetic programs (SUMO-deficient PR and ERBB2 signaling) might represent independent means utilized by breast cancer cells to drive cell proliferation and survival. Indeed, HER2-enriched breast cancers are frequently steroid hormone receptor (SR) negative (Perou et al., 2000; Sørlie et al., 2001). Alternatively, these statistically significantly associated concepts may be functionally linked. Luminal breast cancers are primarily SR-positive, but approximately 7% of luminal A and 20% of luminal B tumors are HER2-enriched (Cheang et al., 2009; Prat and Perou, 2011). The PR— and MAPK-dependent regulation of selected genes co-associated with ERBB2 overexpression (FIG. 5A) and SUMO-sensitivity (above) was tested in HER2-amplified but SR-positive BT-474 breast cancer cells that contain constitutively activated MAPKs (Lenferink et al., 2001). RU486 treatment dramatically inhibits BT-474 tumor growth in xenograft models (Liang et al., 2007) and significantly blocks BT-474 cell proliferation in MTT assays conducted over six days in vitro; similar results were observed with the MEK inhibitor, U0126 (data not shown). First the expression of PR target genes (CHN2 and RGS2) primarily regulated by KR (and ERBB2-associated; see FIG. 5A rows) but not WT PR was measured, relative to a control gene not sensitive to PR SUMOylation (ACOT6; upregulated equally by WT and SUMO-deficient PR, FIG. 1F). Remarkably, R5020 treatment induced elevated PR-B Ser294 phosphorylation (lane 2) and robust upregulation of both CHN2 and RGS2 in BT-474 cells: 17-fold and 26-fold respectively (FIG. 5B). Recall that RGS2 expression is weakly sensitive to R5020 treatment in T47D cells expressing WT PR (~2-fold) compared to KR PR (~20-fold) (FIG. 1F). ACOT6 expression was also induced by R5020; expression of all three genes was entirely blocked by antiprogestin RU486 (FIG. 5B). Note that when CHN2 and RGS2 mRNA expression is highest (+R5020; compare lanes 1 and 2), although phospho-Ser294 PR is readily detected, total PR levels are greatly diminished and appear undetectable (lane 2), presumably due to ligand-dependent (proteasome-mediated) downregulation of activated PR species (Lange et al., 2000). Pre-treatment of these cells with the MEK kinase inhibitor, U0126, blocked R5020-induced PR Ser294 phosphorylation and partially, but significantly, diminished both CHN2 and RGS2 expression (FIG. 5B, lane 6). In contrast, the expression of ACOT6, a control gene unaffected by PR SUMO-status, was completely insensitive to MEK kinase inhibition. These data support our hypothesis and demonstrate that phosphorylation events contribute to both expression of the SUMO-deficient PR gene signature and PR-induced proliferation in otherwise unmodified (i.e. containing WT PRs) SR-positive breast cancer cells. Similar to CHN2 and RGS2 (FIG. 5B), it is predicted that a significant number of genes upregulated in ERBB2 overexpressing luminal breast cancers are indeed PR-driven.

The above findings prompted the testing of whether PR gene signatures derived from our cell line models were predictive of tumor grade, node positivity, and patient survival in published human breast tumor cohorts. For example, the Loi et al. dataset (Loi et al., 2007) represents one of the largest collections of survival data from patients whose breast tumors were initially ER positive/PR positive. Metagenes (Huang et al., 2003) were isolated from our T47D microarray dataset representing each sample (PR-null, WT PR, KR PR; with or without R5020 treatment). Using Kaplan Meier survival analysis, patient tumors that express PR-related metagenes (WT or KR, −/+R5020) were compared to all other patient tumors. This analysis revealed that patients in this tumor cohort whose tumors expressed any PR gene signature (i.e. indicative of transcriptionally active PRs) experienced significantly reduced metastasis-free-survival (P=0.000785; FIG. 5C). Notably, patient tumors that did not express a PR-related metagene (FIG. 5C, top curve) were associated with ~80% long-term survival. Presumably, tumors in this group expressed abundant PR, but these receptors are relatively inactive. Consistent with this notion, high PR mRNA levels were associated with good outcome (Loi et al., 2007). The findings suggest that classification of tumors based on PR expression (rather then activity) is misleading. Interestingly, patients whose tumor gene signature resembled that of T47D cells expressing KR +R5020 trended toward poorer outcome (P<0.1). To include the contribution of ligand-independent (KR) PR target genes, we combined patients whose tumors expressed both KR metagenes (KR −R5020, or KR +R5020). These patients experienced significantly reduced survival relative to those whose tumors did not express either of the two KR metagenes (P=0.0261) (FIG. 5D). With respect to nodal status and primary tumor grade, there was no apparent association with expression of the metagenes. These data suggest that PR-dependent transcription, and in particular, the actions of the deSUMOylated (phospho-Ser294) receptor, contribute to tumor progression and poor outcome in a subset of (luminal) breast cancer patients.

PR antagonists, RU486 and aglepristone, stimulate gene expression only in cells expressing SUMO-deficient PR Ligand-dependent PR promoter selectivity is dependent on the phosphorylation and SUMOylation status of the receptor. In addition, PR ligand structure also impacts PR activity, causing agonistic or antagonistic properties on target gene regulation. PR ligands (progesterone and R5020) are strong agonists whereas PR antagonists (RU486, aglepristone, and onapristone) generally block PR transcriptional action; however, these ligands have unique mechanisms of action and may trigger variable levels of agonism/antagonism under different cellular contexts (Cadepond, 1997). Therefore, we used gene expression profiling to investigate the transcriptional effects of these antagonists in T47D breast cancer cells expressing wild type PR (WT), SUMO-deficient PR (KR), or empty vector (PR-Null).

Figure 6:
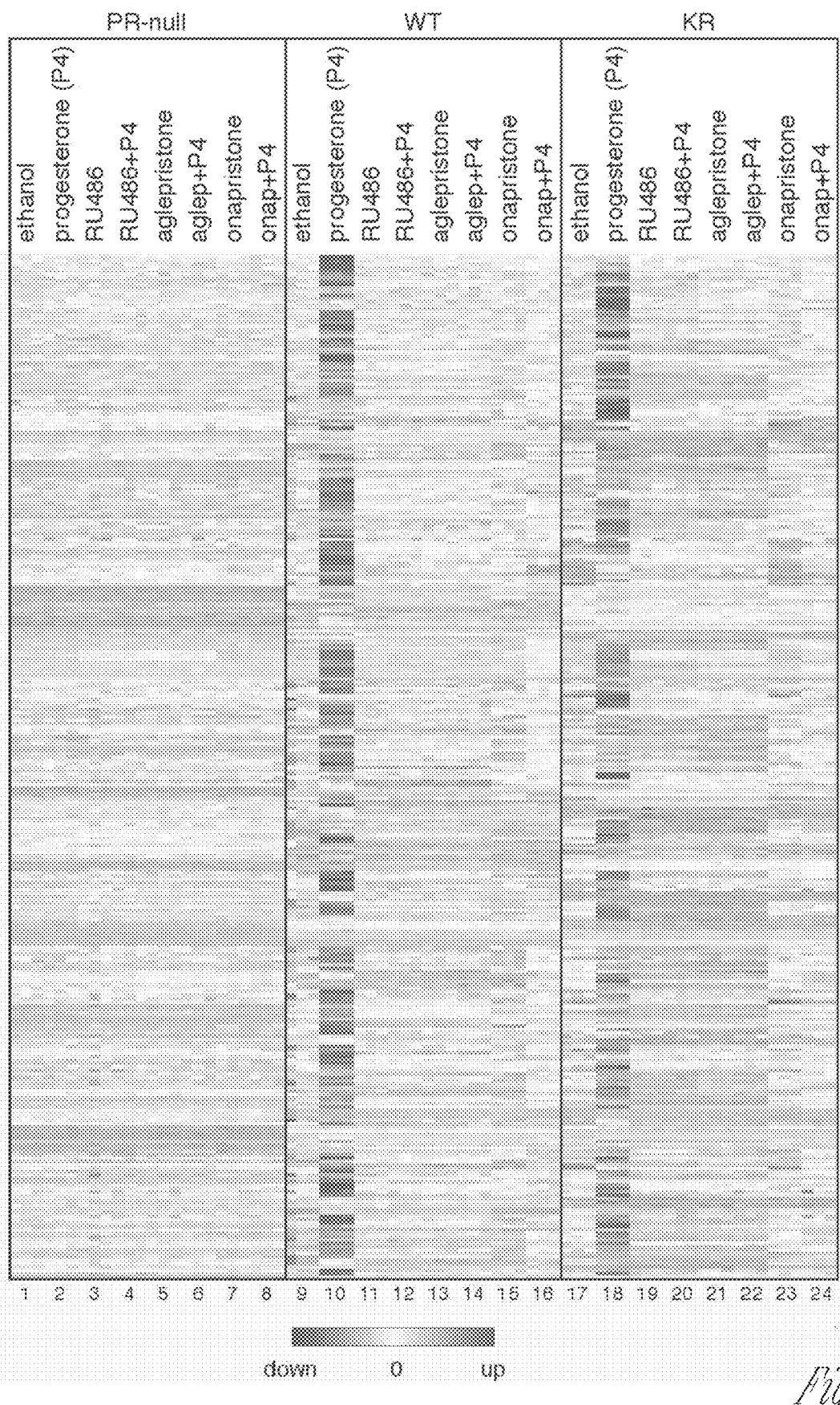
FIG. 6. Top regulated genes in T47D cells treated with progesterone or antiprogestins. Heat map displaying normalized relative expression values for any transcripts that were up- or downregulated (>2 fold, BH adjusted P<0.01) in any possible sample comparison (e.g. progesterone vs. ethanol). Samples were treated for 6 hours and biological triplicates are shown for each treatment group. Genes (rows) were grouped based on unsupervised hierarchal clustering.

Global gene expression profiles were measured using Illumina HT-12v4 microarray platform after each cell line was treated for 6 hours under one of eight possible conditions: (1) ethanol (vehicle control), (2) progesterone ($10^{-8}$ M), (3) RU486 ($10^{-7}$ M), (4) aglepristone ($10^{-7}$ M), (5) onapristone ($10^{-7}$ M), (6) RU486 plus progesterone, (7) aglepristone plus progesterone, or (8) onapristone plus progesterone. Heat map analysis displays the top up- or down regulated genes (FIG. 6) (fold change >2.0 in at least one sample comparison, BH adjusted P<0.01). In cells expressing empty vector (PR-null), significant changes in gene expression dependent on ligand exposure were not observed. Thus, expression profiling in the empty vector cells provided an essential baseline control that allowed one to clearly interpret expression level differences that are dependent on PR and/or ligand. Predictably, many genes are significantly upregulated in both WT and KR cells after progesterone (P4) treatment (FIG. 6, lanes 10, 18). To understand the transcriptional impact of the PR antagonists, all genes that were upregulated (fold change >2.5, BH P value <0.01) after progesterone treatment in either the WT or KR cells were isolated and the expression values for all samples were displayed using a heat map (FIG. 7). Here, PR-null cells were unregulated under any ligand exposure and WT and KR cells treated with only vehicle control (ethanol) were also unregulated. Treatment with RU486 or aglepristone caused many PR target genes to become upregulated, specifically in SUMO-deficient PR (KR) cells but not WT cells (FIG. 7, compare lanes 11-14 and 19-22). Conversely, onapristone (or onapristone plus P4) treatment in KR cells did not cause these PR target genes to be upregulated (FIG. 7, compare lanes 19-22 and 23-24). Unsupervised hierarchal clustering of all samples in FIG. 7 positioned the KR samples treated with ethanol or onapristone in closest relation to the PR-null samples, indicating that KR cells treated with onapristone do not significantly upregulate PR target genes (FIG. 8). Overall, these data suggest that onapristone can successfully inhibit the expression of PR target genes in cells that express hyperactive PR (i.e. PR that is phosphorylated and deSUMOylated) (FIG. 7, compare lanes 18 and 23-34). However, the antiprogestins RU486 and aglepristone have substantial agonistic activity in cells expressing hyperactive PR (FIG. 7, compare lanes 18 and 19-22). Therefore, it is predicted that breast cancer patients with aggressive tumors will benefit substantially from treatments that include PR antagonists, especially onapristone. These data have particular clinical significance because they may help explain the reason why previous phase II clinical trials investigating RU486 as a breast cancer treatment have been unsuccessful (Perrault, 1996), possibly due to the substantial agonistic properties of RU486 in cells expressing hyperactive PR.

Genetic Markers can Identify Tumors Driven by Activated PR

Herein, considerable evidence has been provided that transcriptionally hyperactive PR (that is phosphorylated and deSUMOylated) is a driver of breast cancer cell growth (FIG. 4), is associated with elevated HER2 signaling (FIG. 5), and is a predictor of reduced metastasis-free survival (FIG. 5). Thus, it was sought to identify PR-dependent genetic markers (genes) that can discriminate between cells expressing WT or activated PR (KR) using three independent statistical methods to ensure high sensitivity and specificity.

As described above, two independent gene expression microarray experiments were performed to address different experimental questions. The first experiment investigated progestin-dependent PR target genes, and the second investigated the role of antiprogestins in PR expressing cells. This allowed one to combine the replicate samples from each experiment and investigate the genetic differences between cells expressing WT or KR PR, under progestin exposure.

15 genes (markers) were identified that can discriminate between cells expressing WT or KR PR (Table 1a). To identify these genes, replicate expression values for genes expressed in WT or KR cells were compared, treated with progestin (FIG. 9, compare lanes 10 and 18), and isolated genes that passed pre-determined significance thresholds for P-value, Fold Change, and receiver operator characteristic (ROC) curve analysis (see methods for a detailed discussion of the criteria required for statistical significance). It was also confirmed that 12 known housekeeping genes (30 probe sets) do not pass any significance tests between these groups indicating there were no gene expression differences between these cells (i.e. no technical errors between array samples) (data not shown). Thus, there is great confidence that the expression level of these 15 genes can accurately predict whether cells are driven by "activated PR" (phosphorylated, deSUMOylated PR), or by WT PR.

In the second analysis, genetic differential expression was investigated between KR and WT cells that both had been co-treated with progesterone and plus the antiprogestin onapristone. As can be seen from Table 2, onapristone treatment, with the exception of one gene, completely annulled the significant differential expression of the aforementioned 15 biomarker genes. Table 2 shows the only 8 genes that are significantly differentially expressed between the KR (progesterone plus onapristone) and WT (progesterone plus onapristone) cells. Out of the original 15 genes, only one, namely CDH10, still remained significantly differentially expressed between the two groups. Analysis of the housekeeping genes for this part of the study (data not shown) provided validation of our experimental and analytical methods; none of the 30 probes targeting the 12 housekeeping genes was determined to be significant according to the criteria of significance for our entire study (see methods).

TABLE 2

| Gene | Up or Down Regulated in KR | WT (mean ± SD) n = 5 | KR (mean ± SD) n = 5 | P value α = 1.06E-06 | Fold Change (KR/WT) or -(WT/KR) | ROCAUC | Probe ID | Accession | Probe Sequence |
|---|---|---|---|---|---|---|---|---|---|
| CDH10 | Up | 6.691 ± 0.056 | 10.287 ± 0.033 | 7.08E-08* | 1.538* | 1.00 0* | ILMN_ 1791270 | NM_ 006727.2 | AGCAACCTCACAAACAAGCCGCTTCT GTTAGGTACATGTCCTGCCCTTGC SEQ ID NO: 32 |
| CHRM1 | Down | 8.144 ± 0.026 | 7.348 ± 0.010 | 9.73E-07* | -1.108* | 1.00 0* | ILMN_ 1751689 | NM_ 000738.2 | GCCAGGTGTCCTGACTGTCCTACAAT ATCATTTTCCTGGGAGTGGGAGTC SEQ ID NO: 33 |
| KBTBD11 | Down | 8.396 ± 0.023 | 7.312 ± 0.022 | 5.28E-07* | -1.148* | 1.00 0* | ILMN_ 1784630 | NM_ 014867.1 | GGTAAACTACACCTGTTGAAGGCCAA GTTCAGGGCAGCTGTTGTGATCTG SEQ ID NO: 34 |
| LOC100134134 | Down | 9.028 ± 0.009 | 8.168 ± 0.015 | 1.11E-07* | -1.105* | 1.00 0* | ILMN_ 3237946 | XM_ 001720850.1 | GGAGCTCAAGTGTCGGGAACTGTCTA ACTTCAGGTTGTGTGAGTGCGTTA SEQ ID NO: 35 |
| NFIB | Down | 11.444 ± 0.026 | 10.319 ± 0.017 | 4.01E-07* | -1.109* | 1.00 0* | ILMN_ 1778991 | NM_ 005596.2 | ATCACTATTCCTGGTTATCTCACCAA CGAAGGCTAGGAGGCGGCGTCAGA SEQ ID NO: 36 |
| VCX-C | Up | 9.035 ± 0.031 | 10.531 ± 0.038 | 7.32E-07* | 1.166* | 1.00 0* | ILMN_ 2166716 | NM_ 001001888.1 | GGTGGAGGAACCACTGAGTCAGGAGA GCGAGATGGAAGAACCACTGAGTC SEQ ID NO: 37 |
| BCHE | Up | 6.673 ± 0.065 | 8.162 ± 0.146 | 8.59E-05 | 1.223* | 1.00 0* | ILMN_ 2176592 | NM_ 000055.1 | CCCCCAAAATTATCAGTGCTCTGCT TTTAGTCACGTGTATTTTCATTAC SEQ ID NO: 38 |
| LCN2 | Down | 9.364 ± 0.030 | 7.714 ± 0.061 | 1.93E-06 | -1.214* | 1.00 0* | ILMN_ 1692223 | NM_ 005564.3 | CCACATCGTCTTCCCTGTCCCAATCG ACCAGTGTATCGACGGCTGAGTGC SEQ ID NO: 39 |

Top 8 most significant genes with differential expression between progestin-stimulated and Onapristone-treated KR and WT cells.
(*) Statistically significant according to the criteria of the respective method.

In the third analysis, genetic differential expression between KR and WT cells that both had been co-treated with progesterone plus the antiprogestin RU486 was investigated. As can be seen from Table 3, RU486 treatment, with the exception of one gene, completely annulled the significant differential expression of the aforementioned 15 biomarker genes. Table 3 shows the only 7 genes that are significantly differentially expressed between the KR (progesterone plus RU486) and WT (progesterone plus RU486) cells. Out of the original 15 genes, only one, namely CDH10, still remained significantly differentially expressed between the two groups. Analysis of the housekeeping genes for this part of the study (data not shown) provided validation of the experimental and analytical methods; none of the 30 probes targeting the 12 housekeeping genes was determined to be significant according to the criteria of significance for our entire study (see methods).

TABLE 3

| Gene | Up or Down Regulated in KR | WT (mean ± SD) n = 5 | KR (mean ± SD) n = 5 | P value α = 1.06E-06 | Fold Change (KR/WT) or -(WT/KR) | ROCAUC | Probe ID | Accession | Probe Sequence |
|---|---|---|---|---|---|---|---|---|---|
| CCND1 | Up | 10.127 ± 0.016 | 11.353 ± 0.037 | 7.40E-07* | 1.121* | 1.00 0* | ILMN_ 1688480 | NM_ 053056.2 | CGGCGCTTCCCAGCACCAACATGTAA CCGGCATGTTTCCAGCAGAAGACA SEQ ID NO: 40 |
| CDH10 | Up | 6.762 ± 0.027 | 9.958 ± 0.051 | 7.06E-08* | 1.473* | 1.00 0* | ILMN_ 1791270 | NM_ 006727.2 | AGCAACCTCACAAACAAGCCGCTTCT GTTAGGTACATGTCCTGCCCTTGC SEQ ID NO: 41 |
| FGFBP1 | Down | 8.191 ± 0.007 | 7.270 ± 0.025 | 4.21E-07* | -1.127* | 1.00 0* | ILMN_ 1785404 | NM_ 005130.3 | CGATGTTCAGAGGCTGTTTCCTGCAG CATGTATTTCCATGGCCCACACAG SEQ ID NO: 42 |
| GSTM3 | Up | 7.766 ± 0.019 | 8.854 ± 0.020 | 2.71E-07* | 1.140* | 1.00 0* | ILMN_ 1736184 | NM_ 000849.3 | GACACAGAACACAGACGCCTTACTGG CAACCTGCTTTCAAGACCCCTGTC SEQ ID NO: 43 |

TABLE 3-continued

| Gene | Up or Down Regulated in KR | WT (mean ± SD) n = 5 | KR (mean ± SD) n = 5 | P value α = 1.06E-06 | Fold Change (KR/WT) or -(WT/KR) | ROCAUC | Probe ID | Accession | Probe Sequence |
|---|---|---|---|---|---|---|---|---|---|
| HS.10862 (AK4) | Up | 9.654 ± 0.033 | 10.797 ± 0.016 | 6.93E-07* | 1.118* | 1.00 0* | ILMN_ 1843198 | AK026966 | GTGTTTATGATGAGTCAGAGTGCTTT TCCTCGGTGGGACAGTTGCTGGCC SEQ ID NO: 44 |
| PHACTR3 | Up | 6.745 ± 0.042 | 8.901 ± 0.073 | 1.54E-06 | 1.320* | 1.00 0* | ILMN_ 1666222 | NM_ 183246.1 | CAGTTCTGCAGTGTAATGGAGGACGG GCAACGTGCATGTGCAGGCTCACC SEQ ID NO: 45 |
| ACOT6 | Up | 6.745 ± 0.039 | 8.716 ± 0.077 | 2.42E-06 | 1.292* | 1.00 0* | ILMN_ 2156699 | NM_ 001037162.1 | GAGCCAAAGGCTCACTCAAAGGCACA GGTAGATGCCTGGCAGCAAATTCA SEQ ID NO: 46 |

Top 7 most significant genes with differential expression between progestin-stimulated and RU486-treated KR and WT cells. (*) Statistically significant according to the criteria of the respective method.

Next, whether treating KR cells with the antiprogestin onapristone can reverse the transcriptional differences observed above was tested (Table 1a). The same stringent analysis was repeated comparing the following two groups: cells expressing KR treated with onapristone plus progesterone, and cells expressing WT treated with vehicle control (ethanol). It was found that the two groups were genetically indistinguishable apart from 5 significantly differentially expressed genes. Clearly progestins can activate hundreds on PR target genes, yet only 5 genes were identified that were significantly different between these two groups (Table 4). These data suggest that onapristone treatment (even in the presence of progesterone exposure) can effectively reverse the effects of progesterone exposure in cells expressing activated PR. Again, housekeeping control genes were not significantly differentially expressed between those two groups (data not shown).

Finally, whether treating KR cells with the antiprogestin onapristone can reverse the transcriptional differences observed above (Table 1a) was investigated. A comparative analysis between WT cells treated with (progesterone plus onapristone) and WT cells that had only been treated with ethanol (vehicle control) was performed. As can be seen from Table 5, there was only one gene that remained significantly differentially expressed between those two groups. This clearly demonstrates that treatment with the antiprogestin onapristone can almost completely reverse the transcriptional differences induced by the stimulation with progesterone in the cells with a WT PR receptor. Analysis of the housekeeping genes for this part of the study showed that none of the 30 probes targeting the 12 housekeeping genes was determined to be significant according to the criteria of significance for the entire study (see methods).

TABLE 4

| Gene | Up or Down Regulated in KR | WT (mean ± SD) n = 5 | KR (mean ± SD) n = 5 | P value α = 1.06E-06 | Fold Change (KR/WT) or -(WT/KR) | ROCAUC | Probe ID | Accession | Probe Sequence |
|---|---|---|---|---|---|---|---|---|---|
| CDH10 | Up | 6.781 ± 0.115 | 10.287 ± 0.033 | 4.33E-09* | 1.517* | 1.00 0* | ILMN_ 1791270 | NM_ 006727.2 | AGCAACCTCACAAACAAGCCGCTTCTG TTAGGTACATGTCCTGCCCTTGC SEQ ID NO: 47 |
| ABP1 | Up | 6.734 ± 0.086 | 7.951 ± 0.070 | 8.39E-07* | 1.181* | 1.00 0* | ILMN_ 1731433 | NM_ 001091.2 | TATAGACCTGTGTGACCAGCCCCCAGT TCCTCCCCCAGTTCCTCCCAGGA SEQ ID NO: 48 |
| FLJ35767 | Up | 7.354 ± 0.086 | 8.651 ± 0.033 | 3.04E-07* | 1.176* | 1.00 0* | ILMN_ 1730351 | NM_ 207459.1 | TCTGGTCTACAGTGGAGGGAGAGCTGG TTTTAAATGTTGGCCGTTGATGC SEQ ID NO: 49 |
| NLGN1 | Up | 7.731 ± 0.039 | 8.530 ± 0.073 | 8.01E-07* | 1.103* | 1.00 0* | ILMN_ 1739521 | NM_ 014932.2 | GATGGAACCAACTTTGTACATCTTGGC CATGTCACTGGTCATTGTGTGAA SEQ ID NO: 50 |
| C6ORF81 (ARMC12) | Up | 7.107 ± 0.144 | 8.587 ± 0.136 | 7.32E-06 | 1.208* | 1.00 0* | ILMN_ 1712616 | NM_ 145028.3 | CGACTGGCAGACCGACTACTTGCCCTG GTCATCCACCCTGAGGAAGATGT SEQ ID NO: 51 |

The 5 genes with significantly differential expression between progesterone-stimulated and onapristone-treated KR cells and WT cells treated with vehicle control (ethanol). (*) Statistically significant according to the criteria of the respective method.

TABLE 5

| Gene | Up or Down Regulated in KR | WT (mean ± SD) n = 5 | KR (mean ± SD) n = 5 | P value α = 1.06E-06 | Fold Change (KR/WT) or -(WT/KR) | ROCAUC | Probe ID | Accession | Probe Sequence |
|---|---|---|---|---|---|---|---|---|---|
| GPR124 | Up | 6.651 ± 0.063 | 7.707 ± 0.068 | 5.27E-07* | 1.159* | 1.000* | ILMN_NM_17730032777.659 | | CTAGGGTTCCCTCCCAGTCTTCACAT CACTCTGGCCTCATCACCAAGGTG SEQ ID NO: 52 |

The only gene with significantly differential expression between progesterone-stimulated and onapristone-treated WT cells and WT cells treated with vehicle control (ethanol). (*) Statistically significant according to the criteria of the respective method.

Genes Upregulated by Activated PR are Suppressed by Antiprogestins

The statistical analyses described above provided strong measures of sensitivity and specificity to confidently identify 15 genes that can discriminate between cells expressing WT or SUMO-deficient PR in the presence of progestin. However, there are many other PR target genes that are specifically upregulated in response to progestin treatment (i.e. the ratio of P4/ethanol). PR target genes which are induced by progestins, specifically in cells expressing activated PR (KR), compared to WT was investigated. These gene products are likely the drivers of an activated PR transcriptional program. In fact, these types of PR genes as the ligand-dependent "KR>WT" gene signature of 151 genes (FIG. 2B, 4.1) was described.

The microarray studies above each contained very similar treatment conditions that could be compared directly: vehicle or progestin treated cells expressing WT or KR PR. The only difference between these experiments was the progestin treatment, R5020 in the first experiment and the natural PR ligand progesterone (P4) in the second experiment. Therefore, by performing a second microarray experiment under the almost identical conditions, there was an opportunity to compare the results from each experiment and converge on a set of highly reproducible progestin-dependent PR target genes that were specifically upregulated in cells expressing SUMO-deficient PR, compared to WT PR. As a result, a robust list of genes was identified that are upregulated in breast cancer cells expressing "activated PR," where PR is phosphorylated and deSUMOylated.

In the first microarray experiment, 151 progestin-dependent PR target genes that were specifically upregulated (fold change >1.5, BH adjusted P<0.01) in cells expressing SUMO-deficient PR, compared to WT PR (FIG. 4.1), were identified. This analysis was repeated in the second microarray study and the overlapping genes were isolated from both experiments. Therefore, the list from 151 genes was narrowed to 29 genes that were upregulated in response to progestin treatment (R5020 or progesterone) specifically in cells expressing SUMO-deficient PR, compared to WT PR (FIG. 10, compare lanes 10 and 18). It is believed that these 29 genes are highly reproducible markers of SUMO-deficient PR expression in response to progestin (i.e. five total replicates, from two independent experiments, treated with two different PR agonists: R5020 and progesterone).

Expression data from the second microarray experiment showed that RU486 and aglepristone had agonistic properties in cells expressing SUMO-deficient PR, whereas onapristone was an effective antagonist in cells expressing WT or KR PR. Therefore, the "activated PR" gene list was further narrowed by eliminating any of those 29 genes that were even moderately stimulated by onapristone treatment, alone (none) or by onapristone plus P4 treatment (13 genes). This resulted in a final list of 16 genes (Table 1b, FIG. 11) that include MSX2, MAP1A, and PDK4. These three genes were extensively studied in multiple gene expression and ChIP experiments illustrating their specific regulation in cells expressing SUMO-deficient PR. Indeed, 7 of these 16 genes are involved in Cancer related functions, as determined by Ingenuity Pathway Analysis. It is concluded that these 16 PR target genes are robustly upregulated by progestins when PR is phosphorylated and deSUMOylated and their gene products drive increased tumor aggressiveness (FIGS. 2, 4, 5).

TABLE 1b

| Gene | Up or Down Regulated in KR | Probe ID | Accession | Probe Sequence |
|---|---|---|---|---|
| THY1 | Up | ILMN_1779875 | NM_006288.2 | CTGAGGCAAGCCATGGAGTGAGACCCAGGAGCCGGACACTTCTCAGGAAA SEQ ID NO: 16 |
| KLF9 | Up | ILMN_1778523 | NM_001206.2 | GCCCTTCACCATTGTGGAATGATGCCCTGGCTTTAAGGTTTAGCTCCACA SEQ ID NO: 17 |
| SPINK5L3 | Up | ILMN_1697543 | NM_001040129.2 | GCAGACTGCCCCAATGTGACAGCACCTGTTTGTGCCTCAAATGGCCACAC SEQ ID NO: 18 |
| PHLDA1 | Up | ILMN_1687978 | NM_007350.3 | AACAGTCTCTCCGCCCCGCACCAGATCAAGTAGTTTGGACATCACCCTAC SEQ ID NO: 19 |
| MAP1A | Up | ILMN_1701558 | NM_002373.4 | CCCAAGCAAGCCAGTGAGCAGCCCTGCCAGACTACTGCCAGACTGAGAAA SEQ ID NO: 20 |
| SPRYD5 | Up | ILMN_1753648 | NM_032681.1 | TCCCTGATATACACCATCCCCAATTGCTCCTTCTCACCTCCTCTCAGGCC SEQ ID NO: 21 |

TABLE 1b-continued

| Gene | Up or Down Regulated in KR | Probe ID | Accession | Probe Sequence |
|---|---|---|---|---|
| ATG12 | Up | ILMN_2188204 | NM_004707.2 | GAGTCGTGATTGTACCACTGCATTCCTGCTGAGCAACAGAGTGAGACCCC SEQ ID NO: 22 |
| PDK4 | Up | ILMN_1684982 | NM_002612.3 | CAGAAGTCCTAGACAGTGACATTTCTTAATGGTGGGAGTCCAGCTCATGC SEQ ID NO: 23 |
| MSX2 | Up | ILMN_1766951 | NM_002449.4 | AGGTACATTCATCCTCACAGATTGCAAAGGTGATTTGGGTGGGGGTTTAG SEQ ID NO: 24 |
| TUBA3E | Up | ILMN_1652464 | NM_207312.1 | GGTCCCCAAAGACGTCAATGCGGCCATCGCCACCATCAAGACCAAGCGCA SEQ ID NO: 25 |
| TSC22D1 | Up | ILMN_1692177 | NM_006022.2 | TCCCAATGGTGTAGACCAGTGGCGATGGATCTAGGAGTTTACCAACTGAG SEQ ID NO: 26 |
| TUBA3D | Up | ILMN_2215639 | NM_080386.1 | TCCCCTGCCACCCCCGGGATGGCTGCTTCCAAGTTGTTTGCAATTAAAGG SEQ ID NO: 27 |
| KHDRBS3 | Up | ILMN_1691747 | NM_006558.1 | AGGCACCTTCAGCGAGGACAGCAAAGGGCGTCTACAGAGACCAGCCATAT SEQ ID NO: 28 |
| UTS2D | Up | ILMN_2180232 | NM_198152.2 | GCTGGTATATCCAGTGCATTGTTGGCACCATGGGACCAGAAGGTGGTGAC SEQ ID NO: 29 |
| SLC35C1 | Up | ILMN_1680104 | NM_018389.3 | AGGGTGGCTTGCAGTCCCTGGCCCTTCTGGTGGGCATTTGGTATGTCCTT SEQ ID NO: 30 |
| KIAA0513 | Up | ILMN_1693233 | NM_014732.2 | CTTCTTGAACCTGGTGGCCCCCGTTGGAACTATCAGTGGCGTCTCCCATG SEQ ID NO: 31 |

Discussion

In this study, gene expression profiling was performed to better understand how PR SUMO modification impacts transcriptional activity and promoter selection. Using newly engineered breast cancer cell line models, a (deSUMOylated) PR-driven gene signature was identified that is present in human tumors and associated with decreased patient survival. Previously, it was shown that PR phosphorylation at Ser294 antagonizes PR SUMOylation at Lys388 (Daniel et al., 2007a). Herein, the novel data suggest that breast cancer cells may utilize this mechanism to shift PR transcriptional action toward target genes that drive cell proliferation and pro-survival pathways (FIG. 4, 5). Using bioinformatics to analyze global gene expression levels (FIG. 1), dramatic differences in transcriptional responses were identified between WT and deSUMOylated PRs that were further characterized by ChIP analysis as alterations in promoter/enhancer selectivity (FIG. 3, 3.1). Additionally, treatment of unmodified breast cancer cells (or cells expressing only WT PR-B) with EGF further implicated PR Ser294 phosphorylation (PR deSUMOylation) in transcriptional derepression of selected PR target genes (FIG. 2). Notably, genes specifically upregulated by SUMO-deficient PR (i.e. phospho-PR driven) are significantly associated with genes that are highly expressed in ERBB2-positive human breast tumors and cell lines; the studies support a mechanistic link between phosphorylated (deSUMOylated) PR-B-specific transcriptional action and expression of a subset of ERBB2-associated genes (FIG. 5). Collectively, the data provide a strong rationale for further study into mechanisms of phospho-PR-dependent regulation of transcription and the potential contribution of this activity to early or rapid breast cancer progression towards endocrine resistance.

Gene expression analysis identifies SUMOylation-sensitive PR target genes. It was previously reported that PR SUMOylation is transcriptionally repressive at a limited number of endogenous gene loci, including HBEGF, IRS1, and STC1 (Daniel et al., 2007a; Daniel and Lange, 2009); all three gene products are known to contribute to breast cancer cell proliferation (Beerli and Hynes, 1996; Byron et al., 2006; Chang et al., 2003). Herein, a comprehensive set of experiments were performed to measure the regulation of endogenous PR target genes using current microarray techniques for whole genome expression profiling in T47D cells expressing either WT PR or SUMO-deficient mutant K388R PR (phospho-mimic), treated with or without the synthetic progestin, R5020. Apart from the investigation of the role of reversible PR SUMOylation, this microarray dataset provides an updated well-controlled analysis (using newly created vector matched cell lines) of WT PR-B transcriptional action in response to progestin treatment. Rigorous independent experiments were performed using additional cell lines and novel cell line clones expressing either constitutive (stable) or inducible WT or mutant PRs, and gene expression levels were measured using distinct microarray platforms (Illumina and Affymetrix). Indeed, the analysis confirmed 70% of previously identified PR target genes (Jacobsen et al., 2005; Richer et al., 2002) but also uncovered hundreds of novel PR target genes; many of these are ligand-independent examples. This dataset provides a powerful resource for future studies investigating mechanisms of ligand-dependent and -independent PR-mediated transcriptional regulation.

Notably, the comparison of genes regulated by WT versus KR PRs revealed considerable overlap suggesting that the majority of PR regulated genes are relatively insensitive to dynamic modification of PR-B by SUMOylation/deSUMOylation (FIG. 1D-E, overlapping Venn categories). However, within these categories, many genes displayed intermediate (varied) levels of expression when regulated by either WT or KR PR, suggesting that multiple mechanisms impact PR mediated transcription, in part according to PR SUMOylation status. Conversely, smaller subsets of genes were highly sensitive to the SUMOylation-status of PR (FIG. 1D-E, all Venn categories except the overlapping regions). Surprisingly, these subsets included genes that were both up and down regulated by KR PR relative to WT controls, suggesting that SUMOylation of PR-B can be either repressive or activating, depending on the promoter context. For example, while many proliferative genes were increased, a number of known tumor suppressor genes were repressed by deSUMOylated (KR) PR.

Based on the previous studies (Daniel et al., 2007a; Daniel and Lange, 2009), it was predicted that phospho-Ser294-PRs (i.e. that are primarily deSUMOylated) mediate a shift in gene regulation that profoundly affects cancer cell phenotypes. Thus, herein the goal was to identify these genes and understand the mechanism(s) of their differential regulation (by WT and KR PR) using entirely new breast cancer cell models. In cells stably expressing S294A PR, a receptor unable to be phosphorylated on Ser294 and thus heavily SUMOylated (Daniel et al., 2007a; Lange et al., 2000), the expression of selected KR-upregulated genes (e.g. MSX2 etc.) was entirely blocked; transcriptional upregulation was rescued in cells expressing the PR K388R/S294A double mutant (KRSA; FIG. 2C). These data demonstrate that PR SUMO modification dominantly represses transcription at PR target genes that are effectively "derepressed" in response to phosphorylation events. For example, PR-dependent MSX2 and RGS2 mRNA expression was greatly augmented upon EGF treatment of cells expressing WT PR (FIG. 2D). It was concluded that PR phosphorylation and deSUMOylation affects global gene expression patterns by dramatically altering PR transcriptional activity and promoter selectivity in breast cancer cells.

Mechanisms impacting PR promoter selectivity. The microarray studies clearly demonstrate that PR SUMO modification alters the expression of a broad range of PR target genes but has no effect on others. Little is known about the mechanisms of promoter selectivity. However, this question has been addressed with regard to other SR family members (Tang et al., 2011). SR interactions with chromatin are highly dynamic and occur as a rapid and continuous exchange (Hager et al., 2009). Thus, concentrated regions of transcription factor "binding" (as measured by ChIP) actually reflect a shift in the equilibrium towards increased transcription factor occupancy at that region. Multiple factors may influence this equilibrium, such as SR binding to consensus DNA sequences, participation of coregulatory factors within multi-protein complexes and/or sequestration of SRs to specific cellular locations, as well as histone modifications that regulate chromatin accessibility. Additionally, studies of restriction enzymes have revealed mechanisms that facilitate enzyme binding to consensus sequences up to 1000 times faster than is possible via diffusion alone, suggesting the existence of ancillary factors that facilitate binding (Halford and Marko, 2004). Similarly, recent work has determined that specific proteins called "pioneer factors" aid in chromatin remodeling and localization of SR transcription factors to nearby genomic binding sites (enhancers) in developmental tissue or cancer specific settings (Carroll et al., 2005; Hurtado et al., 2011; Lupien et al., 2008).

Modification of protein substrates by the addition of SUMO molecules can influence protein-protein interactions and/or alter protein stability, localization, or transcriptional activity (reviewed in (Geiss-Friedlander and Melchior, 2007)). PR SUMOylation (at Lys388) most frequently represses PR transcriptional activity (but can increase it in a promoter dependent manner; FIG. 1F BCL2L11 and DNAL11), and tends to slow the rate of ligand-dependent PR downregulation via proteasome mediated turnover (Daniel et al., 2007a), but does not appreciably alter PR location (Man et al., 2006). Numerous genes in our analyses behaved like MSX2; expression was substantially upregulated by SUMO-deficient KR PR, but not WT PR (FIG. 2C). Additionally, KR PR occupied the MSX2 enhancer 2-3 times more than WT receptor (FIG. 3B). The finding that increased levels of KR PR are recruited to this locus and associated with increased MSX2 mRNA expression, suggests that PR SUMOylation (in the context of SUMO-sensitive enhancer regions and chromatin) alters co-factor interactions that occur at the level of PR DNA binding. Related to this finding, PIAS3, a PR SUMOylation E3 ligase, directly inhibits PR binding to PRE DNA sequences in vitro (Man et al., 2006). Thus, PIAS3-mediated SUMO conjugation to WT (but not KR) PR may prevent efficient receptor binding to selected PRE sequences, thus subsequently shifting the equilibrium away from PR occupancy at these loci. How this mechanism might be sequence specific or promoter specific remains to be determined.

Promoter structure is likely to be an important determinant of promoter selection by SUMOylated transcription factors, including PR. Holmstrom et. al (Holmstrom et al., 2008) found that SUMOylated GR requires stable interaction with DNA containing multiple GR binding sites in order to efficiently inhibit transcription. Interestingly, glucocorticoid receptor (GR) SUMOylation also selectively affects the transcriptional induction of linked endogenous genes (Holmstrom et al., 2008). Related to this finding, recent chromatin modification mapping studies have revealed that histone H3 Lys4 mono- and dimethylation (H3K4me1/2) at enhancers is associated with transcriptionally active genes (He et al., 2010; Heintzman et al., 2007). Indeed, regions of transcription factor accessibility to DNA response elements were first identified as DNase or MNase hypersensitive sites because these regions were relatively free from occupied nucleosomes (ENCODE Project Consortium, 2007). H3K4me2 is believed to be an epigenetic marker at functional enhancers that may recruit additional proteins (pioneer factors) to facilitate nucleosome remodeling and accessibility of the region for transcription factor binding (He et al., 2010). We have not identified the pioneer factors for PR recruitment, but in this study, we observe elevated H3K4 dimethylation at the MSX2 enhancer in cells expressing SUMO-deficient KR PR, compared to WT PR. In this model, deSUMOylated PR may preferentially recruit the histone methyltransferase, MLL2 (i.e. to the MSX2 enhancer), resulting in sustained H3K4 dimethylation that allows formation of productive transcriptional complexes at active sites that are normally repressed by SUMOylated receptors.

Finally, DNA binding specificity for SRs is also highly dependent on sequence composition. Studies investigating GR demonstrate that single base pair changes in consensus GRE/PRE sequences can dramatically affect receptor binding and cofactor interaction (Meijsing et al., 2009). Thus, DNA itself appears to be a sequence specific allosteric ligand for SRs, which can directly influence promoter selectivity and transcriptional consequences. SUMOylated GRs appear to prefer near-perfect consensus GR-binding sites (Holmstrom et al., 2008). Notably, as with PR, site-specific phosphorylation of GR also alters its promoter preference (Blind and Garabedian, 2008). It is currently unknown whether SUMOylated versus deSUMOylated PRs differentially recognize different PRE sequences (i.e. we did not perform ChIP-seq experiments to identify all PR-binding sites). However, this seems plausible because SUMO modifications can dramatically alter substrate protein conformation. Clearly, deSUMOylated PRs are capable of recruiting abundant PR coactivators (CBP, MLL2) to enhancer regions; the more rapid or stable creation of functional transcriptional complexes may account for the increased "sampling" or use of selected promoters by KR relative to WT PRs (FIG. 3). The analysis revealed no obvious global signal(s) that could account for preferential repression or activation of selected enhancer regions over others by SUMOylated or deSUMOylated PRs.

Clinical implications of deSUMOylated PR gene expression. Targeting ER function in luminal breast cancers with selective ER modulators (SERMs [e.g. tamoxifen], antiestrogens [e.g. fulvestrant]) and/or aromatase inhibitors (e.g. anastrozole, letrozole, or exemestane) is very effective for a majority of women (Early Breast Cancer Trialists' Collaborative Group, 2005; Goss et al., 2011). Indeed, because SR cross-talk with growth factor signaling pathways is extensive and tumors tend to progress towards endocrine resistance under the influence of heightened growth factor signaling, combination therapies targeting both ER and ERBB receptors enhance progression free survival (Johnston et al., 2009; Kaufman et al., 2009). Herein disclosed is a unique set of genes that were upregulated, or derepressed, by deSUMOylated (phospho-mimic) PR species under both ligand-dependent (151 genes) and ligand-independent conditions (92 genes) (FIG. 4.1). Elevated expression of these genes may signify tumors that are primarily driven by hyperactive phospho-PR (deSUMOylated) species, particularly in cancers characterized by activated growth factor signaling cascades. For example, MAPK and CDK2 or CDK4/6 are known drivers of breast cancer progression that likely induce persistent PR Ser294 phosphorylation in some breast tumors (FIG. 1A). it is predicted that patients with luminal-type (ER positive/PR positive) breast tumors that express this "phospho-PR" gene signature exist (see FIG. 1A and FIG. 4.1) and that this subset, if identified early, could benefit from endocrine therapies that include the use of highly selective antiprogestins, perhaps in combination with currently used antiestrogens or aromatase inhibitors and/or growth factor pathway inhibition.

Indeed, much research has shown that PR is not only a clinical marker of functional ER expression, but also an important independent driver of tumor progression (reviewed in (Daniel et al., 2011)). Notably, as SR positive luminal A-type tumors progress towards a more aggressive growth factor-high luminal B-type phenotype, SR expression begins to decline, starting with PR loss. These poor prognosis luminal-B-type tumors are often clinically characterized as ER positive/PR-low or null and are more likely to become endocrine resistant. It was shown previously that deSUMOylated phospho-PR function as hyperactive receptors but also turnover rapidly via the ubiquitin-proteasome pathway (FIG. 1B and (Lange et al., 2000)). In fact, when PR-dependent transcription peaks, as measured by RT-qPCR of endogenous gene readouts (via mRNA levels, as in FIG. 5B) or using reporter genes, PR protein levels are virtually undetectable (Daniel et al., 2007b). This finding raises the important question of whether PR is also hyperactive in a subset of breast tumors that are clinically defined as PR-low or null (i.e. as generally measured by methods of total protein detection in clinical settings). Interestingly, breast tumors are capable of de novo progesterone synthesis, a process mediated by growth factor-dependent signaling (Locke et al., 2008; Su et al., 2011; Suzuki et al., 2005). Tumor-cell (local) production of progesterone may contribute to sustained PR action (i.e. at ligand-dependent genes) in more aggressive ER positive/PR positive tumors.

Surprisingly, herein it is disclosed that breast cancer cells expressing deSUMOylated phospho-PR drive the expression of cell proliferation genes (FIG. 4.1), many directly involved in positive regulation of the ERBB/MAPK signaling pathway, thus setting up a type of "feed-forward" vicious cycle that is clearly associated with tumor progression (Amit et al., 2007; Prat and Perou, 2011). The data suggest that phospho-PR may act as a driver of this transition (i.e. tumor progression towards the gain of growth factor-driven pathways that can precede SR loss) as indicated by significant similarity to our uniquely defined PR signatures (FIG. 4.1). The findings are supported by available clinical data from the Women's Health Initiative and Million Women's Study showing that breast tumors that arose in women taking a progestin as part of HRT were more frequent, larger, and of higher grade relative to control groups (Chlebowski et al., 2010; Million Women Study Collaborators, 2003). Remarkably, a recent analysis of these data demonstrated that estrogen-only HRT may actually protect women from invasive breast cancer (Anderson et al., 2012; LaCroix et al., 2011). Taken together with the work of others (Labriola et al., 2003; Musgrove and Sutherland, 2009; Salatino et al., 2004), the data support the concept that targeting PR action in breast cancer patients may be highly beneficial, especially for patients that become resistant to anti-estrogens or aromatase inhibitors. Of note, roughly 40% of patients will initially fail or eventually develop resistance to endocrine therapies aimed solely at targeting estrogen action; this represents a large and underserved population.

The intense study surrounding the molecular subtypes of breast cancer has provided great insights into genetic characteristics of this heterogeneous cancer (Prat and Perou, 2011), but current targeted therapies are still focused on a small number of clinical-pathological markers. While it is true that knowing the status of various markers (e.g. ER, PR, and HER2) has prognostic value and can inform current therapies, measuring mRNA levels for an expanded number of relevant genes (i.e. gene signatures) will provide more sensitive and specific information regarding the genetic pathways active in the tumor. This knowledge could be used to inform clinical decisions, especially when targeted therapies are considered. Thus, there has been rapid expansion of prognostic mRNA expression based assays to classify breast tumors (Loi et al., 2007; Paik et al., 2004; Parker et al., 2009; van't Veer et al., 2002). However, currently available prognostic signatures fail to link changes in gene expression to the molecular drivers present in a given tumor. Here, a PR-dependent gene signature has been identified that is more likely to characterize aggressive tumors (FIG. 5D, 4.1). The studies implicate deSUMOylated phospho-PRs as major drivers of this phenotype. Although validation studies in animal models are required (in progress), the studies strongly support the use of antiprogestins as valuable additions to state-of-the-art antiestrogen-based endocrine therapies. Identification of patients with PR-driven tumors (that contain the activated PR gene signature) may allow intervention aimed at preventing the development of endocrine resistance and provide patients with additional clinical benefit.

Summary

Herein, it has been shown that PR transcriptional action is more complex than originally thought, insofar as PR are sensors for mitogenic stimuli whereby phosphorylation events drive the receptor toward the deSUMOylated state, resulting in a dramatically altered transcriptional program that promotes cell proliferation and pro-survival. A deSUMOylated phospho-PR gene signature was identified of both known and novel PR target genes that is a marker of hyperactive PR signaling in breast cancer cell models; this signature is indeed also present in a subset of patients with recurrent breast cancer (FIGS. 1A and 5D). This unique signature can provide a valuable prognostic measure for identifying patients whose tumors are likely to progress and/or become endocrine-resistant (i.e. to estrogen targeted therapies).

BIBLIOGRAPHY

Amit, I., et al. (2007). Nat Genet 39, 503-512.
Anderson, G L., et al. (2012). Lancet Oncol.
Barski, A., et al. (2007). Cell 129, 823-837.
Beerli, R. R., and Hynes, N. E. (1996). J Biol Chem 271, 6071-6076.
Benjamini, Y., and Hochberg, Y. (1995). J Roy Stat Soc B Met 57, 289-300.
Blind and Garabedian (2008). J Steroid Biochem Mol Biol 109, 150-157.
Bonnefoi, H., et al. (2007). Lancet Oncol 8, 1071-1078.
Byron, S. A., et al. (2006). British journal of cancer 95, 1220-1228.
Carroll, J. S., et al. (2005). Cell 122, 33-43.
Cadepond, F, et al. (1997). Annu Rev Med, 48, 129-56.
Cartharius, K., et al. (2005). Bioinformatics 21, 2933-2942.
Chang, A. C., et al. (2003). Endocr Relat Cancer 10, 359-373.
Cheang, M. C., et al. (2009). JNCI 101, 736-750.
Chlebowski, R. T., et al. (2010). JAMA 304, 1684-1692.
Chlebowski, R. T., et al. (2003). Jama 289, 3243-3253.
Chlebowski, et al. (2009). The New England journal of medicine 360, 573-587.
Clemm, D. L., et al. (2000). Mol Endocrinol 14, 52-65.
Covington, K., and Parikh, A. (2011). The Red-R Journal 1, www.red-r.org/journal/published-articles/1-08082011-red-r-framework-integrated-discovery.
Crouch, S. P., et al. (1993). J Immunol Methods 160, 81-88.
Daniel, A. R., et al. (2007a). Mol Endocrinol 21, 2890-2906.
Daniel et al. (2011). Expert review of endocrinology & metabolism 6, 359-369.
Daniel, A. R., et al. (2009). Mol Cell Endocrinol 308, 47-52.
Daniel, A. R., and Lange, C. A. (2009). PNAS 106, 14287-14292.
Daniel, A. R., et al. (2007b). Steroids 72, 188-201.
De Vivo, I., et al. (2002). Proc Natl Acad Sci USA 99, 12263-12268.
di Bari, M. G., et al. (2009). J Cell Physiol 219, 659-666.
Early Breast Cancer Trialists' Collaborative Group (2005). Lancet 365, 1687-1717.
ENCODE Project Consortium (2007). Nature 447, 799-816.
Gaujoux, R., and Seoighe, C. (2010). BMC bioinformatics 11, 367.
Geiss-Friedlander and Melchior, F (2007). Nature reviews Molecular cell biology 8, 947-956.
Gentleman, R. C., et al. (2004). Genome Biol 5, R80.
Goss, P. E., et al. (2011). NEJM 364, 2381-2391.
Graham, J. D., et al. (2009). Endocrinology 150, 3318-3326.
Hagan, C. R., et al. (2011). Mol Cell Biol 31, 2439-2452.
Hager, G. L., et al. (2009). Molecular cell 35, 741-753.
Halford, S. E., and Marko, J. F. (2004). Nucleic Acids Res 32, 3040-3052.
He, H. H., et al. (2010). Nat Genet. 42, 343-347.
Heintzman, N. D., et al. (2007). Nat Genet 39, 311-318.
Holmstrom, S. R., et al. (2008). Mol Endocrinol.
Horwitz, K. B., et al. (1982). Cell 28, 633-642.
Huang, E., et al. (2003). Nat Genet 34, 226-230.
Hurtado, A., et al. (2011). Nat Genet 43, 27-33.
Iniguez-Lluhi, J. A., and Pearce, D. (2000). Mol Cell Biol 20, 6040-6050.
Irizarry, R. A., et al. (2003). Nucleic Acids Res 31, e15.
Jacobsen, B. M., et al. (2005). Mol Endocrinol 19, 574-587.
Johnston, S., et al. (2009). J Clin Oncol 27, 5538-5546.
Kaufman, B., et al. (2009). J Clin Oncol 27, 5529-5537.
Labriola, L., et al. (2003). Mol Cell Biol 23, 1095-1111.
LaCroix, A. Z., et al. (2011). JAMA 305, 1305-1314.
Lambert, J. R., and Nordeen, S. K. (2003). Mol Endocrinol 17, 1085-1094.
Lange, C. A. (2008). Steroids 73, 914-921.
Lange, C. A., et al. (2000). Proc Natl Acad Sci USA 97, 1032-1037.
Lanigan, F., et al. (2010). Breast Cancer Res 12, R59.
Lenferink, A. E., et al. (2001). Cancer Res 61, 6583-6591.
Li, X., et al. (2003). Mol Cell Biol 23, 3763-3773.
Liang, Y., et al. (2007). Cancer Res 67, 9929-9936.
Liu, S., et al. (2010). Breast Cancer Res Treat 119, 53-61.
Liu, W. M. (2004). Curr Med Chem 11, 2143-2151.
Locke, J. A., et al. (2008). Cancer Res 68, 6407-6415.
Loi, S., et al. (2007). J Clin Oncol 25, 1239-1246.
Lupien, M., et al. (2008). Cell 132, 958-970.
Man, J.-H., et al. (2006). Nucleic Acids Res 34, 5552-5566.
Meijsing, S. H., et al. (2009). Science 324, 407-410.
Melchior, F (2000). Annu Rev Cell Dev Biol 16, 591-626.
Million Women Study Collaborators (2003). Lancet 362, 419-427.
Mo, R., et al. (2006). J Biol Chem 281, 15714-15720.
Moore, M. R., et al. (2000). Biochem Biophys Res Commun 277, 650-654.
Mootha, V. K., et al. (2003). Nat Genet 34, 267-273.
Musgrove, E. A., and Sutherland, R. L. (2009). Nat Rev Cancer 9, 631-643.
Nicholson, D. W., et al. (1995). Nature 376, 37-43.
Ogryzko, V. V., et al. (1996). Cell 87, 953-959.
Oliveros, J. C. (2007). bioinfogp.cnb.csic.es/tools/venny/index.html.
Ong, C. T., and Corces, V. G. (2011). Nat Rev Genet 12, 283-293.
Paik, S., et al. (2004). NEJM 351, 2817-2826.
Parker, J. S., et al. (2009). J Clin Oncol 27, 1160-1167.
Perou, C. M., et al. (2000). Nature 406, 747-752.
Perrault, D., et al. (1996). J Clin Oncol, 14, 2709-12.
Pooley, K. A., et al. (2006). Cancer Epidemiol Biomarkers Prey 15, 675-682.
Prat, A., and Perou, C. M. (2011). Molecular oncology 5, 5-23.
Reginato, M. J., et al. (2005). Mol Cell Biol 25, 4591-4601.
Rhodes, D. R., et al. (2007). Neoplasia 9, 166-180.
Richer, J. K., et al. (2002). J Biol Chem 277, 5209-5218.
Salatino, M., et al. (2004). Oncogene 23, 5161-5174.
Sartorius, C. A., et al. (1994). Cancer Res 54, 3868-3877.
Satoh et al. (2004). Journal of mammary gland biology and neoplasia 9, 195-205.
Satoh, K., et al. (2007). Oncogene 26, 7526-7534.
Satokata, I., et al. (2000). Nat Genet 24, 391-395.
Siegel, R., et al. (2012). CA Cancer J Clin 62, 10-29.
Smalley, M. J., et al. (2007). Breast Cancer Res 9, R85.
Sørlie, T., et al. (2001). Proc Natl Acad Sci USA 98, 10869-10874.
Su, B., et al. (2011). J Steroid Biochem Mol Biol 123, 101-108.

Subramanian, A., et al. (2005). Proc Natl Acad Sci USA 102, 15545-15550.
Suzuki, T., et al. (2005). Endocr Relat Cancer 12, 701-720.
Takahashi, C., et al. (1997). Leukemia 11 Suppl 3, 340-343.
Takimoto, G S., et al. (1996). J Biol Chem 271, 13308-13316.
Tang, Q., et al. (2011). Cancer Res.
Terry, K. L., et al. (2005). American journal of epidemiology 161, 442-451.
van't Veer, L. J., et al. (2002). Nature 415, 530-536.
Verzi, M. P., et al. (2010). Dev Cell 19, 713-726.
Vicent, G P., et al. (2011). Genes Dev 25, 845-862.

All publications, nucleotide and amino acid sequence identified by their accession nos., patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and the methods and processes are not necessarily restricted to the orders of steps indicated herein or in the claims. As used herein and in the appended claims, the singular forms "a," "an," and "the" include plural reference unless the context clearly dictates otherwise. Thus, for example, a reference to "a nucleic acid" or "a polypeptide" includes a plurality of such nucleic acids or polypeptides (for example, a solution of nucleic acids or polypeptides or a series of nucleic acid or polypeptide preparations), and so forth. In this document, the term "or" is used to refer to a nonexclusive or, such that "A or B" includes "A but not B," "B but not A," and "A and B," unless otherwise indicated.

Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims and statements of the invention.

What is claimed is:

1. A method of treating breast, ovarian, endometrial or uterine cancer in a patient, said method comprising:
   a) obtaining a breast, ovarian, endometrial or uterine cancer sample from said patient;
   b) detecting whether expression of THY1, KLF9, SPINK5L3, PHLDA1, MAP1A, SPRYD5, ATG12, PDK4, MSX2, TUBA3E, TSC22D1, TUBA3D, KHDRBS3, UTS2D, SLC35C1 and KIAA0513 is increased in said cancer sample as compared to a control;
   c) diagnosing said patient with breast, ovarian, endometrial or uterine cancer amenable to treatment with an anti-progestin, alone or in combination with other treatment when the expression of THY1, KLF9, SPINK5L3, PHLDA1, MAP1A, SPRYD5, ATG12, PDK4, MSX2, TUBA3E, TSC22D1, TUBA3D, KHDRBS3, UTS2D, SLC35C1 and KIAA0513 is increased in said cancer sample as compared to a control; and
   d) administering an effective amount of an anti-progestin to said patient with increased expression of THYL1, KLF9, SPINK5L3, PHLDA1, MAP1A, SPRYD5, ATG12, PDK4, MSX2, TUBA3E, TSC22D1, TUBA3D, KHDRBS3, UTS2D, SLC35C1 and KIAA0513.

2. A method of treating breast, ovarian, endometrial or uterine cancer in a patient, said method comprising:
   a) obtaining a breast, ovarian, endometrial or uterine cancer sample from said patient;
   b) detecting whether expression of THY1, KLF9, SPINK5L3, PHLDA1, MAP1A, SPRYD5, ATG12, PDK4, MSX2, TUBA3E, TSC22D1, TUBA3D, KHDRBS3, UTS2D, SLC35C1 and KIAA0513 is increased in said cancer sample as compared to a control, wherein detection of increased expression is carried out with the use of radiolabeled probes for THY1, KLF9, SPINK5L3, PHLDA1,MAP1A, SPRYD5, ATG12, PDK4, MSX2, TUBA3E, TSC22D1, TUBA3D, KHDRBS3, UTS2D, SLC35C1 and KIAA0513, wherein said probes comprise SEQ ID NOs: 16-31;
   c) diagnosing said patient with breast, ovarian, endometrial or uterine cancer amenable to treatment with an anti-progestin, alone or in combination with other treatment when the expression of THY1, KLF9, SPINK5L3, PHLDA1, MAP1A, SPRYD5, ATG12, PDK4, MSX2, TUBA3E, TSC22D1, TUBA3D, KHDRBS3, UTS2D, SLC35C1 and KIAA0513 is increased in said cancer sample as compared to a control; and
   d) administering an effective amount of an anti-progestin- to said patient with increased expression of THY1, KLF9, SPINK5L3, PHLDA1, MAP1A, SPRYD5, ATG12, PDK4, MSX2, TUBA3E, TSC22D1, TUBA3D, KHDRBS3, UTS2D, SLC35C1 and KIAA0513.

* * * * *

UNITED STATES PATENT AND TRADEMARK OFFICE
CERTIFICATE OF CORRECTION

PATENT NO.        : 10,501,800 B2
APPLICATION NO.   : 13/843482
DATED             : December 10, 2019
INVENTOR(S)       : Lange et al.

Page 1 of 2

It is certified that error appears in the above-identified patent and that said Letters Patent is hereby corrected as shown below:

On the Title Page

In Column 2, Item (56) under "Other Publications", Lines 7-8, delete "Mar. 12, 2013"," and insert --Aug. 12, 2013",-- therefor Page 2, in Column 1, Item (56) under "Other Publications", Line 26, delete "Subsetof" and insert --Subset of-- therefor Page 2, in Column 1, Item (56) under "Other Publications", Line 57, delete "andpromoter" and insert --and promoter-- therefor Page 2, in Column 2, Item (56) under "Other Publications", Line 69, delete "201515"," and insert --2015",-- therefor Page 3, in Column 1, Item (56) under "Other Publications", Line 5, delete "13714144.6,Response" and insert --13714144.6, Response-- therefor In the Specification In Column 1, Lines 12-15, delete "This invention was made with the assistance of government support under United States Grant No. CA1159712-01 from the National Institutes of Health. The government has certain rights in the invention." and insert --This invention was made with government support under CA159712 awarded by the National Institutes of Health. The government has certain rights in the invention.
This invention was made with government support under W81XWH-10-1-0274 awarded by US Department of Defense/ARMY. The government has certain rights in the invention.-- therefor In the Claims Column 97, Line 49, in Claim 1, delete "THYL1," and insert --THY1,-- therefor Signed and Sealed this
Twelfth Day of May, 2020

Andrei Iancu
*Director of the United States Patent and Trademark Office*

Column 98, Line 35, in Claim 2, delete "PHLDA1,MAP1A," and insert --PHLDA1, MAP1A,-- therefor Column 98, Lines 49-50, in Claim 2, delete "anti-progestin-to" and insert --anti-progestin to-- therefor

SEQUENCE LISTING

```
<160> NUMBER OF SEQ ID NOS: 122

<210> SEQ ID NO 1
<211> LENGTH: 50
<212> TYPE: DNA
<213> ORGANISM: Artificial Sequence
<220> FEATURE:
<223> OTHER INFORMATION: A synthetic oligonucleotide probe

<400> SEQUENCE: 1
ggtaaactac acctgttgaa ggccaagttc agggcagctg ttgtgatctg            50

<210> SEQ ID NO 2
<211> LENGTH: 50
<212> TYPE: DNA
<213> ORGANISM: Artificial Sequence
<220> FEATURE:
<223> OTHER INFORMATION: A synthetic oligonucleotide probe

<400> SEQUENCE: 2
gaaccactga gtcaggagag ccaggtggag gaaccaccga gtcaggagag            50

<210> SEQ ID NO 3
<211> LENGTH: 50
<212> TYPE: DNA
<213> ORGANISM: Artificial Sequence
```

```
<220> FEATURE:
<223> OTHER INFORMATION: A synthetic oligonucleotide probe

<400> SEQUENCE: 3
ggccatttca gacttgggag atgaggcggc tgttgtcatt gctgatcctg          50

<210> SEQ ID NO 4
<211> LENGTH: 50
<212> TYPE: DNA
<213> ORGANISM: Artificial Sequence
<220> FEATURE:
<223> OTHER INFORMATION: A synthetic oligonucleotide probe

<400> SEQUENCE: 4
ccattggcac agggaggttt gacctcttcc ctgctattat ccctcctccc          50

<210> SEQ ID NO 5
<211> LENGTH: 50
<212> TYPE: DNA
<213> ORGANISM: Artificial Sequence
<220> FEATURE:
<223> OTHER INFORMATION: A synthetic oligonucleotide probe

<400> SEQUENCE: 5
gtgtaatcac ccaaaacccc ccggcctgtg cctgttttcc cttctgcgct          50

<210> SEQ ID NO 6
<211> LENGTH: 50
<212> TYPE: DNA
<213> ORGANISM: Artificial Sequence
<220> FEATURE:
<223> OTHER INFORMATION: A synthetic oligonucleotide probe

<400> SEQUENCE: 6
agcaggtctt accgagaatt cagctgccaa aaccctcctc tgagtgttcc          50

<210> SEQ ID NO 7
<211> LENGTH: 50
<212> TYPE: DNA
<213> ORGANISM: Artificial Sequence
<220> FEATURE:
<223> OTHER INFORMATION: A synthetic oligonucleotide probe

<400> SEQUENCE: 7
gggtcacgtg tctttggtga gtgagaagac ctaaactcct ggccatcatc          50

<210> SEQ ID NO 8
<211> LENGTH: 50
<212> TYPE: DNA
<213> ORGANISM: Artificial Sequence
<220> FEATURE:
<223> OTHER INFORMATION: A synthetic oligonucleotide probe

<400> SEQUENCE: 8
acgcattcct ggcggccttc ctcgggggta tcctggtgtt tggagaaaac          50

<210> SEQ ID NO 9
<211> LENGTH: 50
<212> TYPE: DNA
<213> ORGANISM: Artificial Sequence
<220> FEATURE:
<223> OTHER INFORMATION: A synthetic oligonucleotide probe

<400> SEQUENCE: 9
accagcagaa gccagcagag aggcatggga caggttcccc acaagcctta          50
```

```
<210> SEQ ID NO 10
<211> LENGTH: 50
<212> TYPE: DNA
<213> ORGANISM: Artificial Sequence
<220> FEATURE:
<223> OTHER INFORMATION: A synthetic oligonucleotide probe

<400> SEQUENCE: 10
ctgaggcaag ccatggagtg agacccagga gccggacact tctcaggaaa          50

<210> SEQ ID NO 11
<211> LENGTH: 50
<212> TYPE: DNA
<213> ORGANISM: Artificial Sequence
<220> FEATURE:
<223> OTHER INFORMATION: A synthetic oligonucleotide probe

<400> SEQUENCE: 11
tctcacccag gcacagcccc gccaccatgg atctccgtgt acactatcaa          50

<210> SEQ ID NO 12
<211> LENGTH: 50
<212> TYPE: DNA
<213> ORGANISM: Artificial Sequence
<220> FEATURE:
<223> OTHER INFORMATION: A synthetic oligonucleotide probe

<400> SEQUENCE: 12
tgtcaagggg ctttgcattc aaactgcttt tccagggcta tactcagaag          50

<210> SEQ ID NO 13
<211> LENGTH: 50
<212> TYPE: DNA
<213> ORGANISM: Artificial Sequence
<220> FEATURE:
<223> OTHER INFORMATION: A synthetic oligonucleotide probe

<400> SEQUENCE: 13
tggggtgctt cctgtggtag tgtctttcag gtatccgttc cactagctac          50

<210> SEQ ID NO 14
<211> LENGTH: 50
<212> TYPE: DNA
<213> ORGANISM: Artificial Sequence
<220> FEATURE:
<223> OTHER INFORMATION: A synthetic oligonucleotide probe

<400> SEQUENCE: 14
agcaacctca caaacaagcc gcttctgtta ggtacatgtc ctgcccttgc          50

<210> SEQ ID NO 15
<211> LENGTH: 50
<212> TYPE: DNA
<213> ORGANISM: Artificial Sequence
<220> FEATURE:
<223> OTHER INFORMATION: A synthetic oligonucleotide probe

<400> SEQUENCE: 15
ctcacccctt aatgttcacc tgcaaactca taccagagag aaagccctca          50

<210> SEQ ID NO 16
<211> LENGTH: 50
<212> TYPE: DNA
<213> ORGANISM: Artificial Sequence
<220> FEATURE:
<223> OTHER INFORMATION: A synthetic oligonucleotide probe
```

<400> SEQUENCE: 16
ctgaggcaag ccatggagtg agacccagga gccggacact tctcaggaaa          50

<210> SEQ ID NO 17
<211> LENGTH: 50
<212> TYPE: DNA
<213> ORGANISM: Artificial Sequence
<220> FEATURE:
<223> OTHER INFORMATION: A synthetic oligonucleotide probe

<400> SEQUENCE: 17
gcccttcacc attgtggaat gatgccctgg ctttaaggtt tagctccaca          50

<210> SEQ ID NO 18
<211> LENGTH: 50
<212> TYPE: DNA
<213> ORGANISM: Artificial Sequence
<220> FEATURE:
<223> OTHER INFORMATION: A synthetic oligonucleotide probe

<400> SEQUENCE: 18
gcagactgcc ccaatgtgac agcacctgtt tgtgcctcaa atggccacac          50

<210> SEQ ID NO 19
<211> LENGTH: 50
<212> TYPE: DNA
<213> ORGANISM: Artificial Sequence
<220> FEATURE:
<223> OTHER INFORMATION: A synthetic oligonucleotide probe

<400> SEQUENCE: 19
aacagtctct ccgccccgca ccagatcaag tagtttggac atcaccctac          50

<210> SEQ ID NO 20
<211> LENGTH: 50
<212> TYPE: DNA
<213> ORGANISM: Artificial Sequence
<220> FEATURE:
<223> OTHER INFORMATION: A synthetic oligonucleotide probe

<400> SEQUENCE: 20
cccaagcaag ccagtgagca gccctgccag actactgcca gactgagaaa          50

<210> SEQ ID NO 21
<211> LENGTH: 50
<212> TYPE: DNA
<213> ORGANISM: Artificial Sequence
<220> FEATURE:
<223> OTHER INFORMATION: A synthetic oligonucleotide probe

<400> SEQUENCE: 21
tccctgatat acaccatccc caattgctcc ttctcacctc ctctcaggcc          50

<210> SEQ ID NO 22
<211> LENGTH: 50
<212> TYPE: DNA
<213> ORGANISM: Artificial Sequence
<220> FEATURE:
<223> OTHER INFORMATION: A synthetic oligonucleotide probe

<400> SEQUENCE: 22
gagtcgtgat tgtaccactg cattcctgct gagcaacaga gtgagacccc          50

```
<210> SEQ ID NO 23
<211> LENGTH: 50
<212> TYPE: DNA
<213> ORGANISM: Artificial Sequence
<220> FEATURE:
<223> OTHER INFORMATION: A synthetic oligonucleotide probe

<400> SEQUENCE: 23
cagaagtcct agacagtgac atttcttaat ggtgggagtc cagctcatgc            50

<210> SEQ ID NO 24
<211> LENGTH: 50
<212> TYPE: DNA
<213> ORGANISM: Artificial Sequence
<220> FEATURE:
<223> OTHER INFORMATION: A synthetic oligonucleotide probe

<400> SEQUENCE: 24
aggtacattc atcctcacag attgcaaagg tgatttgggt ggggtttag             50

<210> SEQ ID NO 25
<211> LENGTH: 50
<212> TYPE: DNA
<213> ORGANISM: Artificial Sequence
<220> FEATURE:
<223> OTHER INFORMATION: A synthetic oligonucleotide probe

<400> SEQUENCE: 25
ggtccccaaa gacgtcaatg cggccatcgc caccatcaag accaagcgca            50

<210> SEQ ID NO 26
<211> LENGTH: 50
<212> TYPE: DNA
<213> ORGANISM: Artificial Sequence
<220> FEATURE:
<223> OTHER INFORMATION: A synthetic oligonucleotide probe

<400> SEQUENCE: 26
tcccaatggt gtagaccagt ggcgatggat ctaggagttt accaactgag            50

<210> SEQ ID NO 27
<211> LENGTH: 50
<212> TYPE: DNA
<213> ORGANISM: Artificial Sequence
<220> FEATURE:
<223> OTHER INFORMATION: A synthetic oligonucleotide probe

<400> SEQUENCE: 27
tcccctgcca cccccgggat ggctgcttcc aagttgtttg caattaaagg            50

<210> SEQ ID NO 28
<211> LENGTH: 50
<212> TYPE: DNA
<213> ORGANISM: Artificial Sequence
<220> FEATURE:
<223> OTHER INFORMATION: A synthetic oligonucleotide probe

<400> SEQUENCE: 28
aggcaccttc agcgaggaca gcaaagggcg tctacagaga ccagccatat            50

<210> SEQ ID NO 29
<211> LENGTH: 50
<212> TYPE: DNA
<213> ORGANISM: Artificial Sequence
<220> FEATURE:
<223> OTHER INFORMATION: A synthetic oligonucleotide probe
```

```
<400> SEQUENCE: 29
gctggtatat ccagtgcatt gttggcacca tgggaccaga aggtggtgac            50

<210> SEQ ID NO 30
<211> LENGTH: 50
<212> TYPE: DNA
<213> ORGANISM: Artificial Sequence
<220> FEATURE:
<223> OTHER INFORMATION: A synthetic oligonucleotide probe

<400> SEQUENCE: 30
agggtggctt gcagtccctg gcccttctgg tgggcatttg gtatgtcctt            50

<210> SEQ ID NO 31
<211> LENGTH: 50
<212> TYPE: DNA
<213> ORGANISM: Artificial Sequence
<220> FEATURE:
<223> OTHER INFORMATION: A synthetic oligonucleotide probe

<400> SEQUENCE: 31
cttcttgaac ctggtggccc ccgttggaac tatcagtggc gtctcccatg            50

<210> SEQ ID NO 32
<211> LENGTH: 50
<212> TYPE: DNA
<213> ORGANISM: Artificial Sequence
<220> FEATURE:
<223> OTHER INFORMATION: A synthetic oligonucleotide probe

<400> SEQUENCE: 32
agcaacctca caaacaagcc gcttctgtta ggtacatgtc ctgcccttgc            50

<210> SEQ ID NO 33
<211> LENGTH: 50
<212> TYPE: DNA
<213> ORGANISM: Artificial Sequence
<220> FEATURE:
<223> OTHER INFORMATION: A synthetic oligonucleotide probe

<400> SEQUENCE: 33
gccaggtgtc ctgactgtcc tacaatatca ttttcctggg agtgggagtc            50

<210> SEQ ID NO 34
<211> LENGTH: 50
<212> TYPE: DNA
<213> ORGANISM: Artificial Sequence
<220> FEATURE:
<223> OTHER INFORMATION: A synthetic oligonucleotide probe

<400> SEQUENCE: 34
ggtaaactac acctgttgaa ggccaagttc agggcagctg ttgtgatctg            50

<210> SEQ ID NO 35
<211> LENGTH: 50
<212> TYPE: DNA
<213> ORGANISM: Artificial Sequence
<220> FEATURE:
<223> OTHER INFORMATION: A synthetic oligonucleotide probe

<400> SEQUENCE: 35
ggagctcaag tgtcgggaac tgtctaactt caggttgtgt gagtgcgtta            50
```

```
<210> SEQ ID NO 36
<211> LENGTH: 50
<212> TYPE: DNA
<213> ORGANISM: Artificial Sequence
<220> FEATURE:
<223> OTHER INFORMATION: A synthetic oligonucleotide probe

<400> SEQUENCE: 36
atcactattc ctggttatct caccaacgaa ggctaggagg cggcgtcaga        50

<210> SEQ ID NO 37
<211> LENGTH: 50
<212> TYPE: DNA
<213> ORGANISM: Artificial Sequence
<220> FEATURE:
<223> OTHER INFORMATION: A synthetic oligonucleotide probe

<400> SEQUENCE: 37
ggtggaggaa ccactgagtc aggagagcga gatggaagaa ccactgagtc        50

<210> SEQ ID NO 38
<211> LENGTH: 50
<212> TYPE: DNA
<213> ORGANISM: Artificial Sequence
<220> FEATURE:
<223> OTHER INFORMATION: A synthetic oligonucleotide probe

<400> SEQUENCE: 38 cccccaaaa ttatcagtgc tctgctttta gtcacgtgta ttttcattac         50

<210> SEQ ID NO 39
<211> LENGTH: 50
<212> TYPE: DNA
<213> ORGANISM: Artificial Sequence
<220> FEATURE:
<223> OTHER INFORMATION: A synthetic oligonucleotide probe

<400> SEQUENCE: 39
ccacatcgtc ttccctgtcc caatcgacca gtgtatcgac ggctgagtgc        50

<210> SEQ ID NO 40
<211> LENGTH: 50
<212> TYPE: DNA
<213> ORGANISM: Artificial Sequence
<220> FEATURE:
<223> OTHER INFORMATION: A synthetic oligonucleotide probe

<400> SEQUENCE: 40
cggcgcttcc cagcaccaac atgtaaccgg catgtttcca gcagaagaca        50

<210> SEQ ID NO 41
<211> LENGTH: 50
<212> TYPE: DNA
<213> ORGANISM: Artificial Sequence
<220> FEATURE:
<223> OTHER INFORMATION: A synthetic oligonucleotide probe

<400> SEQUENCE: 41
agcaacctca caaacaagcc gcttctgtta ggtacatgtc ctgcccttgc        50

<210> SEQ ID NO 42
<211> LENGTH: 50
<212> TYPE: DNA
<213> ORGANISM: Artificial Sequence
<220> FEATURE:
<223> OTHER INFORMATION: A synthetic oligonucleotide probe
```

<400> SEQUENCE: 42
cgatgttcag aggctgtttc ctgcagcatg tatttccatg gcccacacag        50

<210> SEQ ID NO 43
<211> LENGTH: 50
<212> TYPE: DNA
<213> ORGANISM: Artificial Sequence
<220> FEATURE:
<223> OTHER INFORMATION: A synthetic oligonucleotide probe

<400> SEQUENCE: 43
gacacagaac acagacgcct tactggcaac ctgctttcaa gacccctgtc        50

<210> SEQ ID NO 44
<211> LENGTH: 50
<212> TYPE: DNA
<213> ORGANISM: Artificial Sequence
<220> FEATURE:
<223> OTHER INFORMATION: A synthetic oligonucleotide probe

<400> SEQUENCE: 44
gtgtttatga tgagtcagag tgcttttcct cggtgggaca gttgctggcc        50

<210> SEQ ID NO 45
<211> LENGTH: 50
<212> TYPE: DNA
<213> ORGANISM: Artificial Sequence
<220> FEATURE:
<223> OTHER INFORMATION: A synthetic oligonucleotide probe

<400> SEQUENCE: 45
cagttctgca gtgtaatgga ggacgggcaa cgtgcatgtg caggctcacc        50

<210> SEQ ID NO 46
<211> LENGTH: 50
<212> TYPE: DNA
<213> ORGANISM: Artificial Sequence
<220> FEATURE:
<223> OTHER INFORMATION: A synthetic oligonucleotide probe

<400> SEQUENCE: 46
gagccaaagg ctcactcaaa ggcacaggta gatgcctggc agcaaattca        50

<210> SEQ ID NO 47
<211> LENGTH: 50
<212> TYPE: DNA
<213> ORGANISM: Artificial Sequence
<220> FEATURE:
<223> OTHER INFORMATION: A synthetic oligonucleotide probe

<400> SEQUENCE: 47
agcaacctca caaacaagcc gcttctgtta ggtacatgtc ctgcccttgc        50

<210> SEQ ID NO 48
<211> LENGTH: 50
<212> TYPE: DNA
<213> ORGANISM: Artificial Sequence
<220> FEATURE:
<223> OTHER INFORMATION: A synthetic oligonucleotide probe

<400> SEQUENCE: 48
tatagacctg tgtgaccagc ccccagttcc tcccccagtt cctcccagga        50

```
<210> SEQ ID NO 49
<211> LENGTH: 50
<212> TYPE: DNA
<213> ORGANISM: Artificial Sequence
<220> FEATURE:
<223> OTHER INFORMATION: A synthetic oligonucleotide probe

<400> SEQUENCE: 49
tctggtctac agtggaggga gagctggttt taaatgttgg ccgttgatgc          50

<210> SEQ ID NO 50
<211> LENGTH: 50
<212> TYPE: DNA
<213> ORGANISM: Artificial Sequence
<220> FEATURE:
<223> OTHER INFORMATION: A synthetic oligonucleotide probe

<400> SEQUENCE: 50
gatggaacca actttgtaca tcttggccat gtcactggtc attgtgtgaa          50

<210> SEQ ID NO 51
<211> LENGTH: 50
<212> TYPE: DNA
<213> ORGANISM: Artificial Sequence
<220> FEATURE:
<223> OTHER INFORMATION: A synthetic oligonucleotide probe

<400> SEQUENCE: 51
cgactggcag accgactact tgccctggtc atccaccctg aggaagatgt          50

<210> SEQ ID NO 52
<211> LENGTH: 50
<212> TYPE: DNA
<213> ORGANISM: Artificial Sequence
<220> FEATURE:
<223> OTHER INFORMATION: A synthetic oligonucleotide probe

<400> SEQUENCE: 52
ctagggttcc ctcccagtct tcacatcact ctggcctcat caccaaggtg          50

<210> SEQ ID NO 53
<211> LENGTH: 22
<212> TYPE: DNA
<213> ORGANISM: Artificial Sequence
<220> FEATURE:
<223> OTHER INFORMATION: A synthetic oligonucleotide primer

<400> SEQUENCE: 53
ctgtctttca tccttcccag ag                                        22

<210> SEQ ID NO 54
<211> LENGTH: 25
<212> TYPE: DNA
<213> ORGANISM: Artificial Sequence
<220> FEATURE:
<223> OTHER INFORMATION: A synthetic oligonucleotide primer

<400> SEQUENCE: 54
tctttctgct tcttctccag tttag                                     25

<210> SEQ ID NO 55
<211> LENGTH: 25
<212> TYPE: DNA
<213> ORGANISM: Artificial Sequence
<220> FEATURE:
<223> OTHER INFORMATION: A synthetic oligonucleotide primer
```

```
<400> SEQUENCE: 55
ggcttatttc agatttgaag acctc                                          25

<210> SEQ ID NO 56
<211> LENGTH: 24
<212> TYPE: DNA
<213> ORGANISM: Artificial Sequence
<220> FEATURE:
<223> OTHER INFORMATION: A synthetic oligonucleotide primer

<400> SEQUENCE: 56
agaagcgcaa tactaggacc tttc                                           24

<210> SEQ ID NO 57
<211> LENGTH: 21
<212> TYPE: DNA
<213> ORGANISM: Artificial Sequence
<220> FEATURE:
<223> OTHER INFORMATION: A synthetic oligonucleotide primer

<400> SEQUENCE: 57
tgctcaacaa tgtcgattct g                                              21

<210> SEQ ID NO 58
<211> LENGTH: 20
<212> TYPE: DNA
<213> ORGANISM: Artificial Sequence
<220> FEATURE:
<223> OTHER INFORMATION: A synthetic oligonucleotide primer

<400> SEQUENCE: 58
ttccactccc attctgcttc                                                20

<210> SEQ ID NO 59
<211> LENGTH: 23
<212> TYPE: DNA
<213> ORGANISM: Artificial Sequence
<220> FEATURE:
<223> OTHER INFORMATION: A synthetic oligonucleotide primer

<400> SEQUENCE: 59
gtctgactct gactctcgga ctg                                            23

<210> SEQ ID NO 60
<211> LENGTH: 25
<212> TYPE: DNA
<213> ORGANISM: Artificial Sequence
<220> FEATURE:
<223> OTHER INFORMATION: A synthetic oligonucleotide primer

<400> SEQUENCE: 60
gaacttacat cagaaggttg ctttg                                          25

<210> SEQ ID NO 61
<211> LENGTH: 22
<212> TYPE: DNA
<213> ORGANISM: Artificial Sequence
<220> FEATURE:
<223> OTHER INFORMATION: A synthetic oligonucleotide primer

<400> SEQUENCE: 61
accagcctcc tatatggaaa tc                                             22
```

```
<210> SEQ ID NO 62
<211> LENGTH: 20
<212> TYPE: DNA
<213> ORGANISM: Artificial Sequence
<220> FEATURE:
<223> OTHER INFORMATION: A synthetic oligonucleotide primer

<400> SEQUENCE: 62
ctcccgagga caaatgattc                                                   20

<210> SEQ ID NO 63
<211> LENGTH: 24
<212> TYPE: DNA
<213> ORGANISM: Artificial Sequence
<220> FEATURE:
<223> OTHER INFORMATION: A synthetic oligonucleotide primer

<400> SEQUENCE: 63
agaagaagca caatgaggag attc                                              24

<210> SEQ ID NO 64
<211> LENGTH: 25
<212> TYPE: DNA
<213> ORGANISM: Artificial Sequence
<220> FEATURE:
<223> OTHER INFORMATION: A synthetic oligonucleotide primer

<400> SEQUENCE: 64
catgtggaaa ttatcacttc tttgg                                             25

<210> SEQ ID NO 65
<211> LENGTH: 24
<212> TYPE: DNA
<213> ORGANISM: Artificial Sequence
<220> FEATURE:
<223> OTHER INFORMATION: A synthetic oligonucleotide primer

<400> SEQUENCE: 65
gccaaaaggg tcatcatctc tgcc                                              24

<210> SEQ ID NO 66
<211> LENGTH: 20
<212> TYPE: DNA
<213> ORGANISM: Artificial Sequence
<220> FEATURE:
<223> OTHER INFORMATION: A synthetic oligonucleotide primer

<400> SEQUENCE: 66
tggtggtgca ggaggcattg                                                   20

<210> SEQ ID NO 67
<211> LENGTH: 20
<212> TYPE: DNA
<213> ORGANISM: Artificial Sequence
<220> FEATURE:
<223> OTHER INFORMATION: A synthetic oligonucleotide primer

<400> SEQUENCE: 67
tgctggatgc cctgctggag                                                   20

<210> SEQ ID NO 68
<211> LENGTH: 21
<212> TYPE: DNA
<213> ORGANISM: Artificial Sequence
<220> FEATURE:
<223> OTHER INFORMATION: A synthetic oligonucleotide primer
```

```
<400> SEQUENCE: 68
accactcacg agtcacctcc g                                              21

<210> SEQ ID NO 69
<211> LENGTH: 24
<212> TYPE: DNA
<213> ORGANISM: Artificial Sequence
<220> FEATURE:
<223> OTHER INFORMATION: A synthetic oligonucleotide primer

<400> SEQUENCE: 69
aaatcccttg ttaaaggagg tctg                                           24

<210> SEQ ID NO 70
<211> LENGTH: 25
<212> TYPE: DNA
<213> ORGANISM: Artificial Sequence
<220> FEATURE:
<223> OTHER INFORMATION: A synthetic oligonucleotide primer

<400> SEQUENCE: 70
ctgagaggta ccataatgga aaatg                                          25

<210> SEQ ID NO 71
<211> LENGTH: 20
<212> TYPE: DNA
<213> ORGANISM: Artificial Sequence
<220> FEATURE:
<223> OTHER INFORMATION: A synthetic oligonucleotide primer

<400> SEQUENCE: 71
agcggcgtgg atgcaggaac                                                20

<210> SEQ ID NO 72
<211> LENGTH: 20
<212> TYPE: DNA
<213> ORGANISM: Artificial Sequence
<220> FEATURE:
<223> OTHER INFORMATION: A synthetic oligonucleotide primer

<400> SEQUENCE: 72
tgcgcggctt ccgattggtc                                                20

<210> SEQ ID NO 73
<211> LENGTH: 20
<212> TYPE: DNA
<213> ORGANISM: Artificial Sequence
<220> FEATURE:
<223> OTHER INFORMATION: A synthetic oligonucleotide primer

<400> SEQUENCE: 73
catactccac tgcaccaacg                                                20

<210> SEQ ID NO 74
<211> LENGTH: 20
<212> TYPE: DNA
<213> ORGANISM: Artificial Sequence
<220> FEATURE:
<223> OTHER INFORMATION: A synthetic oligonucleotide primer

<400> SEQUENCE: 74
agaaattggc aagccgtaac                                                20
```

<210> SEQ ID NO 75
<211> LENGTH: 22
<212> TYPE: DNA
<213> ORGANISM: Artificial Sequence
<220> FEATURE:
<223> OTHER INFORMATION: A synthetic oligonucleotide primer

<400> SEQUENCE: 75
tctcatcagc tacaccacca ac                                              22

<210> SEQ ID NO 76
<211> LENGTH: 24
<212> TYPE: DNA
<213> ORGANISM: Artificial Sequence
<220> FEATURE:
<223> OTHER INFORMATION: A synthetic oligonucleotide primer

<400> SEQUENCE: 76
acattggctg aatagttgtc aaac                                            24

<210> SEQ ID NO 77
<211> LENGTH: 20
<212> TYPE: DNA
<213> ORGANISM: Artificial Sequence
<220> FEATURE:
<223> OTHER INFORMATION: A synthetic oligonucleotide primer

<400> SEQUENCE: 77
agctgtcctc aaaagcaagg                                                 20

<210> SEQ ID NO 78
<211> LENGTH: 20
<212> TYPE: DNA
<213> ORGANISM: Artificial Sequence
<220> FEATURE:
<223> OTHER INFORMATION: A synthetic oligonucleotide primer

<400> SEQUENCE: 78
tctgggcaat cagagttttg                                                 20

<210> SEQ ID NO 79
<211> LENGTH: 20
<212> TYPE: DNA
<213> ORGANISM: Artificial Sequence
<220> FEATURE:
<223> OTHER INFORMATION: A synthetic oligonucleotide primer

<400> SEQUENCE: 79
ccgatgatca agatgtggag                                                 20

<210> SEQ ID NO 80
<211> LENGTH: 20
<212> TYPE: DNA
<213> ORGANISM: Artificial Sequence
<220> FEATURE:
<223> OTHER INFORMATION: A synthetic oligonucleotide primer

<400> SEQUENCE: 80
caaaggcatt gatgaaggtg                                                 20

<210> SEQ ID NO 81
<211> LENGTH: 25
<212> TYPE: DNA
<213> ORGANISM: Artificial Sequence
<220> FEATURE:
<223> OTHER INFORMATION: A synthetic oligonucleotide primer

<400> SEQUENCE: 81
ataacaagac ctctgccaga agaac                                      25

<210> SEQ ID NO 82
<211> LENGTH: 22
<212> TYPE: DNA
<213> ORGANISM: Artificial Sequence
<220> FEATURE:
<223> OTHER INFORMATION: A synthetic oligonucleotide primer

<400> SEQUENCE: 82
caggtgggtt cctatgttc ag                                          22

<210> SEQ ID NO 83
<211> LENGTH: 25
<212> TYPE: DNA
<213> ORGANISM: Artificial Sequence
<220> FEATURE:
<223> OTHER INFORMATION: A synthetic oligonucleotide primer

<400> SEQUENCE: 83
agaagatgta gacttcctgc cctac                                      25

<210> SEQ ID NO 84
<211> LENGTH: 25
<212> TYPE: DNA
<213> ORGANISM: Artificial Sequence
<220> FEATURE:
<223> OTHER INFORMATION: A synthetic oligonucleotide primer

<400> SEQUENCE: 84
tttcgtttgg ataaacgtaa ttctg                                      25

<210> SEQ ID NO 85
<211> LENGTH: 20
<212> TYPE: DNA
<213> ORGANISM: Artificial Sequence
<220> FEATURE:
<223> OTHER INFORMATION: A synthetic oligonucleotide primer

<400> SEQUENCE: 85
tccaactcct aagccagtgc                                            20

<210> SEQ ID NO 86
<211> LENGTH: 20
<212> TYPE: DNA
<213> ORGANISM: Artificial Sequence
<220> FEATURE:
<223> OTHER INFORMATION: A synthetic oligonucleotide primer

<400> SEQUENCE: 86
tgctcctggg agtagattgg                                            20

<210> SEQ ID NO 87
<211> LENGTH: 20
<212> TYPE: DNA
<213> ORGANISM: Artificial Sequence
<220> FEATURE:
<223> OTHER INFORMATION: A synthetic oligonucleotide primer

<400> SEQUENCE: 87
gccagccaac tgctatcttc                                            20

```
<210> SEQ ID NO 88
<211> LENGTH: 19
<212> TYPE: DNA
<213> ORGANISM: Artificial Sequence
<220> FEATURE:
<223> OTHER INFORMATION: A synthetic oligonucleotide primer

<400> SEQUENCE: 88
ctgggagtgc tctggaagg                                                19

<210> SEQ ID NO 89
<211> LENGTH: 24
<212> TYPE: DNA
<213> ORGANISM: Artificial Sequence
<220> FEATURE:
<223> OTHER INFORMATION: A synthetic oligonucleotide primer

<400> SEQUENCE: 89
gttccctgag aacctcatta aacc                                           24

<210> SEQ ID NO 90
<211> LENGTH: 20
<212> TYPE: DNA
<213> ORGANISM: Artificial Sequence
<220> FEATURE:
<223> OTHER INFORMATION: A synthetic oligonucleotide primer

<400> SEQUENCE: 90
ggtctctgca gcctgttctg                                                20

<210> SEQ ID NO 91
<211> LENGTH: 24
<212> TYPE: DNA
<213> ORGANISM: Artificial Sequence
<220> FEATURE:
<223> OTHER INFORMATION: A synthetic oligonucleotide primer

<400> SEQUENCE: 91
cacatttctg tctgactctg aagc                                           24

<210> SEQ ID NO 92
<211> LENGTH: 26
<212> TYPE: DNA
<213> ORGANISM: Artificial Sequence
<220> FEATURE:
<223> OTHER INFORMATION: A synthetic oligonucleotide primer

<400> SEQUENCE: 92
ccacatttgc tagcttatta gttctg                                         26

<210> SEQ ID NO 93
<211> LENGTH: 25
<212> TYPE: DNA
<213> ORGANISM: Artificial Sequence
<220> FEATURE:
<223> OTHER INFORMATION: A synthetic oligonucleotide primer

<400> SEQUENCE: 93
gacgtccaga tcagaactaa taagc                                          25

<210> SEQ ID NO 94
<211> LENGTH: 25
<212> TYPE: DNA
<213> ORGANISM: Artificial Sequence
<220> FEATURE:
<223> OTHER INFORMATION: A synthetic oligonucleotide primer
```

<400> SEQUENCE: 94
ctgactttga caataggtcc tcaag                                      25

<210> SEQ ID NO 95
<211> LENGTH: 25
<212> TYPE: DNA
<213> ORGANISM: Artificial Sequence
<220> FEATURE:
<223> OTHER INFORMATION: A synthetic oligonucleotide primer

<400> SEQUENCE: 95
cttgaggacc tattgtcaaa gtcag                                      25

<210> SEQ ID NO 96
<211> LENGTH: 25
<212> TYPE: DNA
<213> ORGANISM: Artificial Sequence
<220> FEATURE:
<223> OTHER INFORMATION: A synthetic oligonucleotide primer

<400> SEQUENCE: 96
caagctcatg gacatcaaat agaag                                      25

<210> SEQ ID NO 97
<211> LENGTH: 25
<212> TYPE: DNA
<213> ORGANISM: Artificial Sequence
<220> FEATURE:
<223> OTHER INFORMATION: A synthetic oligonucleotide primer

<400> SEQUENCE: 97
attcttctat ttgatgtcca tgagc                                      25

<210> SEQ ID NO 98
<211> LENGTH: 26
<212> TYPE: DNA
<213> ORGANISM: Artificial Sequence
<220> FEATURE:
<223> OTHER INFORMATION: A synthetic oligonucleotide primer

<400> SEQUENCE: 98
tcagacccag tcactaacat ttctac                                     26

<210> SEQ ID NO 99
<211> LENGTH: 25
<212> TYPE: DNA
<213> ORGANISM: Artificial Sequence
<220> FEATURE:
<223> OTHER INFORMATION: A synthetic oligonucleotide primer

<400> SEQUENCE: 99
catgccaaga gtagaaatgt tagtg                                      25

<210> SEQ ID NO 100
<211> LENGTH: 25
<212> TYPE: DNA
<213> ORGANISM: Artificial Sequence
<220> FEATURE:
<223> OTHER INFORMATION: A synthetic oligonucleotide primer

<400> SEQUENCE: 100
aaatggtcca agagaatatg gtaag                                      25

```
<210> SEQ ID NO 101
<211> LENGTH: 24
<212> TYPE: DNA
<213> ORGANISM: Artificial Sequence
<220> FEATURE:
<223> OTHER INFORMATION: A synthetic oligonucleotide primer

<400> SEQUENCE: 101
ggatccattg tcaaggaaac ttac                                              24

<210> SEQ ID NO 102
<211> LENGTH: 23
<212> TYPE: DNA
<213> ORGANISM: Artificial Sequence
<220> FEATURE:
<223> OTHER INFORMATION: A synthetic oligonucleotide primer

<400> SEQUENCE: 102
agagattgcc atcagtacag gac                                               23

<210> SEQ ID NO 103
<211> LENGTH: 23
<212> TYPE: DNA
<213> ORGANISM: Artificial Sequence
<220> FEATURE:
<223> OTHER INFORMATION: A synthetic oligonucleotide primer

<400> SEQUENCE: 103
gtactgatgg caatctctgg ttc                                               23

<210> SEQ ID NO 104
<211> LENGTH: 25
<212> TYPE: DNA
<213> ORGANISM: Artificial Sequence
<220> FEATURE:
<223> OTHER INFORMATION: A synthetic oligonucleotide primer

<400> SEQUENCE: 104
atcattttgt tctgaaggat ttctc                                             25

<210> SEQ ID NO 105
<211> LENGTH: 24
<212> TYPE: DNA
<213> ORGANISM: Artificial Sequence
<220> FEATURE:
<223> OTHER INFORMATION: A synthetic oligonucleotide primer

<400> SEQUENCE: 105
aaatccttca gaacaaaatg atcc                                              24

<210> SEQ ID NO 106
<211> LENGTH: 25
<212> TYPE: DNA
<213> ORGANISM: Artificial Sequence
<220> FEATURE:
<223> OTHER INFORMATION: A synthetic oligonucleotide primer

<400> SEQUENCE: 106
taatcttctg gctctatcct tctcc                                             25

<210> SEQ ID NO 107
<211> LENGTH: 25
<212> TYPE: DNA
<213> ORGANISM: Artificial Sequence
<220> FEATURE:
<223> OTHER INFORMATION: A synthetic oligonucleotide primer
```

```
<400> SEQUENCE: 107
ctactggttg aggagaagga tagag                                          25

<210> SEQ ID NO 108
<211> LENGTH: 25
<212> TYPE: DNA
<213> ORGANISM: Artificial Sequence
<220> FEATURE:
<223> OTHER INFORMATION: A synthetic oligonucleotide primer

<400> SEQUENCE: 108
gagtttggaa ttcctattaa tgctc                                          25

<210> SEQ ID NO 109
<211> LENGTH: 23
<212> TYPE: DNA
<213> ORGANISM: Artificial Sequence
<220> FEATURE:
<223> OTHER INFORMATION: A synthetic oligonucleotide primer

<400> SEQUENCE: 109
aaactcagta tcagcagcct gtc                                            23

<210> SEQ ID NO 110
<211> LENGTH: 25
<212> TYPE: DNA
<213> ORGANISM: Artificial Sequence
<220> FEATURE:
<223> OTHER INFORMATION: A synthetic oligonucleotide primer

<400> SEQUENCE: 110
cactgatttg ctttctaacc gatac                                          25

<210> SEQ ID NO 111
<211> LENGTH: 24
<212> TYPE: DNA
<213> ORGANISM: Artificial Sequence
<220> FEATURE:
<223> OTHER INFORMATION: A synthetic oligonucleotide primer

<400> SEQUENCE: 111
tactgctgct gcttctaaca catc                                           24

<210> SEQ ID NO 112
<211> LENGTH: 25
<212> TYPE: DNA
<213> ORGANISM: Artificial Sequence
<220> FEATURE:
<223> OTHER INFORMATION: A synthetic oligonucleotide primer

<400> SEQUENCE: 112
cacaaggcaa ctggataatt aactg                                          25

<210> SEQ ID NO 113
<211> LENGTH: 25
<212> TYPE: DNA
<213> ORGANISM: Artificial Sequence
<220> FEATURE:
<223> OTHER INFORMATION: A synthetic oligonucleotide primer

<400> SEQUENCE: 113
ttaattatcc agttgccttg tgaag                                          25
```

```
<210> SEQ ID NO 114
<211> LENGTH: 22
<212> TYPE: DNA
<213> ORGANISM: Artificial Sequence
<220> FEATURE:
<223> OTHER INFORMATION: A synthetic oligonucleotide primer

<400> SEQUENCE: 114
agagagggca gacagatgta cc                                                22

<210> SEQ ID NO 115
<211> LENGTH: 20
<212> TYPE: DNA
<213> ORGANISM: Artificial Sequence
<220> FEATURE:
<223> OTHER INFORMATION: A synthetic oligonucleotide primer

<400> SEQUENCE: 115
tggaccattt aagggctgag                                                   20

<210> SEQ ID NO 116
<211> LENGTH: 20
<212> TYPE: DNA
<213> ORGANISM: Artificial Sequence
<220> FEATURE:
<223> OTHER INFORMATION: A synthetic oligonucleotide primer

<400> SEQUENCE: 116
gactctgtgg gaagctgagg                                                   20

<210> SEQ ID NO 117
<211> LENGTH: 25
<212> TYPE: DNA
<213> ORGANISM: Artificial Sequence
<220> FEATURE:
<223> OTHER INFORMATION: A synthetic oligonucleotide primer

<400> SEQUENCE: 117
gcatacattt ctttcacagg gatac                                             25

<210> SEQ ID NO 118
<211> LENGTH: 25
<212> TYPE: DNA
<213> ORGANISM: Artificial Sequence
<220> FEATURE:
<223> OTHER INFORMATION: A synthetic oligonucleotide primer

<400> SEQUENCE: 118
tggcttactt tacagttcca gaaag                                             25

<210> SEQ ID NO 119
<211> LENGTH: 21
<212> TYPE: DNA
<213> ORGANISM: Artificial Sequence
<220> FEATURE:
<223> OTHER INFORMATION: A synthetic oligonucleotide primer

<400> SEQUENCE: 119
cggagcccat agttctttct c                                                 21

<210> SEQ ID NO 120
<211> LENGTH: 20
<212> TYPE: DNA
<213> ORGANISM: Artificial Sequence
<220> FEATURE:
<223> OTHER INFORMATION: A synthetic oligonucleotide primer
```

```
<400> SEQUENCE: 120
ttatttgtct ccccgcactc                                               20

<210> SEQ ID NO 121
<211> LENGTH: 28
<212> TYPE: DNA
<213> ORGANISM: Artificial Sequence
<220> FEATURE:
<223> OTHER INFORMATION: A synthetic oligonucleotide primer

<400> SEQUENCE: 121
aacaaataaa acttaatcaa ggaaactg                                      28

<210> SEQ ID NO 122
<211> LENGTH: 26
<212> TYPE: DNA
<213> ORGANISM: Artificial Sequence
<220> FEATURE:
<223> OTHER INFORMATION: A synthetic oligonucleotide primer

<400> SEQUENCE: 122
cttgttgagt taggatttac cagaac                                        26
```